US011241455B2

(12) United States Patent
Xu et al.

(10) Patent No.: US 11,241,455 B2
(45) Date of Patent: Feb. 8, 2022

(54) METHODS OF TREATING DISEASE BY METABOLIC CONTROL OF T-CELL DIFFERENTIATION

(71) Applicant: The J. David Gladstone Institutes, a testamentary trust established under the Will of J. David Gladstone, San Francisco, CA (US)

(72) Inventors: Tao Xu, San Francisco, CA (US); Sheng Ding, Orinda, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 554 days.

(21) Appl. No.: 16/066,659

(22) PCT Filed: Jan. 12, 2017

(86) PCT No.: PCT/US2017/013252
§ 371 (c)(1),
(2) Date: Jun. 27, 2018

(87) PCT Pub. No.: WO2017/123808
PCT Pub. Date: Jul. 20, 2017

(65) Prior Publication Data
US 2019/0022142 A1 Jan. 24, 2019

Related U.S. Application Data

(60) Provisional application No. 62/279,463, filed on Jan. 15, 2016.

(51) Int. Cl.
| | | |
|---|---|---|
| *A61K 35/17* | (2015.01) | |
| *A61K 31/133* | (2006.01) | |
| *A61K 31/42* | (2006.01) | |
| *A61K 31/223* | (2006.01) | |
| *A61K 31/195* | (2006.01) | |
| *A61K 31/225* | (2006.01) | |
| *A61K 31/197* | (2006.01) | |
| *A61P 37/06* | (2006.01) | |
| *A61P 35/00* | (2006.01) | |
| A61P 29/00 | (2006.01) | |
| A61K 38/20 | (2006.01) | |
| A61K 38/21 | (2006.01) | |

(52) U.S. Cl.
CPC ............ *A61K 35/17* (2013.01); *A61K 31/133* (2013.01); *A61K 31/195* (2013.01); *A61K 31/197* (2013.01); *A61K 31/223* (2013.01); *A61K 31/225* (2013.01); *A61K 31/42* (2013.01); *A61P 35/00* (2018.01); *A61P 37/06* (2018.01); A61K 38/20 (2013.01); A61K 38/21 (2013.01); A61P 29/00 (2018.01)

(58) Field of Classification Search
CPC ...................................................... A61K 35/17
See application file for complete search history.

(56) References Cited

U.S. PATENT DOCUMENTS

| | | | | |
|---|---|---|---|---|
| 9,526,707 | B2 * | 12/2016 | Elford | ................. A61K 31/133 |
| 2004/0235755 | A1 | 11/2004 | Eigenbrodt et al. | |
| 2007/0238781 | A1 * | 10/2007 | Eigenbrodt | ............. A61P 31/04 514/506 |
| 2010/0216226 | A1 | 8/2010 | Hyde et al. | |
| 2011/0105617 | A1 | 5/2011 | Pierzynowski et al. | |
| 2015/0031627 | A1 | 1/2015 | Lemieux et al. | |
| 2015/0240286 | A1 | 8/2015 | Dang et al. | |
| 2015/0273086 | A1 | 10/2015 | Cabella et al. | |

FOREIGN PATENT DOCUMENTS

| | | |
|---|---|---|
| EP | 3402571 | 11/2018 |
| PL | 217 053 B1 | 6/2014 |
| PL | 217053 | 6/2014 |
| WO | WO 1993019163 | 9/1993 |
| WO | WO 2000031239 | 6/2000 |
| WO | WO 2003025126 | 3/2003 |
| WO | 2006024491 | 3/2006 |
| WO | WO 2006/024491 | 3/2006 |

(Continued)

OTHER PUBLICATIONS

"International Application Serial No. PCT US2017 013252, International Search Report dated May 31, 2017", 4 pgs.
"International Application Serial No. PCT US2017 013252, Written Opinion dated May 31, 2017", 5 pgs.
"International Application Serial No. PCT US2017 013252, International Preliminary Report on Patentability dated Jul. 26, 2018", 7 pgs.
"European Application Serial No. 17738971.5, Response to Communication pursuant to Rules 161(1) and 162 EPC filed Mar. 11, 2019", 6 pgs.
"European Application Serial No. 17738971.5, Response filed Feb. 28, 2020 to Extended European Search Report dated Jul. 30, 2019", 13 pgs.

(Continued)

*Primary Examiner* — Scott Long
(74) *Attorney, Agent, or Firm* — Schwegman Lundberg & Woessner, P.A.

(57) ABSTRACT

Provided herein are methods for treating an individual for a disease (e.g., an autoimmune disease or a cancer) using an active agent which affects metabolism of α-ketoglutarate (α-KG) and/or 2-hydroxyglutarate (2-HG) in differentiating T cells. In some embodiments, a Got1 inhibitor is used to generate a population of T cells enriched in peripheral regulatory T (iTreg) cells, which population enriched in iTreg cells may find use in treating an autoimmune disease. In some embodiments, a TCA cycle-associated metabolite, or a derivative thereof, is used to generate a population of T cells in enriched in IL-17- and IL-17F-producing CD4 T ($T_H17$) cells, which population enriched in $T_H17$ cells may find use in treating a cancer.

16 Claims, 31 Drawing Sheets
Specification includes a Sequence Listing.

(56) References Cited

FOREIGN PATENT DOCUMENTS

| WO | 2011143160 | 11/2011 |
|---|---|---|
| WO | WO 2011/143160 | 11/2011 |
| WO | WO 2015109180 | 7/2015 |
| WO | 2015123229 | 8/2015 |
| WO | WO 2015/123229 | 8/2015 |
| WO | 2015138837 | 9/2015 |
| WO | WO 2015/138837 | 9/2015 |
| WO | 2017123808 | 7/2017 |

OTHER PUBLICATIONS

"European Application Serial No. 17738971.5, Extended European Search Report dated Jul. 30, 2019", 6 pgs.

Amarzguioui et al. (2004) "An algorithm for selection of functional siRNA sequences"; *Biochem. Biophys. Res. Commun.* 316; pp. 1050-1058.

Beurel, et al (2014) "Astrocytes Modulate the Polarization of CD4+ T Cells to Th1 Cells"; PLoS One 9(1); pp. 1-10.

Kim, et al. (2007) "CREB/ATF-dependent T cell receptor-induced FoxP3 gene expression: a role for DNA methylation"; J Exp Med 204 (7), 1543-1551.

Klysz et al. (2015) "Glutamine-dependent a-ketoglutarate production regulates the balance between T helper 1 cell and regulatory T cell generation"; Science Signaling vol. 8 Issue 396; pp. 1-14.

Palmer et al. (2015) "Glucose metabolism regulates T cell activation, differentiation, and functions"; Front Immunol, 6(1); pp. 1-6.

Reynolds et al. (2004) "Rational siRNA design for RNA interference"; Nat. *Biotechnol.* 22; pp. 326-330.

Shi et al. (2011) "HIF1α-dependent glycolytic pathway orchestrates a metabolic checkpoint for the differentiation of TH17 and Treg cells"; J Exp Med. 208(7); pp. 1367-1376.

Shomron N.; *Deep Sequencing Data Analysis* (Methods in Molecular Biology, Humana Press, 2013).

Smith and Waterman (1981) "Comparison of Biosequences"; *Advances in Appl. Math. 2*; pp. 482-489.

Ui-Tei, et al. (2004) "Guidelines for the selection of highly effective siRNA sequences for mammalian and chick RNA interference"; *Nucleic Acids Res.* 32(3); pp. 936-948.

Wang and Green (2012) "Metabolic reprogramming and metabolic dependency in T cells"; Immunol Rev. Sep.;249(1); pp. 14-26.

"European Application Serial No. 17738971.5, Communication pursuant to Article 94(3) EPC dated Sep. 30, 2020", 4 pgs.

"European Application Serial No. 17738971.5, Response filed Feb. 8, 2021 to Communication pursuant to Article 94(3) EPC dated Sep. 30, 2020", 7 pgs.

\* cited by examiner

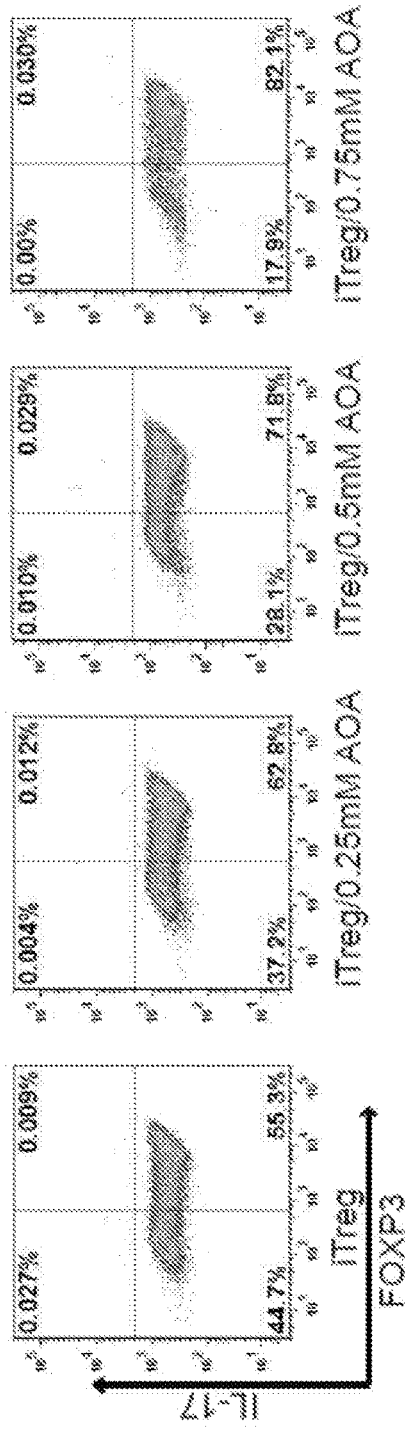
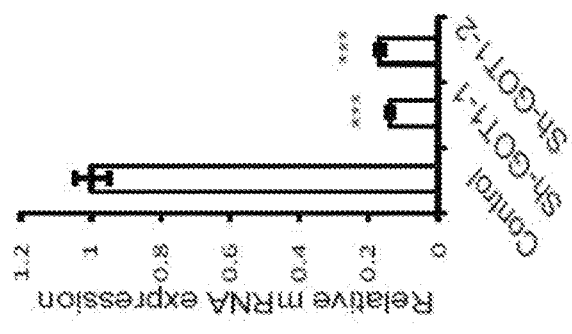
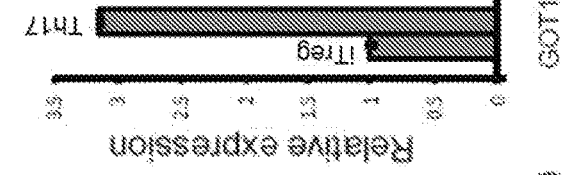
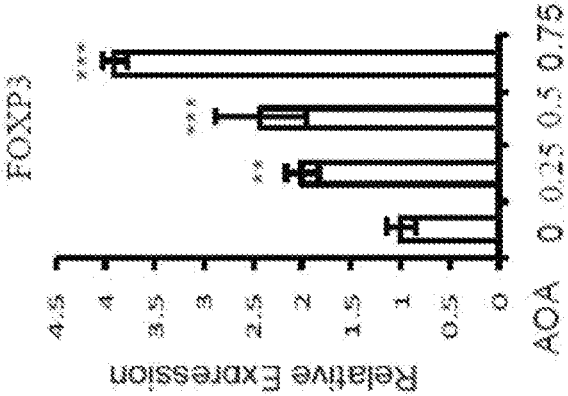

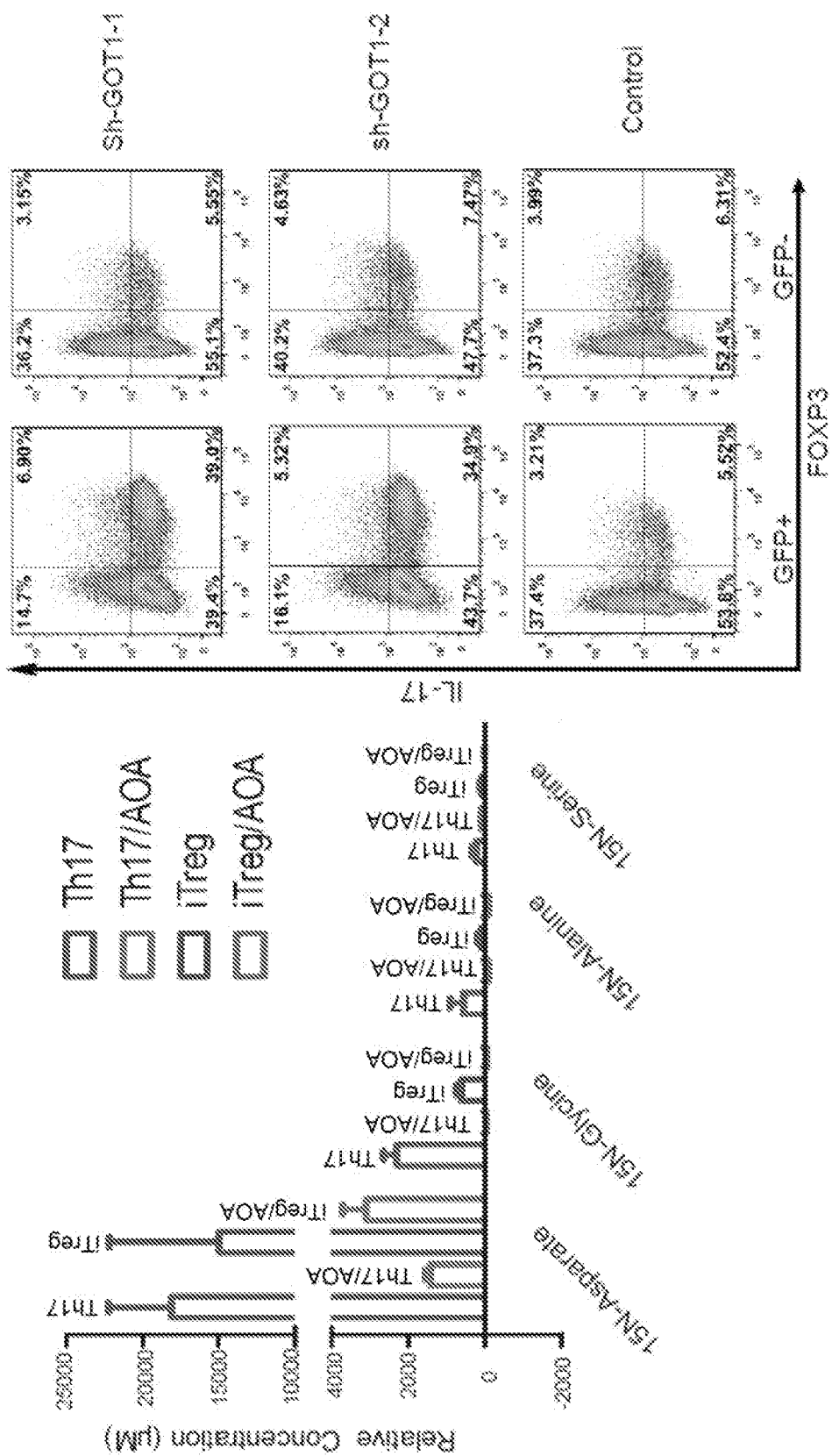

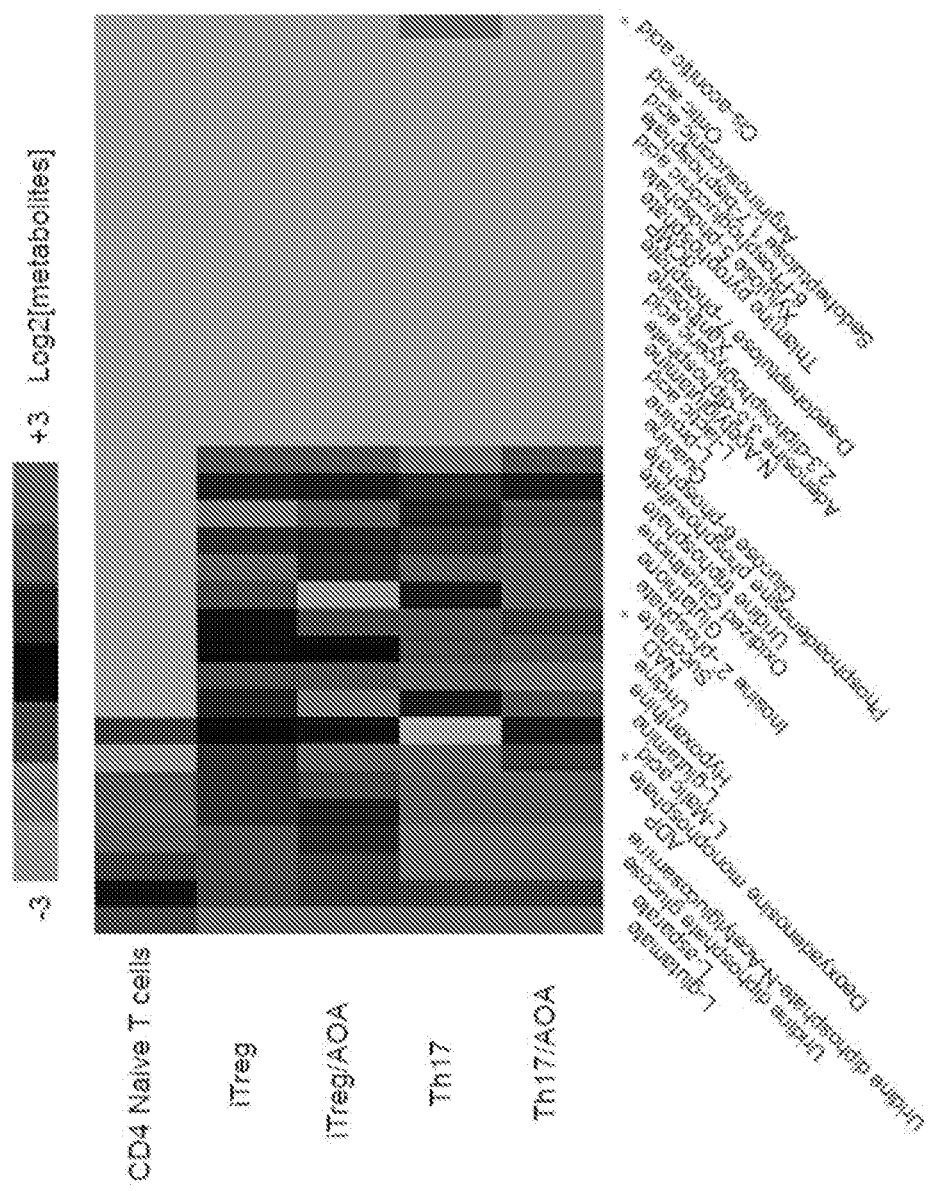

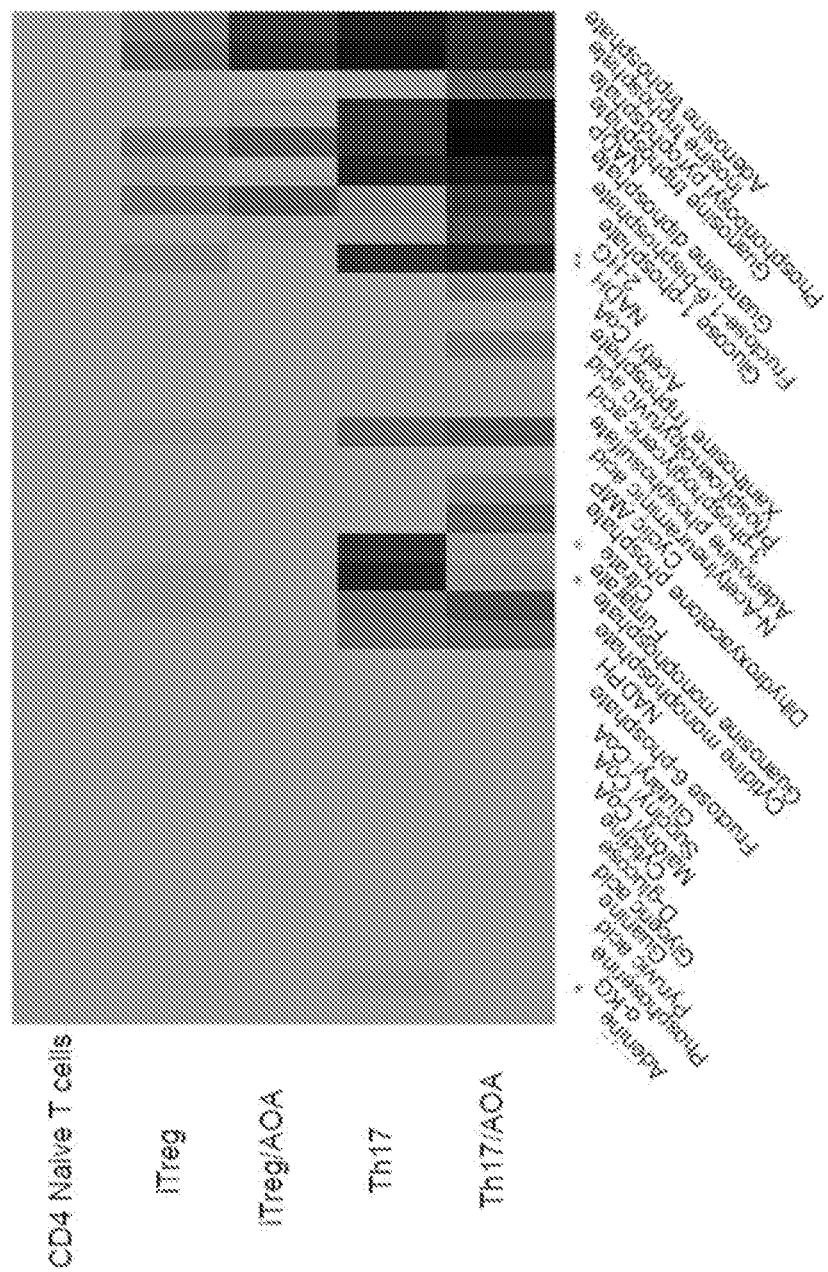
Fig. 2a, cont.

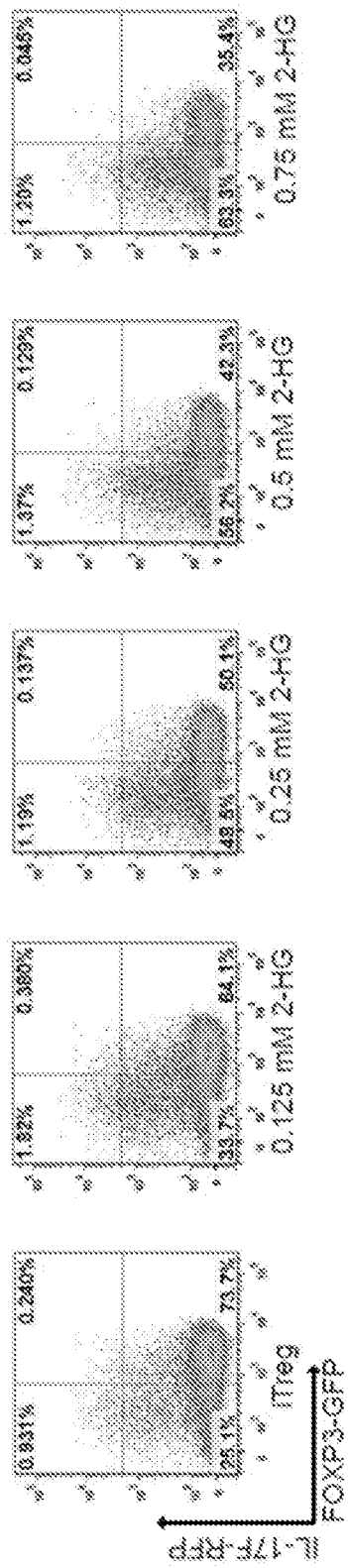
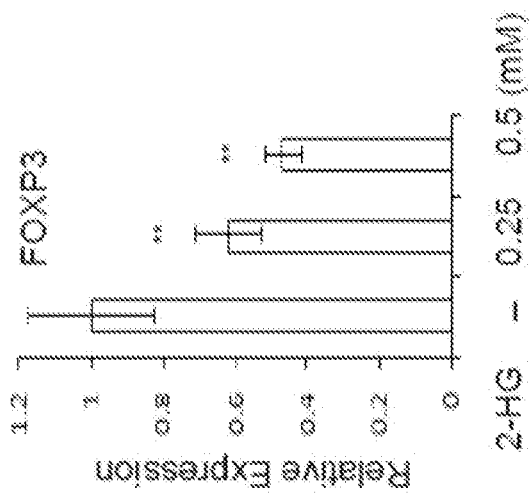
Fig. 3c
Fig. 3d

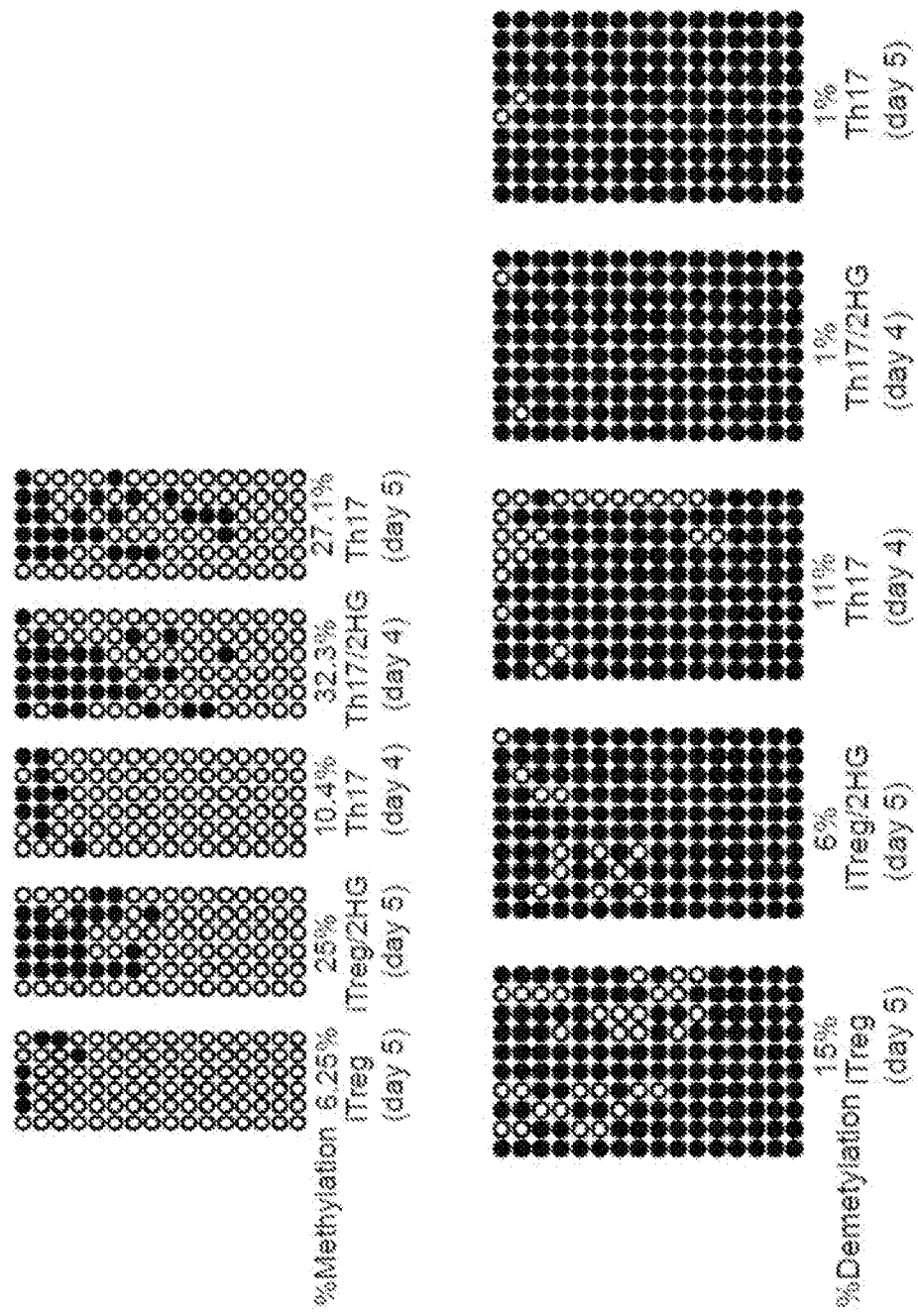

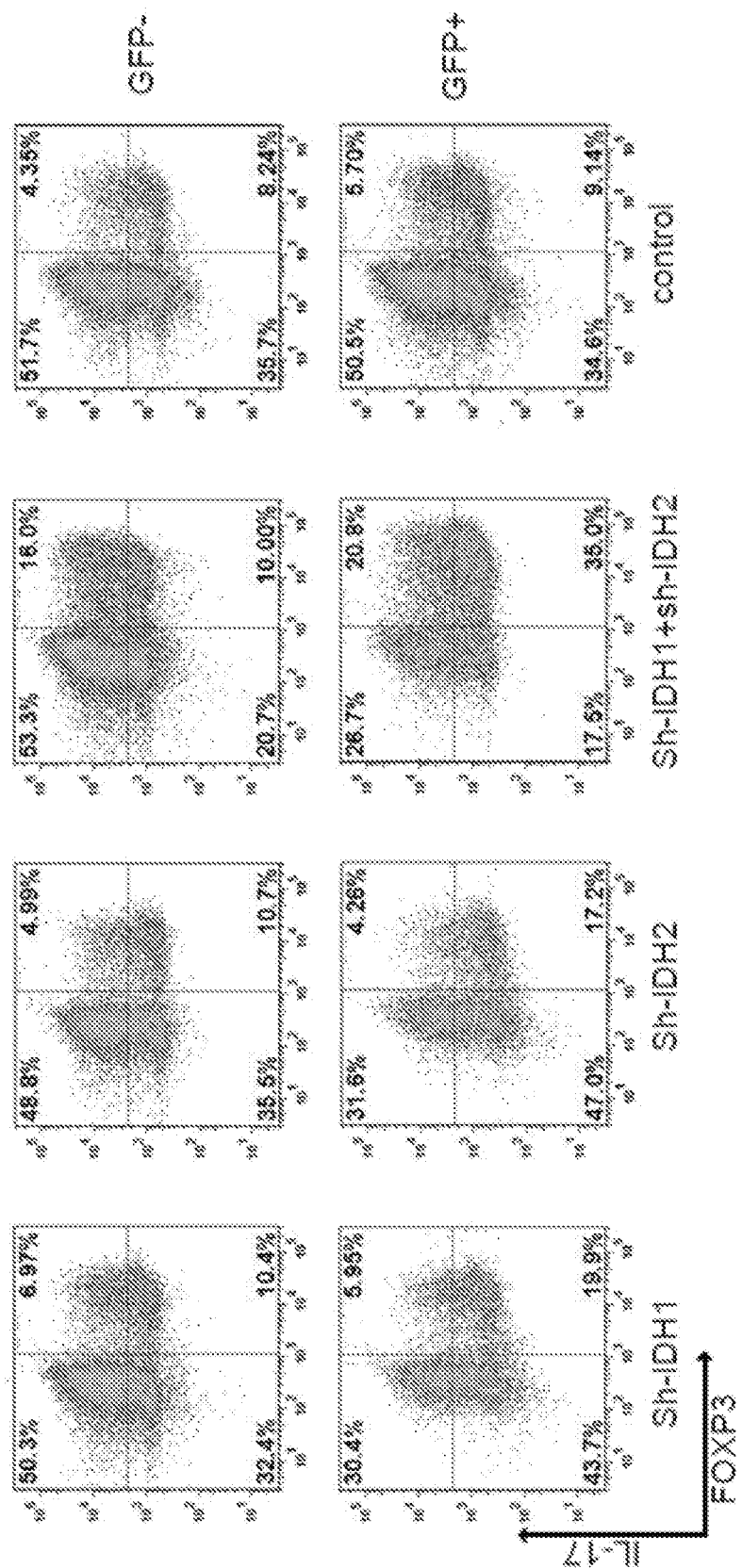

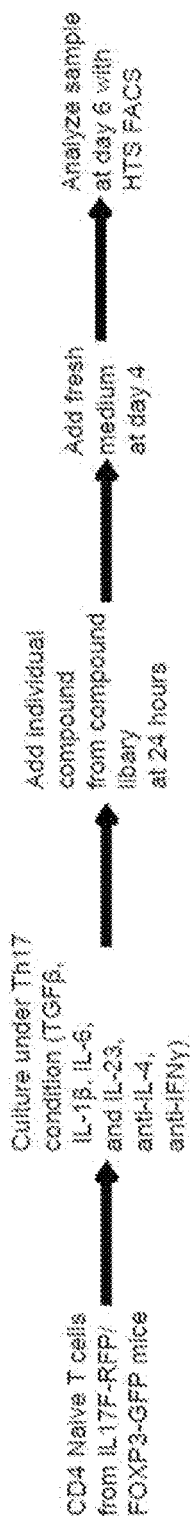
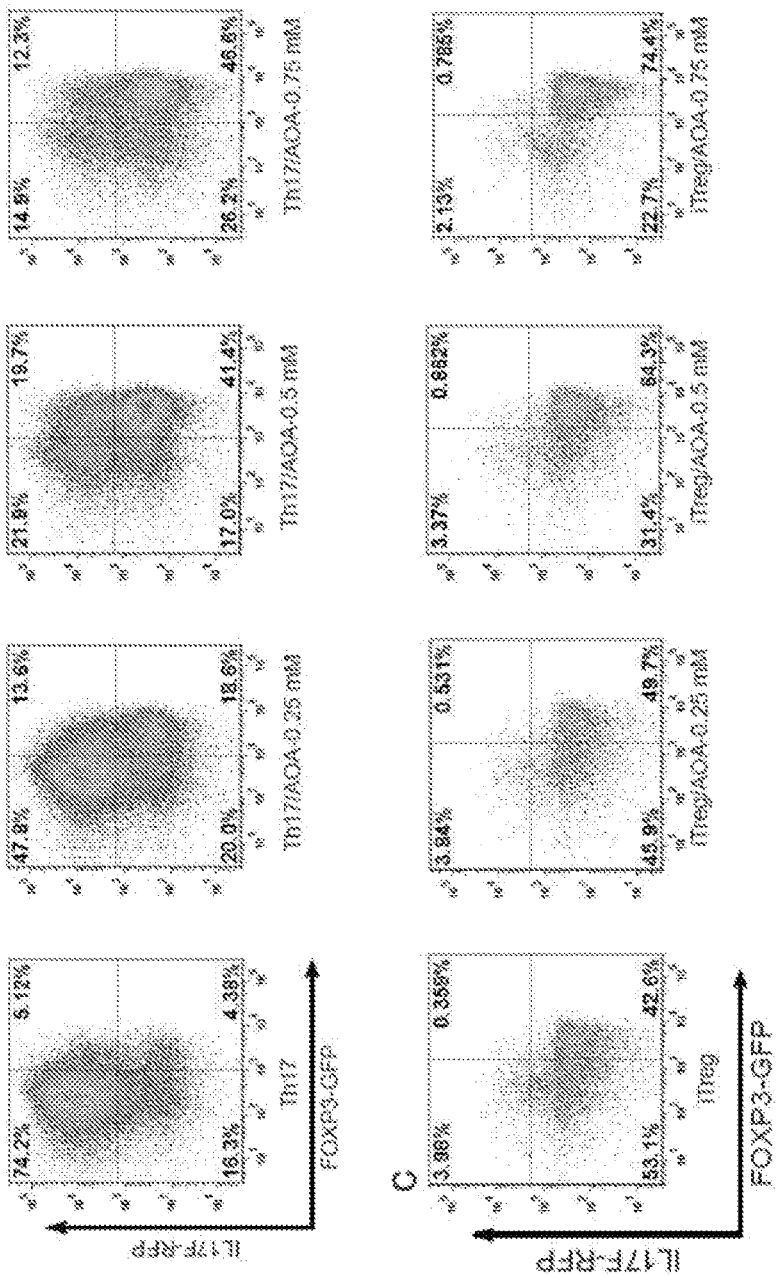

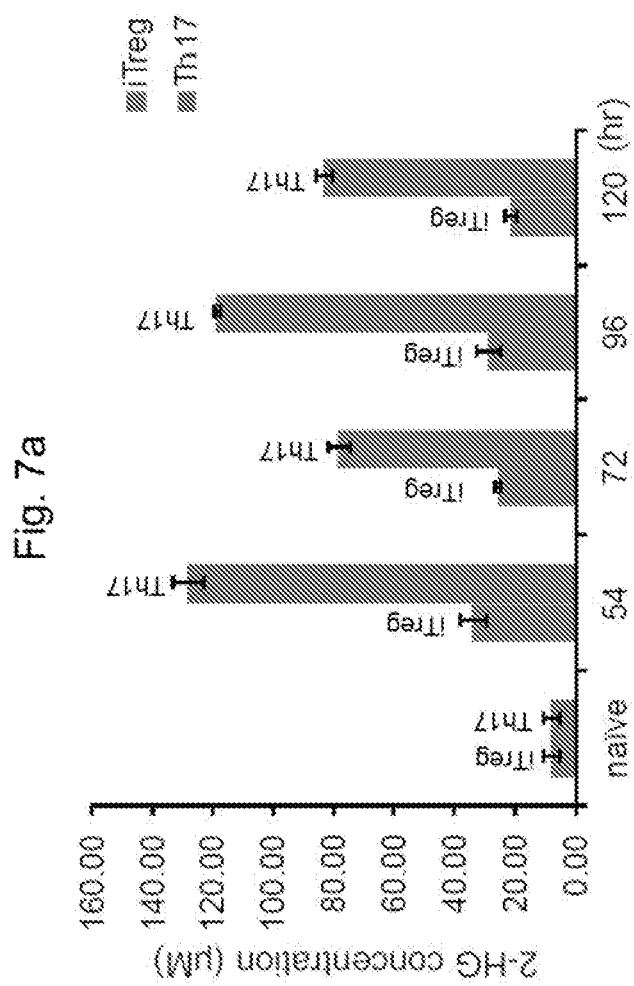

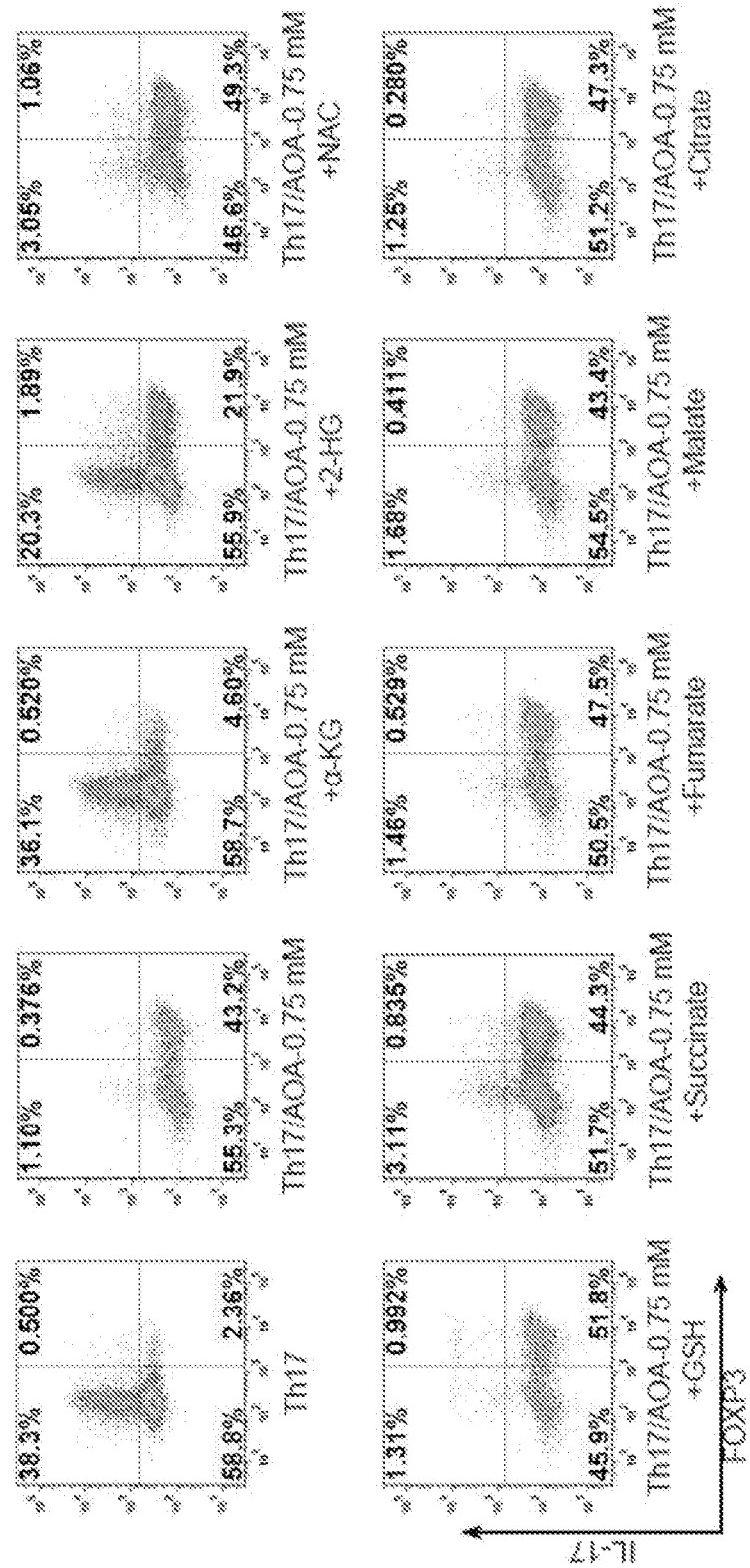

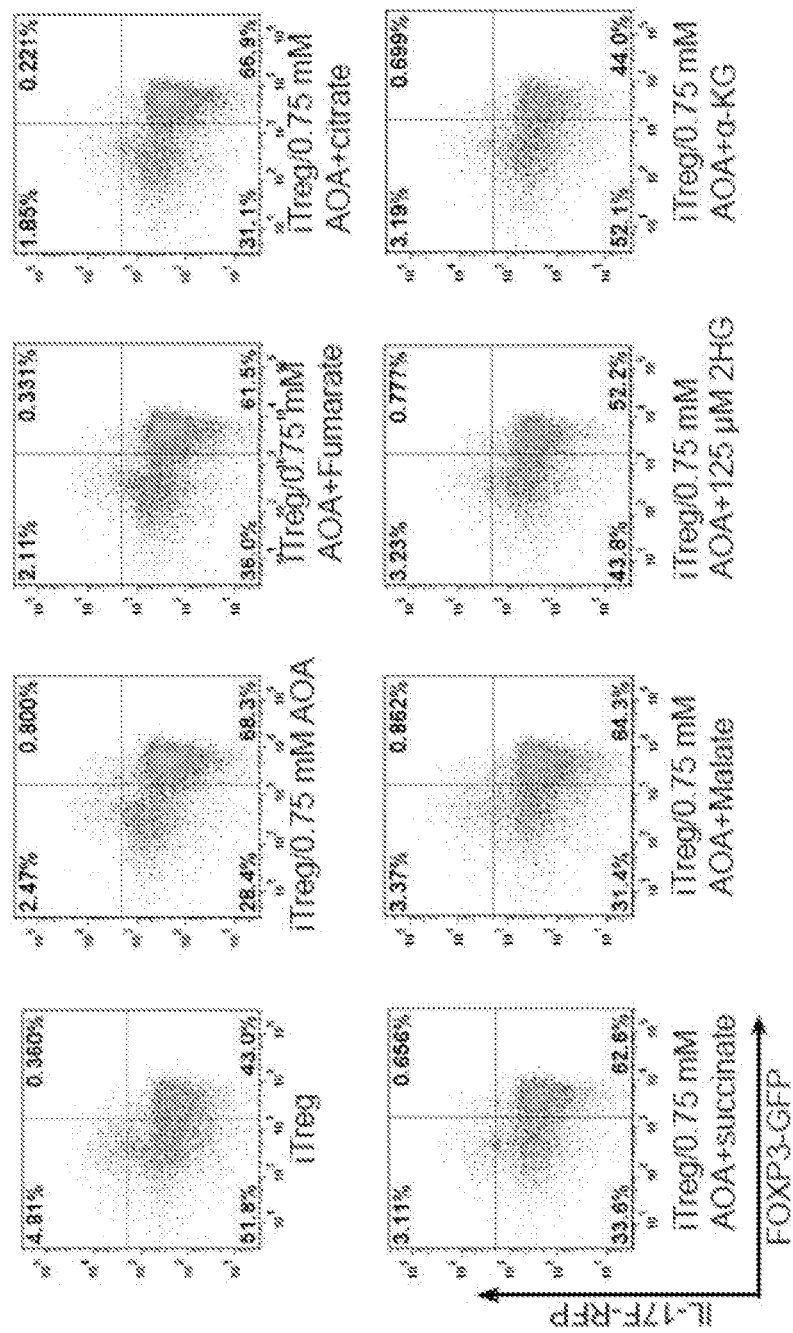

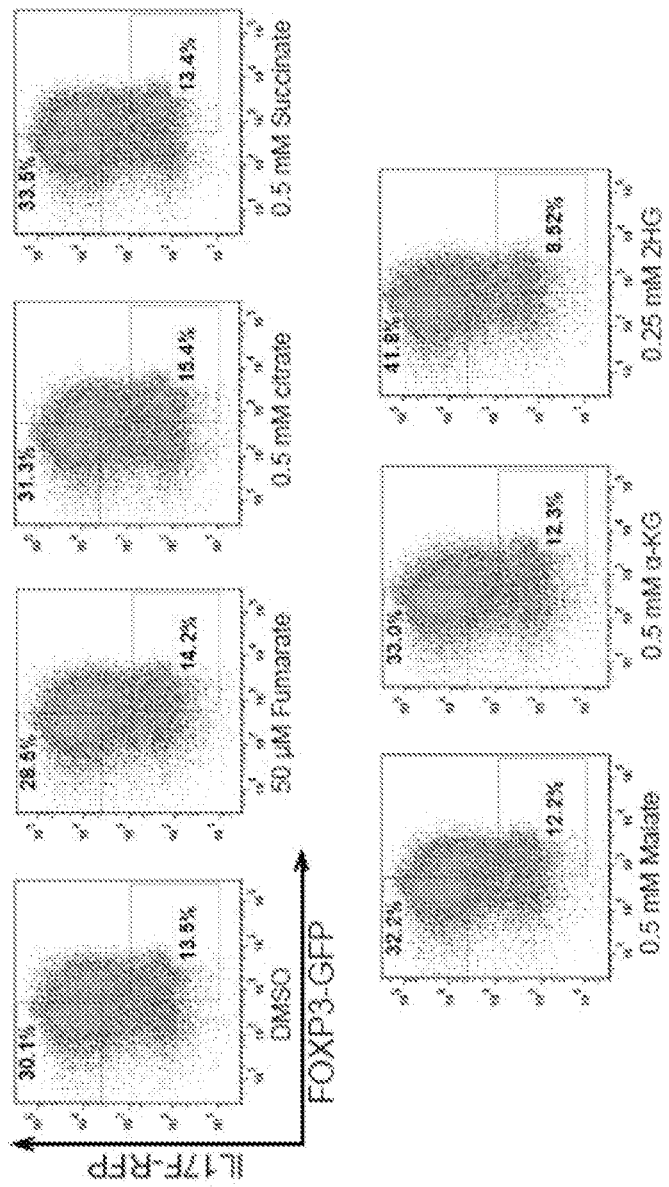

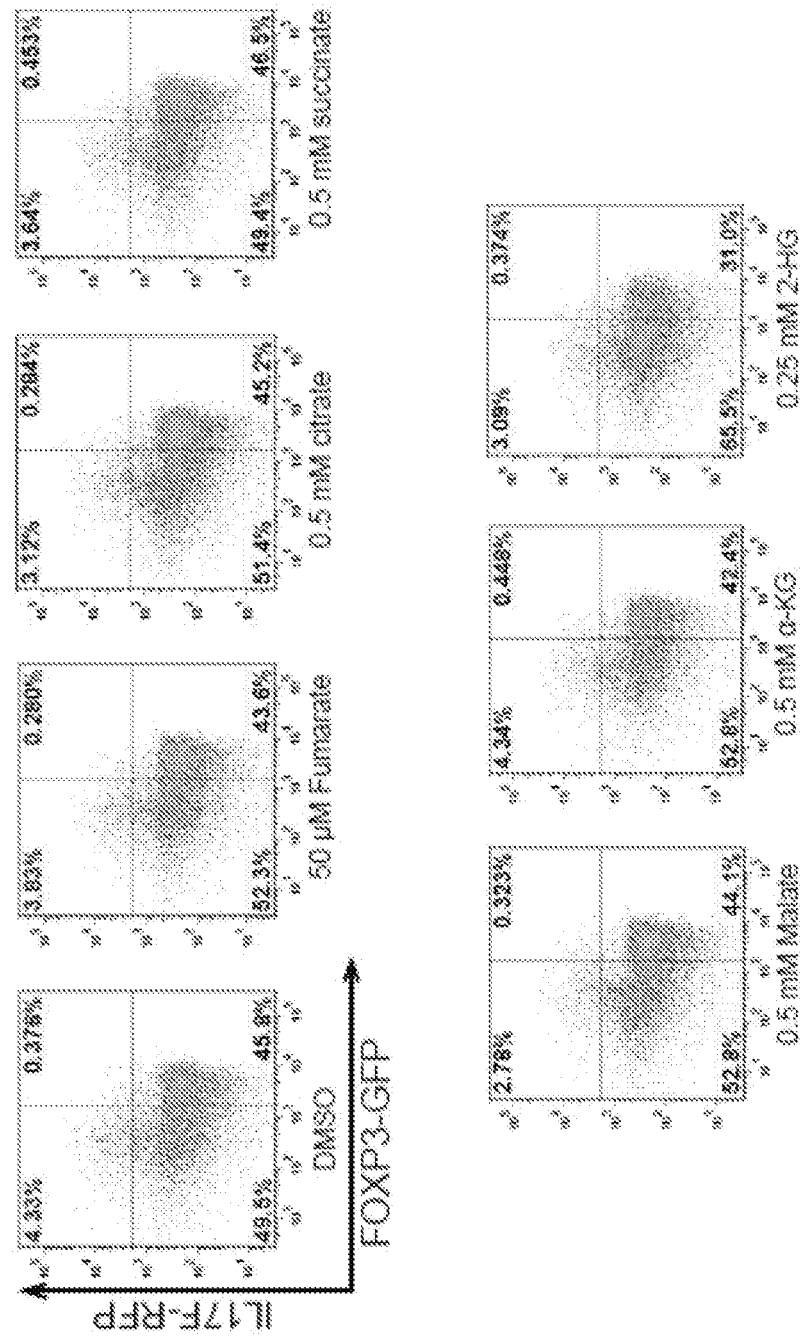

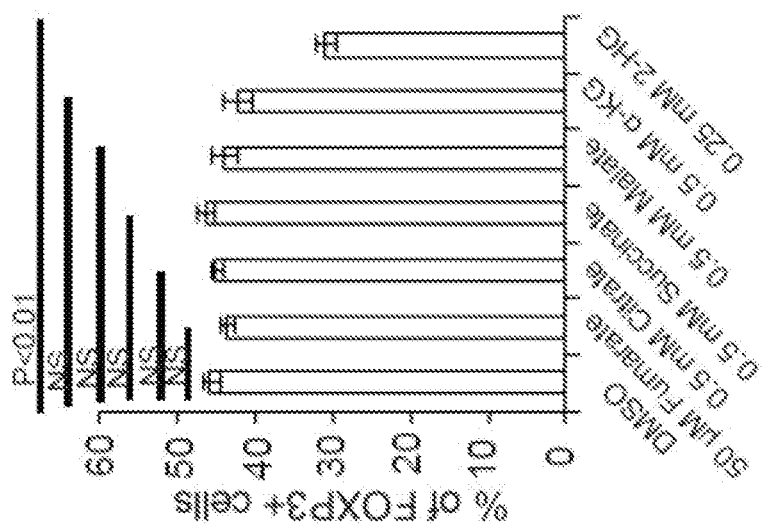

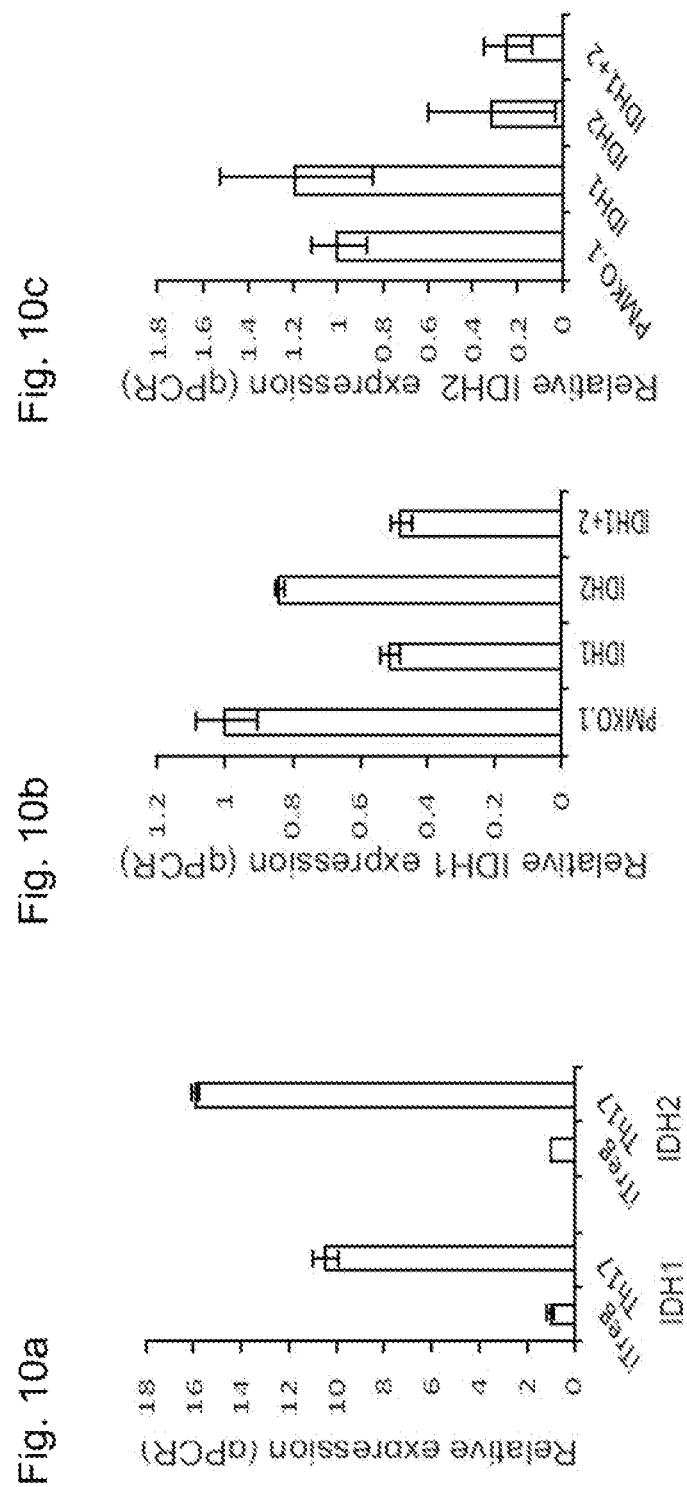

Fig. 11

(GOT1) aspartate aminotransferase, cytoplasmic [Homo sapiens]
Gene ID: 2805
Accession: NP_002070 mappsvfaevpqaqpvlvfkltadfredpdprkvnlgvgayrtddchpwvlpvvkkveqkiandnsinheylpilglaefrscasrlal
gddspalkekrvggvqslggtgalrigadflarwyngtnnkntpvyvssptwenhnavfsaagfkdirsyrywdaekrgldiqgfindl
enapefsivvlhacahnptgidptpeqwkgiasvmkhrflfpffdsayqgfasgnlerdawairyfvsegfefcagsisknfglyner
vgnltvvgkepesilgvlsqmekivritwsnppaggarivastisnpelfeewtgnvktmadriltmrselrarlealktpgtwnhitd
qigmfsftginpkqveylvnekhiylipsgrinvsgittknidyvatsiheavtkig (SEQ ID NO:1)

SEQUENCE LISTING

```
<160> NUMBER OF SEQ ID NOS: 50

<210> SEQ ID NO 1
<211> LENGTH: 413
<212> TYPE: PRT
<213> ORGANISM: Homo sapiens

<400> SEQUENCE: 1

Met Ala Pro Pro Ser Val Phe Ala Glu Val Pro Gln Ala Gln Pro Val
1               5                   10                  15

Leu Val Phe Lys Leu Thr Ala Asp Phe Arg Glu Asp Pro Asp Pro Arg
            20                  25                  30

Lys Val Asn Leu Gly Val Gly Ala Tyr Arg Thr Asp Asp Cys His Pro
        35                  40                  45

Trp Val Leu Pro Val Val Lys Lys Val Glu Gln Lys Ile Ala Asn Asp
    50                  55                  60

Asn Ser Leu Asn His Glu Tyr Leu Pro Ile Leu Gly Leu Ala Glu Phe
65                  70                  75                  80

Arg Ser Cys Ala Ser Arg Leu Ala Leu Gly Asp Asp Ser Pro Ala Leu
                85                  90                  95

Lys Glu Lys Arg Val Gly Gly Val Gln Ser Leu Gly Gly Thr Gly Ala
            100                 105                 110

Leu Arg Ile Gly Ala Asp Phe Leu Ala Arg Trp Tyr Asn Gly Thr Asn
        115                 120                 125

Asn Lys Asn Thr Pro Val Tyr Val Ser Ser Pro Thr Trp Glu Asn His
    130                 135                 140

Asn Ala Val Phe Ser Ala Ala Gly Phe Lys Asp Ile Arg Ser Tyr Arg
145                 150                 155                 160

Tyr Trp Asp Ala Glu Lys Arg Gly Leu Asp Leu Gln Gly Phe Leu Asn
                165                 170                 175

Asp Leu Glu Asn Ala Pro Glu Phe Ser Ile Val Val Leu His Ala Cys
            180                 185                 190

Ala His Asn Pro Thr Gly Ile Asp Pro Thr Pro Glu Gln Trp Lys Gln
        195                 200                 205

Ile Ala Ser Val Met Lys His Arg Phe Leu Phe Pro Phe Phe Asp Ser
    210                 215                 220

Ala Tyr Gln Gly Phe Ala Ser Gly Asn Leu Glu Arg Asp Ala Trp Ala
225                 230                 235                 240

Ile Arg Tyr Phe Val Ser Glu Gly Phe Glu Phe Phe Cys Ala Gln Ser
                245                 250                 255

Phe Ser Lys Asn Phe Gly Leu Tyr Asn Glu Arg Val Gly Asn Leu Thr
            260                 265                 270

Val Val Gly Lys Glu Pro Glu Ser Ile Leu Gln Val Leu Ser Gln Met
        275                 280                 285
```

```
Glu Lys Ile Val Arg Ile Thr Trp Ser Asn Pro Pro Ala Gln Gly Ala
    290                 295                 300
Arg Ile Val Ala Ser Thr Leu Ser Asn Pro Glu Leu Phe Glu Glu Trp
305                 310                 315                 320
Thr Gly Asn Val Lys Thr Met Ala Asp Arg Ile Leu Thr Met Arg Ser
                325                 330                 335
Glu Leu Arg Ala Arg Leu Glu Ala Leu Lys Thr Pro Gly Thr Trp Asn
            340                 345                 350
His Ile Thr Asp Gln Ile Gly Met Phe Ser Phe Thr Gly Leu Asn Pro
        355                 360                 365
Lys Gln Val Glu Tyr Leu Val Asn Glu Lys His Ile Tyr Leu Leu Pro
370                 375                 380
Ser Gly Arg Ile Asn Val Ser Gly Leu Thr Thr Lys Asn Leu Asp Tyr
385                 390                 395                 400
Val Ala Thr Ser Ile His Glu Ala Val Thr Lys Ile Gln
                405                 410

<210> SEQ ID NO 2
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 2

Met Glu Val Gly Trp Tyr Arg Ser Pro Phe Ser Arg Val His Leu Tyr
1               5                   10                  15
Arg Asn Gly Lys
            20

<210> SEQ ID NO 3
<211> LENGTH: 24
<212> TYPE: DNA
<213> ORGANISM: Artificial Sequence
<220> FEATURE:
<223> OTHER INFORMATION: Synethic primer

<400> SEQUENCE: 3
tccatctttg tcctccatgc ctgt                                      24

<210> SEQ ID NO 4
<211> LENGTH: 24
<212> TYPE: DNA
<213> ORGANISM: Artificial Sequence
<220> FEATURE:
<223> OTHER INFORMATION: Synethic primer

<400> SEQUENCE: 4
agatgcaaag ccctgatagg ctga                                      24

<210> SEQ ID NO 5
<211> LENGTH: 24
<212> TYPE: DNA
<213> ORGANISM: Artificial Sequence
<220> FEATURE:
<223> OTHER INFORMATION: Synethic primer

<400> SEQUENCE: 5
tcatcgagca gggcatcaat gtct                                      24

<210> SEQ ID NO 6
<211> LENGTH: 24
```

<212> TYPE: DNA
<213> ORGANISM: Artificial Sequence
<220> FEATURE:
<223> OTHER INFORMATION: Synethic primer

<400> SEQUENCE: 6
tcttcagctg tgactccacc cttt                                               24

<210> SEQ ID NO 7
<211> LENGTH: 24
<212> TYPE: DNA
<213> ORGANISM: Artificial Sequence
<220> FEATURE:
<223> OTHER INFORMATION: Synethic primer

<400> SEQUENCE: 7
tgaaggaagc atcttggagg ctga                                               24

<210> SEQ ID NO 8
<211> LENGTH: 24
<212> TYPE: DNA
<213> ORGANISM: Artificial Sequence
<220> FEATURE:
<223> OTHER INFORMATION: Synethic primer

<400> SEQUENCE: 8
cccattggca ccttcagcaa tgat                                               24

<210> SEQ ID NO 9
<211> LENGTH: 24
<212> TYPE: DNA
<213> ORGANISM: Artificial Sequence
<220> FEATURE:
<223> OTHER INFORMATION: Synethic primer

<400> SEQUENCE: 9
aactaactga tcacggtgcc tggt                                               24

<210> SEQ ID NO 10
<211> LENGTH: 24
<212> TYPE: DNA
<213> ORGANISM: Artificial Sequence
<220> FEATURE:
<223> OTHER INFORMATION: Synethic primer

<400> SEQUENCE: 10
ttgcttggtg gctgctactt tgtg                                               24

<210> SEQ ID NO 11
<211> LENGTH: 24
<212> TYPE: DNA
<213> ORGANISM: Artificial Sequence
<220> FEATURE:
<223> OTHER INFORMATION: Synethic primer

<400> SEQUENCE: 11
acagcctggg tgcctatagc atta                                               24

<210> SEQ ID NO 12
<211> LENGTH: 24
<212> TYPE: DNA
<213> ORGANISM: Artificial Sequence
<220> FEATURE:
<223> OTHER INFORMATION: Synethic primer

<400> SEQUENCE: 12

-continued atatgttgtt cgggtctgca ggga    24

<210> SEQ ID NO 13
<211> LENGTH: 24
<212> TYPE: DNA
<213> ORGANISM: Artificial Sequence
<220> FEATURE:
<223> OTHER INFORMATION: Synethic primer

<400> SEQUENCE: 13
tgcacacagt tccttccaaa tggc    24

<210> SEQ ID NO 14
<211> LENGTH: 24
<212> TYPE: DNA
<213> ORGANISM: Artificial Sequence
<220> FEATURE:
<223> OTHER INFORMATION: Synethic primer

<400> SEQUENCE: 14
agcttgggcc accatgtcat ctat    24

<210> SEQ ID NO 15
<211> LENGTH: 19
<212> TYPE: DNA
<213> ORGANISM: Artificial Sequence
<220> FEATURE:
<223> OTHER INFORMATION: Synethic primer

<400> SEQUENCE: 15
cagcactgac tgtccccag    19

<210> SEQ ID NO 16
<211> LENGTH: 20
<212> TYPE: DNA
<213> ORGANISM: Artificial Sequence
<220> FEATURE:
<223> OTHER INFORMATION: Synethic primer

<400> SEQUENCE: 16
ccttgatgaa ctgccagatg    20

<210> SEQ ID NO 17
<211> LENGTH: 22
<212> TYPE: DNA
<213> ORGANISM: Artificial Sequence
<220> FEATURE:
<223> OTHER INFORMATION: Synethic primer

<400> SEQUENCE: 17
gtccaagctg ctatctggta tt    22

<210> SEQ ID NO 18
<211> LENGTH: 23
<212> TYPE: DNA
<213> ORGANISM: Artificial Sequence
<220> FEATURE:
<223> OTHER INFORMATION: Synethic primer

<400> SEQUENCE: 18
tctgatgacc tgtgactcat ttc    23

<210> SEQ ID NO 19
<211> LENGTH: 21
<212> TYPE: DNA
<213> ORGANISM: Artificial Sequence

```
<220> FEATURE:
<223> OTHER INFORMATION: Synethic primer

<400> SEQUENCE: 19
gagagggaaa gggttgctaa a                                              21

<210> SEQ ID NO 20
<211> LENGTH: 21
<212> TYPE: DNA
<213> ORGANISM: Artificial Sequence
<220> FEATURE:
<223> OTHER INFORMATION: Synethic primer

<400> SEQUENCE: 20
gaagcccgtt atctcgaagt c                                              21

<210> SEQ ID NO 21
<211> LENGTH: 20
<212> TYPE: DNA
<213> ORGANISM: Artificial Sequence
<220> FEATURE:
<223> OTHER INFORMATION: Synethic primer

<400> SEQUENCE: 21
aaatcgtgcg tgacatcaaa                                                20

<210> SEQ ID NO 22
<211> LENGTH: 20
<212> TYPE: DNA
<213> ORGANISM: Artificial Sequence
<220> FEATURE:
<223> OTHER INFORMATION: Synethic primer

<400> SEQUENCE: 22
aaggaaggct ggaaaagagc                                                20

<210> SEQ ID NO 23
<211> LENGTH: 20
<212> TYPE: DNA
<213> ORGANISM: Artificial Sequence
<220> FEATURE:
<223> OTHER INFORMATION: Synethic primer

<400> SEQUENCE: 23
caggaagaca gcaccatgaa                                                20

<210> SEQ ID NO 24
<211> LENGTH: 24
<212> TYPE: DNA
<213> ORGANISM: Artificial Sequence
<220> FEATURE:
<223> OTHER INFORMATION: Synethic primer

<400> SEQUENCE: 24
tcttctccaa cctgaaggaa ttag                                           24

<210> SEQ ID NO 25
<211> LENGTH: 24
<212> TYPE: DNA
<213> ORGANISM: Artificial Sequence
<220> FEATURE:
<223> OTHER INFORMATION: Synethic primer

<400> SEQUENCE: 25
aggccattca gtatgtggtg gagt                                           24
```

<210> SEQ ID NO 26
<211> LENGTH: 24
<212> TYPE: DNA
<213> ORGANISM: Artificial Sequence
<220> FEATURE:
<223> OTHER INFORMATION: Synethic primer

<400> SEQUENCE: 26
tgtgtggttg ttggcattgt aggc                                            24

<210> SEQ ID NO 27
<211> LENGTH: 24
<212> TYPE: DNA
<213> ORGANISM: Artificial Sequence
<220> FEATURE:
<223> OTHER INFORMATION: Synethic primer

<400> SEQUENCE: 27
ctcaaagctc agcgtgtcca aaca                                            24

<210> SEQ ID NO 28
<211> LENGTH: 24
<212> TYPE: DNA
<213> ORGANISM: Artificial Sequence
<220> FEATURE:
<223> OTHER INFORMATION: Synethic primer

<400> SEQUENCE: 28
tatcagggtc ttcattgcgg tgga                                            24

<210> SEQ ID NO 29
<211> LENGTH: 22
<212> TYPE: DNA
<213> ORGANISM: Artificial Sequence
<220> FEATURE:
<223> OTHER INFORMATION: Synethic primer

<400> SEQUENCE: 29
cccaagatgg ctgtctcaaa ta                                              22

<210> SEQ ID NO 30
<211> LENGTH: 22
<212> TYPE: DNA
<213> ORGANISM: Artificial Sequence
<220> FEATURE:
<223> OTHER INFORMATION: Synethic primer

<400> SEQUENCE: 30
ggagaggttc ttgtctgtca tc                                              22

<210> SEQ ID NO 31
<211> LENGTH: 22
<212> TYPE: DNA
<213> ORGANISM: Artificial Sequence
<220> FEATURE:
<223> OTHER INFORMATION: Synethic primer

<400> SEQUENCE: 31
ctggtggtgt tcagacagta ac                                              22

<210> SEQ ID NO 32
<211> LENGTH: 22
<212> TYPE: DNA
<213> ORGANISM: Artificial Sequence
<220> FEATURE:
<223> OTHER INFORMATION: Synethic primer

```
<400> SEQUENCE: 32
ctcccactga ataggtgctt tg                                              22

<210> SEQ ID NO 33
<211> LENGTH: 21
<212> TYPE: DNA
<213> ORGANISM: Artificial Sequence
<220> FEATURE:
<223> OTHER INFORMATION: Synethic primer

<400> SEQUENCE: 33
tcgtgatgcc caatctctat g                                               21

<210> SEQ ID NO 34
<211> LENGTH: 22
<212> TYPE: DNA
<213> ORGANISM: Artificial Sequence
<220> FEATURE:
<223> OTHER INFORMATION: Synethic primer

<400> SEQUENCE: 34
catactctgc actgtagctc tc                                              22

<210> SEQ ID NO 35
<211> LENGTH: 22
<212> TYPE: DNA
<213> ORGANISM: Artificial Sequence
<220> FEATURE:
<223> OTHER INFORMATION: Synethic primer

<400> SEQUENCE: 35
cactaccctc agatcacctt tg                                              22

<210> SEQ ID NO 36
<211> LENGTH: 22
<212> TYPE: DNA
<213> ORGANISM: Artificial Sequence
<220> FEATURE:
<223> OTHER INFORMATION: Synethic primer

<400> SEQUENCE: 36
agagattagg catcaccatg ac                                              22

<210> SEQ ID NO 37
<211> LENGTH: 20
<212> TYPE: DNA
<213> ORGANISM: Artificial Sequence
<220> FEATURE:
<223> OTHER INFORMATION: Synethic primer

<400> SEQUENCE: 37
gcgaaagtgg cagagaggta                                                 20

<210> SEQ ID NO 38
<211> LENGTH: 20
<212> TYPE: DNA
<213> ORGANISM: Artificial Sequence
<220> FEATURE:
<223> OTHER INFORMATION: Synethic primer

<400> SEQUENCE: 38
gaggagctgc tgagatgtga                                                 20

<210> SEQ ID NO 39
```

```
<211> LENGTH: 25
<212> TYPE: DNA
<213> ORGANISM: Artificial Sequence
<220> FEATURE:
<223> OTHER INFORMATION: Synethic primer

<400> SEQUENCE: 39
ttttgtgatt tgatttattt ttttt                                       25

<210> SEQ ID NO 40
<211> LENGTH: 26
<212> TYPE: DNA
<213> ORGANISM: Artificial Sequence
<220> FEATURE:
<223> OTHER INFORMATION: Synethic primer

<400> SEQUENCE: 40
atactaataa actcctaaca cccacc                                      26

<210> SEQ ID NO 41
<211> LENGTH: 30
<212> TYPE: DNA
<213> ORGANISM: Artificial Sequence
<220> FEATURE:
<223> OTHER INFORMATION: Synethic primer

<400> SEQUENCE: 41 tatatttta gatgatttgt aaagggtaaa                                   30

<210> SEQ ID NO 42
<211> LENGTH: 30
<212> TYPE: DNA
<213> ORGANISM: Artificial Sequence
<220> FEATURE:
<223> OTHER INFORMATION: Synethic primer

<400> SEQUENCE: 42
atcaacctaa cttataaaaa actaccacat                                  30

<210> SEQ ID NO 43
<211> LENGTH: 25
<212> TYPE: DNA
<213> ORGANISM: Artificial Sequence
<220> FEATURE:
<223> OTHER INFORMATION: Synethic primer

<400> SEQUENCE: 43
tatttttttg ggttttggga tatta                                       25

<210> SEQ ID NO 44
<211> LENGTH: 27
<212> TYPE: DNA
<213> ORGANISM: Artificial Sequence
<220> FEATURE:
<223> OTHER INFORMATION: Synethic primer

<400> SEQUENCE: 44
aaccaaccaa cttcctacac tatctat                                     27

<210> SEQ ID NO 45
<211> LENGTH: 25
<212> TYPE: DNA
<213> ORGANISM: Artificial Sequence
<220> FEATURE:
<223> OTHER INFORMATION: Synethic primer

<400> SEQUENCE: 45
```

```
ttttgggttt ttttggtatt taaga                                        25

<210> SEQ ID NO 46
<211> LENGTH: 25
<212> TYPE: DNA
<213> ORGANISM: Artificial Sequence
<220> FEATURE:
<223> OTHER INFORMATION: Synethic primer

<400> SEQUENCE: 46
ttaaccaaat ttttctacca ttaac                                        25

<210> SEQ ID NO 47
<211> LENGTH: 58
<212> TYPE: DNA
<213> ORGANISM: Artificial Sequence
<220> FEATURE:
<223> OTHER INFORMATION: Synthetic oligonucleotides

<400> SEQUENCE: 47
ccggccacat gagaagacgt ttcttctcga gaagaaacgt cttctcatgt ggtttttg    58

<210> SEQ ID NO 48
<211> LENGTH: 58
<212> TYPE: DNA
<213> ORGANISM: Artificial Sequence
<220> FEATURE:
<223> OTHER INFORMATION: Synthetic oligonucleotides

<400> SEQUENCE: 48
ccgggtcgaa cagaagattg ctaatctcga gattagcaat cttctgttcg acttttttg  58

<210> SEQ ID NO 49
<211> LENGTH: 58
<212> TYPE: DNA
<213> ORGANISM: Artificial Sequence
<220> FEATURE:
<223> OTHER INFORMATION: Synthetic oligonucleotides

<400> SEQUENCE: 49
ccggcctggg cttagaatga gtcttctcga gaagactcat tctaagccca ggtttttg   58

<210> SEQ ID NO 50
<211> LENGTH: 58
<212> TYPE: DNA
<213> ORGANISM: Artificial Sequence
<220> FEATURE:
<223> OTHER INFORMATION: Synthetic oligonucleotides

<400> SEQUENCE: 50
ccgggaagag ttcaagctga agaaactcga gtttcttcag cttgaactct tcttttttg  58
```

METHODS OF TREATING DISEASE BY METABOLIC CONTROL OF T-CELL DIFFERENTIATION

CROSS-REFERENCE

This application is a 35 U.S.C. 371 national stage entry of International Application No. PCT/US17/13252, filed Jan. 12, 2017, which application claims the benefit of U.S. Provisional Patent Application No. 62/279,463, filed Jan. 15, 2016, which applications are incorporated herein by reference in their entireties.

INTRODUCTION

IL-17- and IL-17F-producing CD4 T cells ($T_H17$ cells), though important for host defense against bacterial and fungal infections, have an important pathogenic role in many autoimmune diseases, such as psoriasis, rheumatoid arthritis, multiple sclerosis, and inflammatory bowel diseases (IBD).

Inflammatory reactions in the tumor microenvironment are an important component of the tumor-associated immune response. Inflammatory cells, such as $T_H17$ cells, and the molecules they produce may have crucial roles in initiating and maintaining protective antitumor immunity. The specific nature of the inflammatory response and the tissue context may determine the beneficial versus the detrimental effects of inflammation on tumor pathology.

Regulatory T cells (Treg) cells, derived from either thymus (nTreg cells) or in the periphery (iTreg cells), restrict $T_H17$ cell function through multiple mechanisms. The $T_H17$/Treg balance is usually tightly controlled in vivo to maintain the beneficial role of $T_H17$ cells and limit their detrimental effects. TGF-$\beta$ is required for the differentiation of iTreg cells and $T_H17$ cells in the periphery. At early stages of differentiation, TGF-$\beta$ induces expression of FOXP3 and ROR$\gamma$t, the master transcription factors for Treg and $T_H17$ cells, respectively. Interestingly, inflammatory cytokines, such as IL-6, promote differentiation towards $T_H17$ cells and down-regulate FOXP3 through STAT3. In addition, FOXP3 binds to ROR$\gamma$t and inhibits ROR$\gamma$t-mediated $T_H17$ differentiation, but HIF1$\alpha$ promotes $T_H17$ differentiation by destabilizing FOXP3 and Treg programs.

SUMMARY

Provided herein are methods for treating an individual for a disease (e.g., an autoimmune disease or a cancer) using an active agent which affects metabolism of $\alpha$-ketoglutarate ($\alpha$-KG) and/or 2-hydroxyglutarate (2-HG) in differentiating helper T cells. In some embodiments, an aspartate transaminase 1 (Got1) inhibitor is used to generate a population of T cells enriched in peripheral regulatory T (iTreg) cells, which population of enriched T cells may find use in treating an autoimmune disease. In some embodiments, a tricarboxylic acid (TCA) cycle-associated metabolite, or a derivative thereof, is used to generate a population of T cells enriched for IL-17- and IL-17F-producing CD4 T ($T_H17$) cells, which population of enriched $T_H17$ cells may find use in treating a cancer.

Aspects, including embodiments, of the subject matter described herein may be beneficial alone or in combination, with one or more other aspects or embodiments. Without limiting the description, certain non-limiting aspects of the disclosure numbered 1-61 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of treating an autoimmune disease in an individual, comprising administering to the individual a therapeutically effective amount of an aspartate transaminase 1 (Got1) inhibitor.

2. The method of 1, wherein the therapeutically effective amount is sufficient to increase the ratio of peripheral regulatory T (iTreg) cells to IL-17- and IL-17F-producing helper T ($T_H17$) cells in a population of T cells in the individual, relative to a reference ratio of iTreg cells to $T_H17$ cells in a reference population of T cells.

3. The method of 2, wherein the reference population of T cells is obtained from the individual before the administering.

4. The method of 2, wherein the reference population of T cells is obtained from a cohort of one or more other individuals having or suspected of having the autoimmune disease.

5. The method of 4, wherein the cohort has not been administered with the Got1 inhibitor.

6. The method of any one of 2 to 5, wherein the therapeutically effective amount is sufficient to increase the ratio by 30% or more relative to the reference ratio.

7. The method of any one of 1 to 6, wherein the therapeutically effective amount is sufficient to reduce a proportion of $T_H17$ cells in the population of T cells, relative to a reference proportion of $T_H17$ cells from the reference population of T cells.

8. The method of 7, wherein the therapeutically effective amount is sufficient to reduce the proportion of $T_H17$ cells in the population of T cells by 20% or more.

9. The method of any one of 1 to 8, wherein the method further comprises measuring, in a sample comprising a population of T cells obtained from the individual after the administering:

a first number and/or proportion of $T_H17$ cells in the population; and/or a second number and/or proportion of iTreg cells in the population.

10. The method of 9, wherein the measuring comprises measuring a bulk expression level of, and/or a number of T cells expressing one or more markers for $T_H17$ cells and/or iTreg cells in the population.

11. A method of treating an autoimmune disease in an individual, comprising:

contacting a first population of in vitro differentiating iTreg cells with a Got1 inhibitor in an amount sufficient to promote iTreg differentiation, thereby generating a second population of T cells enriched for iTreg cells compared to a second reference population of T cells derived from a first reference population of differentiating iTreg cells; and administering to the individual a therapeutically effective amount of the second population.

12. The method of 11, wherein the first population and the first reference population are different subpopulations of a common source of T cells.

13. The method of any one of 11 and 12, wherein the first reference population is not contacted with the Got1 inhibitor.

14. The method of any one of 11 to 13, wherein the amount of the Got1 inhibitor is sufficient to provide an increased proportion of iTreg cells in the second population relative to a reference proportion of iTreg cells in the second reference population.

15. The method of 14, wherein the proportion of iTreg cells in the second population is increased by 10% or more.

16. The method of any one of 11 to 15, wherein the first population is an autologous population of differentiating iTreg cells from the individual.

17. The method of 16, wherein the method further comprises obtaining a sample comprising the first population from the individual before the contacting.

18. The method of any one of 1 to 17, wherein the Got1 inhibitor is a small molecule inhibitor or an inhibitory RNA.

19. The method of 18, wherein the Got1 inhibitor is a small molecule inhibitor selected from the group consisting of: aminooxy-acetic acid (AOA), hydroxylamine, L-cycloserine, L-2-amino-4-methoxy-trans-but-3-enoic acid, 2-aminobut-3-enoic acid, and ethyl hydrazinoacetate.

20. The method of 19, wherein the Got1 inhibitor is AOA.

21. The method of any one of 1 to 20, wherein the autoimmune disease is associated with a pathological level of $T_H17$ cells in the individual.

22. The method of any one of 1 to 21, wherein the autoimmune disease is associated with a pathological activity of $T_H17$ cells in the individual.

23. The method of any one of 1 to 22, wherein the autoimmune disease is an inflammatory demyelinating disease.

24. The method of any one of 1 to 20, wherein the autoimmune disease is acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behget's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjogren's syndrome; systemic lupus erythematosus; Takayasu's arteritis; temporal arteritis; vitiligo; warm autoimmune hemolytic anemia; anti myelin-associated glycoprotein (MAG) peripheral neuropathy; Devic's disease; chronic inflammatory demyelinating polyneuropathy or Wegener's granulomatosis.

25. The method of any one of 1 to 24, wherein the method comprises co-administering two or more different treatments for the autoimmune disease.

26. A method of treating a cancer in an individual, comprising administering to the individual a therapeutically effective amount of a tricarboxylic acid (TCA) cycle-associated metabolite, or a derivative thereof, wherein the TCA cycle-associated metabolite is selected from the group consisting of: 2-hydroxyglutarate (2-HG) and α-ketoglutarate (α-KG).

27. The method of 26, wherein the therapeutically effective amount is sufficient to reduce the ratio of iTreg cells to $T_H17$ cells in a population of T cells in the individual, relative to a reference ratio of iTreg cells to $T_H17$ cells in a reference population of T cells.

28. The method of 27, wherein the reference population of T cells is obtained from the individual before the administering.

29. The method of 27, wherein the reference population of T cells is obtained from a cohort of one or more other individuals having or suspected of having the cancer.

30. The method of 29, wherein the cohort has not been administered with the tricarboxylic acid (TCA) cycle-associated metabolite, or derivative thereof.

31. The method of any one of 26 to 30, wherein the therapeutically effective amount is sufficient to reduce the ratio by 10% or more relative to the reference ratio.

32. The method of any one of 27 to 31, wherein the therapeutically effective amount is sufficient to increase a proportion of $T_H17$ cells in the population of T cells, relative to a reference proportion of $T_H17$ from the reference population of T cells.

33. The method of 32, wherein the therapeutically effective amount is sufficient to increase the proportion of $T_H17$ cells in the population by 10% or more.

34. The method of any one of 26 to 33, wherein the method further comprises determining, in a sample comprising a population of T cells obtained from the individual after the administering:

a first number and/or proportion of $T_H17$ cells in the population; and/or a second number and/or proportion of iTreg cells in the population.

35. The method of 34, wherein the determining comprises determining a bulk expression level of, and/or a number of T cells expressing one or more markers for $T_H17$ cells and/or iTreg cells in the population.

36. A method of treating a cancer in an individual, comprising:

contacting a first population of in vitro differentiating $T_H17$ cells with a tricarboxylic acid (TCA) cycle-associated metabolite, or a derivative thereof, in an amount sufficient to promote $T_H17$ cell differentiation, wherein the TCA cycle-associated metabolite is selected from the group consisting of: 2-HG and α-KG, thereby generating a second population of T cells enriched for $T_H17$ cells compared to a second reference population of T cells derived from a first reference population of differentiating $T_H17$ cells; and administering to the individual a therapeutically effective amount of the second population.

37. The method of 36, wherein the first population and the first reference population are different subpopulations of a common source of T cells.

38. The method of any one of 36 and 37, wherein the reference population of T cells is not contacted with the TCA cycle-associated metabolite, or derivative thereof.

39. The method of any one of 36 to 38, wherein the amount of the TCA cycle-associated metabolite, or derivative thereof, is sufficient to reduce the ratio of iTreg cells to $T_H17$ cells by 30% or more relative to a reference ratio of iTreg cells to $T_H17$ cells in the second reference population.

40. The method of any one of 36 to 39, wherein the amount of the TCA cycle-associated metabolite, or derivative thereof, is sufficient to provide an increased proportion of $T_H17$ cells in the second population relative to a reference proportion of $T_H17$ cells in the second reference population.

41. The method of 40, wherein the proportion of $T_H17$ cells in the second population is increased by 10% or more.

42. The method of any one of 36 to 41, wherein the first population is an autologous population of differentiating $T_H17$ cells for the individual.

43. The method of 42, wherein the method further comprises obtaining a sample comprising the first population from the individual before the contacting.

44. The method of any one of 36 to 43, wherein the method further comprises contacting the first population with a tumor-associated antigen.

45. The method of any one of 36 to 43, wherein the first population is a chimeric antigen receptor (CAR)-modified population of differentiating $T_H17$ cells.

46. The method of any one of 36 to 43, wherein the method comprises genetically modifying the first population of a differentiating $T_H17$ cells or the second population of T cells enriched for $T_H17$ cells with a CAR.

47. The method of any one of 26 to 46, wherein the derivative of the TCA cycle-associated metabolite is a dimethyl ester derivative.

48. The method of any one of 26 to 47, wherein the cancer is myeloma, myeloblastic leukemia, promyelocytic leukemia, myclomonocytic, monocytic leukemia, erythroleukemia, Hodgkin's lymphomas, non-Hodgkin's lymphomas, Burkitt's lymphomas, carcinoma, colon carcinoma, small cell lung carcinoma, non-small cell lung carcinoma, adenocarcinoma, melanoma, basal or squamous cell carcinoma, mesothelioma, adenocarcinoma, neuroblastoma, glioma, astrocytoma, medulloblastoma, retinoblastoma, sarcoma, osteosarcoma, rhabdomyosarcoma, fibrosarcoma, osteogenic sarcoma, hepatocellular carcinoma, ovarian carcinoma, pancreatic cancer, renal cell carcinoma or seminoma.

49. The method of any one of 26 to 48, wherein the method comprises co-administering two or more different treatments for the cancer.

50. A method of preparing a population of T cells, the method comprising contacting:
 i) a first population of in vitro differentiating iTreg cells with a Got 1 inhibitor, thereby generating a second population of T cells enriched for iTreg cells relative to a first reference population; or
 ii) a third population of in vitro differentiating $T_H17$ cells with TCA cycle-associated metabolite, or a derivative thereof, wherein the TCA cycle-associated metabolite is selected from the group consisting of: 2-HG and α-KG, thereby generating a fourth population of T cells enriched for $T_H17$ cells relative to a second reference population.

51. The method of 50, wherein the Got1 inhibitor is a small molecule inhibitor or an inhibitory RNA.

52. The method of 51, wherein the Got1 inhibitor is aminooxy-acetic acid (AOA).

53. The method of 50, wherein the derivative of the TCA cycle-associated metabolite is a dimethyl ester derivative.

54. The method of any one of 50 to 53, wherein the first and third populations are autologous populations of T cells.

55. The method of any one of 50 to 54, wherein the first population and the first reference population are different subpopulations of a first common source of T cells, and the third population and the second reference population are different subpopulations of a second common source of T cells.

56. The method of 55, wherein the first or second reference population is not contacted with the Got1 inhibitor or the TCA cycle-associated metabolite, or a derivative thereof.

57. The method of any one of 50 to 56, wherein the second population of T cells is enriched for iTreg cells by 10% or more.

58. The method of any one of 50 to 56, wherein the fourth population of T cells is enriched for $T_H17$ cells by 10% or more.

59. The method of any one of 50 to 58, wherein the third population is a chimeric antigen receptor (CAR)-modified population of differentiating $T_H17$ cells.

60. The method of any one of 50 to 58, wherein the method comprises genetically modifying the third population of differentiating $T_H17$ cells or the fourth population of T cells enriched for $T_H17$ cells with a CAR.

61. The method of any one of 50 to 58, wherein the method further comprises contacting the third population with a tumor-associated antigen.

BRIEF DESCRIPTION OF THE FIGURES

The skilled artisan will understand that the drawings described below are for illustration purposes only. The drawings are not intended to limit the scope of the present teachings in any way.

FIGS. 1a-1h are a collection of plots and graphs showing reprogramming of IL-17- and IL-17F-producing CD4 T ($T_H17$) cell differentiation toward peripheral regulatory T (iTreg) cells by inhibiting Got1 with (aminooxy)-acetic acid (AOA), according to embodiments of the present disclosure.

FIGS. 2a-2g are a collection of plots, graphs and schematic diagrams showing that 2-hydroxyglutarate (2-HG) derived from glutamine/glutamate is highly elevated under $T_H17$-differentiating conditions, and facilitates $T_H17$ cell differentiation, according to embodiments of the present disclosure. For FIG. 2b, each x-axis grouping is from left to right: iTreg, iTreg/AOA, Th17, and Th17/AOA.

FIGS. 3a-3g are a collection of plots and graphs showing that 2-HG promotes $T_H17$ cell differentiation and suppresses iTreg cell differentiation by promoting methylation of the FOXP3 promoter and its intronic CpG island, according to embodiments of the present disclosure.

FIGS. 5a-5b are a collection of plots and schematic diagrams showing that AOA reprograms $T_H17$ cell differentiation toward iTreg cells, according to embodiments of the present disclosure.

FIGS. 7a-7g are a collection of graphs showing representative metabolites from metabolic profiling, according to embodiments of the present disclosure.

FIGS. 8a-8b are a collection of plots showing that exogenously added α-ketoglutarate (α-KG) and 2-HG rescued the effects of AOA on $T_H17$ and iTreg cell differentiation, according to embodiments of the present disclosure.

FIGS. 9a-9d are a collection of plots and graphs showing the effect of cell-permeable metabolites on the differentiation of $T_H17$ or iTreg cells, according to embodiments of the present disclosure.

FIGS. 10a-10d are a collection of graphs showing that differentiating $T_H17$ cells highly expressed isocitrate dehydrogenase (IDH) 1 and IDH2, and that short hairpin RNA (shRNA) directed against IDH1 or IDH2 effectively suppressed the expression of IDH1 or IDH2, according to embodiments of the present disclosure.

FIG. 11 shows an amino acid sequence of human Got1.

DEFINITIONS

Figure 1A:
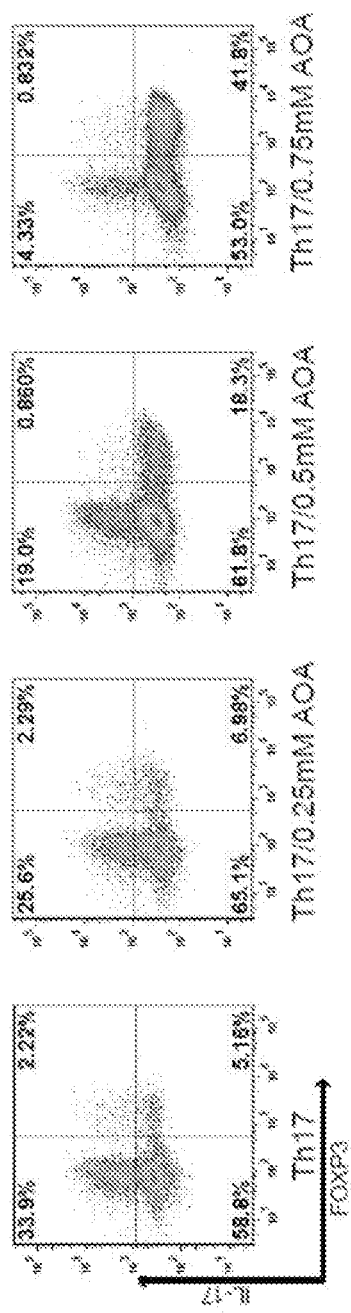

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), short hairpin RNA (shRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST®, used with default parameters. For example, BLAST®N and BLAST®P can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank®+EMBL®+DDBJ+PDB+GenBank® CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., infra; *DNA Cloning*, infra; *Nucleic Acid Hybridization*, infra.

As used herein, the term "individual" refers to any animal, such as a mammal like a dog, cat, bird, livestock, and including a human. In some cases, the individual may be diagnosed with a disease, such as an autoimmune disease or a cancer.

"Autologous" as used herein, may be applied to indicate that an organ, tissue, body fluid or cell used in treating an individual is derived from the same individual.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

A "therapeutically effective amount" or "efficacious amount" means the amount of an agent that, when administered to a mammal or other subject for treating a disease, is sufficient to effect such treatment for the disease. The "therapeutically effective amount" will vary depending on agent, the disease or condition and its severity and the age, weight, etc., of the subject to be treated.

The terms "cancer, "neoplasm," and "tumor" are used interchangeably herein to refer to cells which exhibit relatively autonomous growth, so that they exhibit an aberrant growth phenotype characterized by a significant loss of control of cell proliferation. Cells of interest that may exhibit uncontrolled proliferation include precancerous, malignant, pre-metastatic, metastatic, and non-metastatic cells, as well as carcinoma in situ. Cancer also refers to the pathological condition caused by the uncontrolled proliferation of cells.

"Autoimmune disease" as used herein, refers to a pathological condition, i.e., a disease or disorder, caused by an immune response against a self-tissue or self-tissue component (self-antigen) and may include an antibody response or cell-mediated response.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

"Differentiating $T_H17$ cells" and "differentiating iTreg cells" as used herein, refers to a population of T lymphocytes/T cells that are differentiating and expanding in conditions that promote differentiation into $T_H17$ cells and iTreg cells, respectively. The T cells in the population are T cells that are capable of differentiating into $T_H17$ cells or iTreg cells under the conditions provided. In some cases, the T cells capable of differentiating into $T_H17$ cells or iTreg cells are CD4+ naïve T cells, e.g., CD4+CD25-CD62$^{high}$Cd440$^{low}$ T cells, as determined by a suitable method, e.g., antibody labeling and flow cytometry. Differentiation into $T_H17$ cells or iTreg cells may be determined by measuring the expression level of any suitable markers specific to $T_H17$ cells or iTreg cells. In some cases, $T_H17$ cells are T cells that express IL-17, and iTreg cells are T cells that do not express IL-17. In some cases, iTreg cells are T cells that express FOXP3, and $T_H17$ cells are T cells that do not express FOXP3.

"Enrich", as used herein, may be used to describe a relative increase in size of a first category (e.g., number of elements belonging to the category) over the size of a second category. Enriching may include an increase in the ratio of the first category over the second, an increase in the number of the first category relative to the second category, a decrease in the number of the second category relative to the first category, an increase in the proportion of the first category with respect to a whole (which may be the second category, may include the first and second categories, and/or may include additional categories), a decrease in the proportion of the second category with respect to a whole, and combinations thereof.

"Inhibitory RNA" as used herein refers to an RNA molecule that inhibits or reduces cellular expression (i.e., mRNA and/or protein level) of a target protein in a sequence-specific manner. An inhibitory RNA may be any RNA that can regulate, reduce or inhibit expression of the target protein. An inhibitory RNA may include, without limitation, micro RNA (miRNA; including pri-miRNA and pre-miRNA), small interference RNA (siRNA), or short hairpin RNA (shRNA).

A "derivative" as used herein in relation to a parent compound, include structural variants of the parent compound that have substantially equivalent or greater functional effects as the parent compound.

The term "tumor-associated antigen" as used herein, refers to tumor cells, a homogenate of a tumor, which homogenate may be denatured, or tumor proteins, polypeptides or peptides, e.g. in the form of purified, natural, synthetic and/or recombinant protein, polypeptide or peptide. The tumor-associated antigen may be intact molecules, fragments thereof or multimers or aggregates of intact molecules and/or fragments. Examples of suitable polypeptides and peptides are such that comprises from about 5 to about 30 amino acids, such as, e.g. from about 10 to 25 amino acids, from about 10 to 20 amino acids or from about 12 to 18 amino acids. If peptides are used, a final molar concentration in the culture of from about 0.1 to about 5.0 μM, such as, e.g., from about 0.1 to about 4.0 μM, from about 0.2 to about 3.0 μM, from about 0.3 to about 2.0 μM or from about 0.3 to about 1.0 μM may be used. The tumor-derived antigen may be autologous or heterologous, i.e. arise from the individual to be treated or be obtained from another subject suffering from cancer. In some cases, the tumor-associated antigen is found to be expressed by the tumor at a higher level than the antigen is expressed in a corresponding tissue that is non-tumorous.

"Chimeric antigen receptor (CAR)" as used herein may refer to a cell-surface receptor containing the variable domains of the heavy and the light chain (scFv) of an antibody and a constant region of a T-cell receptor. A CAR may further contain one or more other suitable signaling domains from, e.g., costimulatory proteins, such as CD28, 4-1BB, OX40, ICOS, etc.

The practice of the present disclosure will employ, unless otherwise indicated, conventional methods of medicine, chemistry, biochemistry, immunology, cell biology, molecular biology and recombinant DNA techniques, within the skill of the art. Such techniques are explained fully in the literature. See, e.g., *T Cell Protocols* (Methods in Molecular Biology, G. De Libero ed., Humana Press; 2$^{nd}$ edition, 2009); C. W. Dieffenbach and G. S. Dveksler, *PCR Primer: A Laboratory Manual* (Cold Spring Harbor Laboratory Press; 2$^{nd}$ Lab edition, 2003); *Next Generation Sequencing: Translation to Clinical Diagnostics* (L. C. Wong ed., Springer, 2013); *Deep Sequencing Data Analysis* (Methods in Molecular Biology, N. Shomron ed., Humana Press, 2013); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook et al., *Molecular Cloning: A Laboratory Manual* (3$^{rd}$ Edition, 2001); *Methods In Enzymology* (S. Colowick and N. Kaplan eds., Academic Press, Inc.).

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

DETAILED DESCRIPTION

As summarized above, the present disclosure provides methods for treating an individual for a disease, e.g., an autoimmune disease or a cancer. The present methods involve the use of an active agent which affects metabolism of α-ketoglutarate (α-KG) and/or 2-hydroxyglutarate (2-HG) in differentiating T cells and thereby alters the balance between an IL-17- and IL-17F-producing CD4 T ($T_H17$) cell fate and a peripheral regulatory T (iTreg) cell fate. The active agent may be administered directly to an individual, or may be used to culture a population of T cells to achieve a desired $T_H17$/iTreg balance, which population of T cells may, in some embodiments, then be administered to the individual, where the individual is in need of a shift in the $T_H17$/iTreg balance to treat a disease. Thus, in some cases, the individual may be in need of a reduction in $T_H17$ cells, e.g., to treat an autoimmune disease associated with overactive and/or overrepresentation of auto antigen-recognizing $T_H17$ cells. In some cases, the individual may be in need of an increase in $T_H17$ cells, e.g., to treat a cancer, in which antigens associated with a tumor can be recognized by $T_H17$ cells. Further aspects of the present disclosure are now described.

Active Agents

In some cases, an active agent of the present disclosure is an inhibitor of an aspartate transaminase 1 (Got1), which is a pyridoxal 5'-phosphate (PLP)-dependent transaminase that mediates the interconversion of alpha-amino and alpha-keto acids in a process of reductive amination, in which the redox balance of the reaction is maintained by concomitant conversion of glutamate (the nitrogen donor) into alpha-ketoglutaric acid (α-KG). An inhibitor of Got1 may be used to promote differentiation of naïve T cells into iTreg cells (rather than $T_H17$ cells), thereby increasing the ratio of iTreg to $T_H17$ cells in the population after differentiation. The aspartate transaminase inhibited by the active agent may be from any suitable organism, e.g., mammal, such as, but not limited to, human Got1 (Gene ID: 2805); rat Got1 (Gene ID: 24401); mouse Got1 (Gene ID: 14718); pig Got1 (Gene ID: 396967); or cow Got1 (Gene ID: 281206). In some embodiments, the active agent may be an inhibitor of aspartate transaminase activity in a polypeptide having 80% or more, e.g., 85% or more, 90% or more, 95% or more, 97% or more, and up to 100% amino acid sequence identity to the sequence set forth in SEQ ID NO: 1.

The Got1 inhibitor may be any suitable Got1 inhibitor. In some cases, the Got1 inhibitor is a small molecule inhibitor. The small molecule Got1 inhibitor may inhibit the aspartate transaminase activity in vitro with an $IC_{50}$ of 5.0 mM or less, e.g., 1.0 mM or less, 0.5 mM or less, including 0.1 mM or less. In some cases, the small molecule Got1 inhibitor is a selective inhibitor of Got1, such that the inhibitor has an inhibitory effect on the transaminase activity of Got1 that is greater than the inhibitory effect of the inhibitor on a related transaminase, e.g., alanine transaminase, when compared using comparable conditions. Suitable small molecule inhibitors include, but are not limited to, aminooxyacetic acid (AOA), hydroxylamine, L-cycloserine, L-2-amino-4-methoxy-trans-but-3-enoic acid, 2-aminobut-3-enoic acid (vinylglycine), ethyl hydrazinoacetate, and derivatives thereof.

In some cases, the Got1 inhibitor is an inhibitory RNA, e.g., an siRNA or shRNA specifically targeting Got1 mRNA transcripts. Any suitable method may be used to design the siRNA and/or shRNA based on a Got1 RNA, e.g., mRNA, sequence. Suitable methods are described in, e.g., Ui-Tei et al. (*Nucleic Acids Res.,* 32: 936-948, 2004); Reynolds et al. (*Nat. Biotechnol.,* 22: 326-330, 2004); and Amarzguioui et al. (*Biochem. Biophys. Res. Commun.,* 316: 1050-1058, 2004), which are incorporated herein by reference. In addition, web sites on which siRNA and/or shRNA can be designed have been made available to public by a variety of research institutes or companies, and effective siRNA and/or shRNA can be designed on the web. Representative examples of siRNA and/or shRNA designing web sites include siDirect (design(dot)RNAi(dot)jp/), siSearch (www(dot)epigeneticstation(dot)com/epigenetic-links/detail/link-203 (dot)html), the siDESIGN Center (www(dot)dharmacon (dot)com/designcenter/designcenterpage(dot)aspx), the siRNA Selection Server (jura(dot)wi(dot)mit(dot)edu/bioc/siRNAext/), and the Gene Specific siRNA Selector (bioinfo (dot)wistar(dot)upenn(dot)edu/siRNA/siRNA(dot)htm). In some embodiments, the siRNA may further include other functional nucleic acids, such as RNA aptamers or single-stranded miRNA precursors.

In some embodiments, an active agent of the present disclosure is a tricarboxylic acid (TCA) cycle-associated metabolite, or a derivative thereof, wherein the TCA cycle-associated metabolite is selected from: 2-hydroxyglutarate (2-HG) and α-ketoglutarate (α-KG). A "derivative" of the TCA cycle-associated metabolite may be a compound that is structurally related to the TCA cycle-associated metabolite and that may have substantially equivalent or greater functional effects, with respect to regulating the cell fate of differentiating T cells between the $T_H17$ cell fate and the iTreg cell fate, compared to the parent compound. In some embodiments, the derivative of the TCA cycle-associated metabolite is a membrane-permeable derivative of the TCA cycle-associated metabolite. In some cases, the derivative of the TCA cycle-associated metabolite is a dimethyl ester derivative of the TCA cycle-associated metabolite, e.g., dimethyl-2-HG and dimethyl-α-KG.

Methods of Preparing a Population of T Cells

Also provided herein is a method of preparing a population of T cells in which the $T_H17$/iTreg balance in the population of T cells is controlled to achieve enrichment of $T_H17$ or iTreg cells in the population. The method may include contacting a population of differentiating T cells (e.g., naïve T cells differentiating under $T_H17$ or iTreg differentiating conditions, as described further below) with an active agent that alters the balance between the $T_H17$ cell fate and the iTreg cell fate. The active agent may be a Got1 inhibitor (e.g., AOA), which may promote the iTreg cell fate, or a TCA cycle-associated metabolite, or derivative thereof, which may promote the $T_H17$ cell fate, as described above. The differentiated cells may find use in administering to an individual in need of treatment for a disease, e.g., an autoimmune disease or cancer.

The differentiating population of T cells may be generated by culturing naïve T cells, e.g., CD4+ naïve T cells, under iTreg-promoting or $T_H17$-promoting conditions. CD4+ naïve T cells may be defined by the presence, absence or level of expression of surface markers, such as CD25, CD62 (CD62L), and CD44. The naïve T cells may lack expression of CD25 (CD25-), may have a high level of expression of CD62 ($CD62^{high}$), and may have a low level of expression of CD44 ($CD44^{low}$).

The culturing conditions may be conditions that promote $T_H17$ or iTreg differentiation. Conditions that favor differentiation of $T_H17$ or iTreg from the naïve T cells may include any suitable combination of cytokines, growth factors and cytokine blocking agents (e.g., cytokine-binding antibodies). iTreg differentiation may be promoted by contacting naïve CD4+ T cells with one or more of transforming growth factor (TGF) β, interleukin (L)-2, anti-interferon (IFN) γ antibody, and anti-IL-4 antibody. In some cases, differentiating iTreg cells may be provided by contacting naïve CD4+ T cells with TGFβ and IL-2. In some cases, differentiating iTreg cells may be provided by contacting naïve CD4+ T cells with TGFβ, IL-2, anti-IFNγ antibody and anti-IL-4 antibody. $T_H17$ differentiation may be promoted by contacting naïve CD4+ T cells with one or more of TGFβ, IL-1β, IL-6, IL-23, IL-21, anti-IFNγ antibody and anti-IL-4 antibody. In some cases, differentiating $T_H17$ cells may be provided by contacting naïve CD4+ T cells with TGFβ, IL-1β, IL-6, IL-23 and IL-21. In some cases, differentiating $T_H17$ cells may be provided by contacting naïve CD4+ T cells with TGFβ, IL-1β, IL-6, IL-23, anti-IFNγ antibody and anti-IL-4 antibody.

The naïve T cells that are to be differentiated may be obtained from any suitable source. In some cases, where differentiated T cells are administered to an individual in need, as further described below, the naïve T cells are an autologous population of T cells obtained from the individual who is to be treated. In some cases, the naïve T cells are heterologous to the individual, e.g., obtained from a donor whose naïve T cells are immunologically compatible with the individual to be treated. The naïve T cells may be obtained from a circulating population of T cells, or may be obtained from a population of T cells infiltrating a pathological tissue, e.g., T cells infiltrating a tumor.

The differentiating T cells may be contacted with the active agent for any suitable length of time. In some cases, the differentiating T cells are contacted with the active agent for 3 days or more, e.g., 4 days or more, 5 days or more, including 6 days or more, and, in some embodiments, are contacted with the active agent for 30 days or less, e.g., 21 days or less, 14 days or less, 12 days or less, 10 days or less, including 8 days or less. In some cases, the differentiating T cells are contacted with the active agent for 3 to 30 days, e.g., 3 to 21 days, 4 to 14 days, 4 to 12 days, including 5 to 10 days.

The amount of Got1 inhibitor used to contact a population of differentiating T cells, e.g., differentiating iTreg cells, may vary and may depend on the Got1 inhibitor (e.g., the $IC_{50}$ for Got1 aspartate transaminase activity), the differentiation conditions and the desired enrichment level of iTreg cells in the differentiated population. In some cases, the Got1 inhibitor is provided at 5.0 mM or less, e.g., 1.0 mM or less, 0.5 mM or less, including 0.3 mM or less, and, in some embodiments, is provided at 1.0 nM or more, 10 nM or more, 0.1 μM or more, e.g., 1.0 μM or more, 10 μM or more, including 100 μM or more. In some cases, the Got1 inhibitor is provided in the range of 1.0 nM to 5 mM, e.g., 10 nM to 1.0 mM, 100 nM to 1.0 mM, 1.0 μM to 1.0 mM, 10 μM to 1.0 mM, including 0.1 to 1.0 mM.

The amount of TCA cycle-associated metabolite, or derivative thereof, used to contact a population of differentiating T cells, e.g., differentiating $T_H17$ cells, may vary and may depend on the TCA cycle-associated metabolite, or derivative thereof, the differentiation conditions and the desired enrichment level of $T_H17$ cells in the differentiated population. In some cases, the TCA cycle-associated metabolite, or derivative thereof, is provided at 5.0 mM or less, e.g., 1.0 mM or less, 0.5 mM or less, including 0.3 mM or less, and is provided at 1.0 nM or more, 10 nM or more, 0.1 μM or more, e.g., 1.0 μM or more, 10 μM or more, including 100 μM or more. In some cases, the TCA cycle-associated metabolite, or derivative thereof is provided in the range of 1.0 nM to 5 mM, e.g., 10 nM to 1.0 mM, 100 nM to 1.0 mM, 1.0 μM to 1.0 mM, 10 μM to 1.0 mM, including 0.1 to 1.0 mM.

Any suitable method may be used to prepare a population of T cells for administering to an individual, as described herein, and as described in, e.g., U.S. Pat. Nos. 5,906,936; 8,007,785; PCT Application Pub. Nos. WO 1993/019163; WO 2000/031239; and WO 2003/025126, which are incorporated herein by reference.

Methods of Treating

Provided herein is a method of treating an individual for a disease by administering an active agent, as described above, that can alter the balance between the $T_H17$ cell fate and the iTreg cell fate in a population of differentiating $T_H17$ cells. The method may include administering a therapeutically effective amount of the active agent to treat the disease, e.g., an autoimmune disease or a cancer. Thus the therapeutically effective amount may be sufficient to shift the $T_H17$/iTreg balance that results from differentiation of T cells under $T_H17$-promoting conditions in the individual.

In some cases, the therapeutically effective amount is sufficient to change the ratio of iTreg to $T_H17$ cells in a population of T cells in the individual relative to a reference ratio of iTreg to $T_H17$ cells in a reference population of T cells, i.e., a suitable control population of T cells. Thus, in some cases, the therapeutic effect of the administered amount of the active agent may be defined by comparing the ratio of iTreg to $T_H17$ cells in a first post-administration population of T cells obtained from the individual with the ratio of iTreg to $T_H17$ cells in a second reference population of T cells that provides a baseline measure that at least approximates a pre-administration ratio of iTreg to $T_H17$ cells for the individual.

Thus, in some cases, the reference population is a population of T cells obtained from the individual before administration of the active agent to the individual. Then, the therapeutically effective amount is an amount known to alter the ratio of iTreg to $T_H17$ cells in a population of T cells obtained from the individual after the administering, compared to a reference population that is obtained before the administering but is otherwise obtained and handled in a comparable manner to the population of T cells obtained from the individual after the administering. Thus, in some embodiments, the therapeutic effect of the administered amount of the active agent may be measured by a pre-/post-administration comparison of clinical symptom(s) of the disease.

In some cases, the reference population of T cells may be obtained from a cohort of one or more individuals other than the individual to whom the active agent is being administered, where individuals of the cohort have or are suspected of having the same disease as the individual being treated. In such a case, the T cells from the cohort may be obtained and handled in a similar manner as the T cells obtained from the individual after the administering. In some cases, the active agent has not been administered to the cohort. In some embodiments, a placebo is administered to the cohort. The cohort may be any cohort suitable to serve as a control for the individual being treated, and may be matched by age, ethnicity, sex, type of disease, medical history, etc. Thus, in some embodiments, the therapeutic effect of the administered amount of the active agent may be measured by a comparison of the disease progression in the individual to whom the active agent is administered with the average or typical disease progression in a control cohort of individuals to whom the active agent has not been administered.

In some cases, the method includes measuring the number and/or proportion of $T_H17$ and/or iTreg cells in a sample of T cells obtained from the individual after administering the active agent. The sample may be any suitable sample for assessing the effect of the active agent on the $T_H17$/iTreg balance in the individual. In some cases, the sample is blood, cerebral spinal fluid (CSF), lymph, tissue biopsy, etc. The sample may be analyzed using any suitable method to determine the population makeup of T cells. In some embodiments, the sample is analyzed by counting the number of $T_H17$ and/or iTreg cells which have been detectably labeled for specific markers, measuring the expression level of RNA markers of $T_H17$ and/or iTreg cells, etc. In some embodiments, the sample is analyzed by flow cytometry, microscopy, sequencing (e.g., high-throughput sequencing), polymerase chain reaction (PCR), quantitative PCR (qPCR), reverse transcription (RT)-PCR, etc., to measure the $T_H17$/iTreg balance.

Administering the active agent may be achieved by any suitable method. The routes of administration may be selected according to any of a variety of factors, such as properties of the therapeutic agent(s) to be delivered, the type of condition to be treated (e.g., type of autoimmune disease or cancer), and the like. In some cases, the active agent can be administered by direct injection into a target tissue or into the blood stream, including intradermal, subcutaneous, intravenous, intramuscular, intraosseous, or intraperitoneal injection. The active agents of the present disclosure can be administered by intracerebral, intrathecal, or epidural delivery to tissues of the central nervous system.

Also provided herein is a method of treating an individual for a disease by administering a population of T cells, where the $T_H17$/iTreg balance of the population has been altered in vitro by an active agent, as described above. The active agent may be provided to a differentiating population of T cells in a sufficient amount to generate a differentiated population of T cells, where the proportion of iTreg cells or $T_H17$ in the differentiated population is skewed compared to the proportion in a reference population of T cells cultured under comparable differentiation conditions but in the absence of the active agent.

The reference population may be any suitable population of T cells that can provide an adequate assessment of the change in the $T_H17$/iTreg balance upon differentiation due to the presence of the active agent. In some cases, the reference population is obtained from a different source of naïve T cells than the population of T cells that is contacted with the active agent. In certain embodiments, the population of T cells that is contacted with the active agent is an autologous population of T cells, and the reference population is a population of T cells obtained from a donor, e.g., an immunologically-compatible donor. In some cases, the reference population and the population contacted with the active agent are derived from the same source of naïve T cells, e.g., the same individual. In certain embodiments, the population of T cells that is contacted with the active agent is a first donor-derived population of T cells, and the reference population is a second donor-derived population of T cells, where the first and second donors are different. In certain embodiments, the population of T cells that is contacted with the active agent and the reference population are derived from an autologous population of T cells, obtained by splitting a sample containing T cells from the individual, or obtained from different samples containing T cells from the individual. In certain embodiments, the reference population of T cells is not contacted with the active agent. Otherwise, the population of T cells that is contacted with the active agent and the reference population of T cells may be handled in a similar manner that is sufficient for the reference population to serve as a control for the treated population.

The T cells differentiated in vitro by contacting with an active agent of the present disclosure may be administered to an individual in need, e.g., an individual with an autoimmune disease or cancer, in any convenient manner. The differentiated T cells may be formulated as a pharmaceutical composition suitable for parenteral administration to the individual, e.g., for intravenous, intraarterial, intrathecal, or intraperitonal administration.

Any suitable number of differentiated T cells may be administered to the individual. In some embodiments, the number of differentiated T cells administered to the individual in a single treatment step is $10^5$ cells or more, e.g., $10^6$ cells or more, $10^7$ cells or more, $10^8$ cells or more, including $10^9$ cells or more, and, in some embodiments, may be $10^{12}$ cells or less, e.g., $10^{11}$ cells or less, $10^{10}$ cells or less, including $10^9$ cells or less. In some embodiments, the number of differentiated T cells administered to the individual in a single treatment step is $10^5$ to $10^{12}$ cells, e.g., $10^6$ to $10^{11}$ cells, $10^7$ to $10^{10}$ cells, including $10^8$ to $10^{10}$ cells. Any suitable method may be utilized to administer a population of T cells in accordance with the present disclosure, e.g., systemic intravenous injection and injection directly to the intended site of activity, e.g., a tumor. The preparation can be administered by any convenient route, for example, by infusion or bolus injection and can be administered together with other biologically active agents, e.g., as described herein.

Methods of Treating an Autoimmune Disease

An aspect of the present disclosure includes a method for treating an autoimmune disease in an individual by administering to the individual a therapeutically effective amount of an aspartate transaminase 1 (Got1) inhibitor. The Got1 inhibitor may be any suitable Got1 inhibitor, as described above.

In some cases, the administration of a Got1 inhibitor is sufficient to increase the ratio of iTreg cells to $T_H17$ cells in a population of T cells in the individual, relative to a reference ratio of iTreg cells to $T_H17$ cells in a reference population of T cells. The reference ratio may be any suitable reference ratio that may serve as a baseline for the ratio of iTreg cells to $T_H17$ cells in a population of T cells that may be representative of the autoimmune disease. In some embodiments, the reference ratio is a ratio of iTreg cells to $T_H17$ cells in a reference population of T cells that is a pre-administration population of T cells from the same individual treated for the autoimmune disease and to whom the Got1 inhibitor is administered, as described above. In some embodiments, the reference ratio of iTreg cells to $T_H17$ cells is from a reference population of T cells obtained from a cohort of individuals having or suspected of having the autoimmune disease. In some cases, the active agent that alters the iTreg/$T_H17$ cell balance has not been administered to individuals of the cohort. In some cases, the Got1 inhibitor has not been administered to individuals of the cohort.

In certain embodiments, the administration of a Got1 inhibitor is sufficient to increase the ratio of iTreg cells to $T_H17$ cells in a population of T cells in the individual by 30% or more, e.g., 50% or more, 80% or more, 100% or more, including 150% or more, and, in some embodiments, is sufficient to increase the ratio of iTreg cells to $T_H17$ cells by 400% or less, e.g., 300% or less, 250% or less, 200% including 180% or less, relative to a reference ratio of iTreg cells to $T_H17$ cells in a reference population of T cells. In certain embodiments, the administration of a Got1 inhibitor is sufficient to increase the ratio of iTreg cells to $T_H17$ cells in a population of T cells in the individual by a range of 30 to 400%, e.g., 50 to 300%, 80 to 250%, including 100 to 200%.

In some cases, the administration of the Got1 inhibitor is sufficient to reduce the proportion of $T_H17$ cells in the population of T cells in the individual, relative to a reference proportion of $T_H17$ cells in the reference population of T cells. The reference proportion may be any suitable reference proportion that may serve as a baseline for the proportion of $T_H17$ cells in a population of T cells that may be representative of the autoimmune disease. In some embodiments, the reference proportion is a proportion of $T_H17$ cells in a reference population of T cells, as described above.

In certain embodiments, the administration of a Got1 inhibitor is sufficient to reduce the proportion of $T_H17$ cells in a population of T cells in the individual by 20% or more, e.g., 30% or more, 40% or more, including 50% or more, and, in some embodiments, is sufficient to reduce the proportion of $T_H17$ cells by 90% or less, e.g., 80% or less, e.g., 70% or less, 65% or less, 60% or less, including 55% or less, relative to a reference proportion of $T_H17$ cells in a reference population of T cells. In certain embodiments, the administration of a Got1 inhibitor is sufficient to reduce the proportion of $T_H17$ cells in a population of T cells in the individual by a range of 20 to 90%, e.g., 30 to 80%, 40 to 70%, including 50 to 65%.

Another aspect of the present disclosure includes a method for treating an autoimmune disease in an individual by contacting a first population of in vitro differentiating iTreg cells with a Got1 inhibitor in an amount sufficient to promote iTreg differentiation, thereby generating a second population of T cells enriched for iTreg cells compared to a second reference population of T cells derived from a first reference population of differentiating iTreg cells; and administering to the individual a therapeutically effective amount of the second population.

The reference population may be any suitable reference population that may serve as a baseline for measuring the enrichment of iTreg cells in the second population of T cells. In some cases, the first population and the reference population are subpopulations of a common source of T cells, e.g., a population of T cells obtained from the individual (autologous), or a donor (heterologous). In some embodiments, the reference population may not be contacted with the Got1 inhibitor, but may be handled in similar manner as the first population for the reference population to serve as a control population.

In certain embodiments, the amount of the Got1 inhibitor is sufficient to enrich iTreg cells (i.e., increase the proportion of iTreg cells in the second population), by 10% or more, e.g., 20% or more, 30% or more, 40% or more, including 50% or more, and, in some embodiments, is sufficient to enrich iTreg cells by 100% or less, e.g., 90% or less, 80% or less, 70% or less, including 60% or less. In certain embodiments, the amount of the Got1 inhibitor is sufficient to enrich iTreg cells (i.e., increase the proportion of iTreg cells in the second population), by a range of 10 to 100%, e.g., 20 to 90%, 30 to 80% including 40 to 70%.

In some cases, the proportion of iTreg cells in the second population enriched for iTreg cells is 60% or more, e.g., 70% or more, 75% or more, 80% or more, 85% or more, 90% or more, 95% or more, and up to about 100%.

The autoimmune disease may be any suitable autoimmune disease that is characterized by a pathological level, e.g., pathologically high level, or pathological activity, of $T_H17$ cells in the individual. The pathological level or pathological activity of $T_H17$ cells may be found in any suitable tissue of the individual, such as in the circulating blood, lymph, CSF, an inflamed tissue, etc. The pathological activity may include reactivity toward a self-antigen.

The autoimmune disease may be any suitable autoimmune disease that may be alleviated by increasing the ratio of iTreg cells to $T_H17$ cells. In some cases, the autoimmune disease is acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behget's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjogren's syndrome; systemic lupus erythematosus; Takayasu's arteritis; temporal arteritis; vitiligo; warm autoimmune hemolytic anemia; anti myelin-associated glycoprotein (MAG) peripheral neuropathy; Devic's disease; chronic inflammatory demyelinating polyneuropathy or Wegener's granulomatosis.

In some embodiments, the autoimmune disease may be an inflammatory demyelinating disease. The inflammatory demyelinating disease may include any suitable inflammatory demyelinating disease, such as, but not limited to, acute disseminated encephalomyelitis (ADEM), multiple sclerosis (MS), anti-myelin-associated glycoprotein (MAG) peripheral neuropathy, Devic's disease, Guillain-Barre syndrome (GBS) and chronic inflammatory demyelinating polyneuropathy.

In some cases, the method includes co-administering two or more different treatments for the autoimmune disease, e.g., administering a Got1 inhibitor, or a T cell population enriched for iTreg cells, and one or more other treatments for the autoimmune disease. Any suitable treatment for the autoimmune disease may be co-administered with a treatment of the present disclosure. Suitable treatments include, but are not limited to, administration of immune suppressants (e.g., glucocorticoids, cell division inhibitors, ciclosporin, tacrolimus, sirolimus, interferons, opioids, tumor necrosis factor inhibitors, microphenolates, fingolimod and myriocin, etc.), and radiation therapy.

Methods of Treating a Cancer

Also provided herein is a method of treating a cancer in an individual by administering to the individual a therapeutically effective amount of a tricarboxylic acid (TCA) cycle-associated metabolite, e.g., 2-hydroxyglutarate (2-HG) and α-ketoglutarate (α-KG), or a derivative thereof.

In some cases, administration of the TCA cycle-associated metabolite, or derivative thereof, is sufficient to reduce the ratio of iTreg cells to $T_H17$ cells in a population of T cells in the individual, relative to a reference ratio of iTreg cells to $T_H17$ cells in a reference population of T cells. The reference ratio may be any suitable reference ratio that may serve as a baseline for the ratio of iTreg cells to $T_H17$ cells. In some embodiments, the reference ratio of iTreg cells to $T_H17$ cells is from a reference population of T cells that is a pre-administration population of T cells from the same individual treated for the cancer and to whom the TCA cycle-associated metabolite, or derivative thereof, is administered, as described above. In some embodiments, the reference ratio of iTreg cells to $T_H17$ cells is from a reference population of T cells obtained from a cohort of individuals who have not had an active agent that alters the iTreg/$T_H17$ cell balance administered to them. In some cases, the TCA cycle-associated metabolite, or derivative thereof, has not been administered to individuals of the cohort.

In certain embodiments, the administration of the TCA cycle-associated metabolite, or derivative thereof, is sufficient to reduce the ratio of iTreg cells to $T_H17$ cells in a population of T cells in the individual by 10% or more, e.g., 20% or more, 30% or more, 40% or more, including 50% or more, and, in some embodiments, is sufficient to reduce the ratio of iTreg cells to $T_H17$ cells by 90% or less, e.g., 80% or less, 70% or less, 60% including 50% or less, relative to a reference ratio of iTreg cells to $T_H17$ cells in a reference population of T cells. In certain embodiments, administration of the TCA cycle-associated metabolite, or derivative thereof, is sufficient to reduce the ratio of iTreg cells to $T_H17$ cells in a population of T cells in the individual by a range of 10 to 90%, e.g., 20 to 80%, 30 to 70%, including 40 to 60%.

In some cases, the administration of the TCA cycle-associated metabolite, or derivative thereof, is sufficient to increase the proportion of $T_H17$ cells in a population of T cells in the individual, relative to a reference proportion of $T_H17$ cells in a reference population of T cells. The reference proportion may be any suitable reference proportion that may serve as a baseline for the proportion of $T_H17$ cells. In some embodiments, the reference proportion is from a reference population of T cells, as described above.

In certain embodiments, the administration of the TCA cycle-associated metabolite, or derivative thereof, is sufficient to increase the proportion of $T_H17$ cells in a population of T cells in the individual by 10% or more, e.g., 30% or more, 50% or more, including 80% or more, and, in some embodiments, is sufficient to increase the proportion of $T_H17$ cells by 150% or less, e.g., 120% or less, e.g., 100% or less, 90% or less, 80% or less, relative to a reference proportion of $T_H17$ cells in a reference population of T cells. In certain embodiments, the administration of the TCA cycle-associated metabolite, or derivative thereof, is sufficient to increase the proportion of $T_H17$ cells in a population of T cells in the individual by a range of 10 to 150%, e.g., 30 to 120%, 40 to 120%, including 50 to 100%.

Another aspect of the present disclosure includes a method for treating a cancer in an individual by contacting a first population of in vitro differentiating $T_H17$ cells with a TCA cycle-associated metabolite, or derivative thereof, in an amount sufficient to promote $T_H17$ differentiation, thereby generating a second population of T cells enriched for $T_H17$ cells compared to a second reference population of T cells derived from a first reference population of differentiating $T_H17$ cells; and administering to the individual a therapeutically effective amount of the second population.

The reference population may be any suitable reference population that may serve as a baseline for measuring the enrichment of $T_H17$ cells in the second population of T cells. In some cases, the first population and the reference population are subpopulations of a common source of T cells, e.g., a population of T cells obtained from the individual (autologous), or a donor (heterologous). In some embodiments, the reference population may not have been contacted with the TCA cycle-associated metabolite, or derivative thereof, but may have been handled in similar manner as the first population for the reference population to serve as a control population.

In certain embodiments, the amount of the TCA cycle-associated metabolite, or derivative thereof, is sufficient to enrich $T_H17$ cells (i.e., increase the proportion of $T_H17$ cells in the second population), by 10% or more, e.g., 20% or more, 30% or more, 40% or more, including 50% or more, and, in some embodiments, is sufficient to enrich $T_H17$ cells by 100% or less, e.g., 90% or less, 80% or less, 70% or less, including 60% or less. In certain embodiments, the amount of the TCA cycle-associated metabolite, or derivative thereof, is sufficient to enrich $T_H17$ cells (i.e., increase the proportion of $T_H17$ cells in the second population), by a range of 10 to 100%, e.g., 20 to 90%, 30 to 80% including 40 to 70%.

In some cases, the proportion of $T_H17$ cells in the second population enriched for $T_H17$ cells is 30% or more, e.g., 40% or more, 50% or more, 60% or more, 70% or more, 80% or more, including 90% or more, and, in some embodiments, is 100% or less, e.g., 90% or less, 80% or less, including 70% or less. In some cases, the proportion of $T_H17$ cells in the second population enriched for $T_H17$ cells is in the range of 30 to 100%, e.g., 40 to 90%, including 50 to 80%.

In some embodiments, the method further includes contacting the first population of in vitro differentiating $T_H17$ cells with a tumor-associated antigen, e.g., an antigen known to be associated with the cancer that is to be treated in the individual. The contacting with the tumor-associated antigen may be performed under conditions sufficient to enrich for $T_H17$ cells that are reactive towards the tumor that is being targeted in the individual. Thus, in some cases, the antigen may be an isolated antigen provided in solution. In some cases, the antigen may be presented to the differentiating T cells via an antigen-presenting cell (APC), such as dendritic cells. Any suitable tumor-associated antigen may be used. Examples of suitable tumor-associated antigens and methods for generating T cells targeted for tumor-associated antigens are provided in, e.g., U.S. Pat. Nos. 9,090,940; 8,007,785; 7,906,620; 7,785,801; 7,678,758; PCT App. Pub. No. WO 2015/109180, which are incorporated herein by reference.

In certain embodiments, the differentiating $T_H17$ cells include a genetically modified population of differentiating $T_H17$ cells. In some cases, the differentiating $T_H17$ cells include a chimeric antigen receptor (CAR)-modified population of differentiating $T_H17$ cells. The CAR may be any suitable CAR for, e.g., targeting the $T_H17$ cells differentiated in the presence of the TCA cycle-associated metabolite, or derivative thereof, to a tumor of interest. In some cases, the T cells are genetically modified to express a CAR after differentiating and expanding the $T_H17$ cells in the presence of the TCA cycle-associated metabolite, or derivative thereof. Thus, in some cases, the method includes genetically modifying a population of T cells and contacting the genetically modified population of T cells with the TCA cycle-associated metabolite, or derivative thereof, under $T_H17$ cell differentiating conditions, thereby generating a genetically modified population of CAR-expressing $T_H17$ cells. In some cases, the method includes contacting a population of T cells with the TCA cycle-associated metabolite, or derivative thereof, under $T_H17$ cell differentiating conditions thereby generating a population of differentiated $T_H17$, and genetically modifying the differentiated $T_H17$ cells to express CARs, thereby generating a genetically modified population of CAR-expressing $T_H17$ cells. Any suitable method of generating CAR-modified T cells may be used. Suitable methods are described in, e.g., U.S. Pat. No. 5,906,936; PCT Application Pub. Nos. WO 1993/019163; WO 2000/031239; and WO 2003/025126, which are incorporated herein by reference.

The cancer may be any suitable cancer. Examples of malignancies that may be treated include cancer of the breast, cervix, colon, rectum, endometrium, kidney, lung, ovary, pancreas, prostate gland, skin, stomach, bladder, central nervous system (CNS), esophagus, head-or-neck, liver, testis, thymus or thyroid. Malignancies of blood cells, bone marrow cells, B-lymphocytes, T-lymphocytes, lymphocytic progenitors or myeloid cell progenitors may also be treated. The tumor may be a solid tumor or a non-solid tumor and may be a primary tumor or a disseminated metastatic (secondary) tumor. Non-solid tumors include, without limitation, myeloma; leukemia (acute or chronic, lymphocytic or myelocytic) such as acute myeloblastic, acute promyelocytic, acute myclomonocytic, acute monocytic, erythroleukemia; and lymphomas such as Hodgkin's, non-Hodgkin's and Burkitt's. Solid tumors include, without limitation, carcinoma, colon carcinoma, small cell lung carcinoma, non-small cell lung carcinoma, adenocarcinoma, melanoma, basal or squamous cell carcinoma, mesothelioma, adenocarcinoma, neuroblastoma, glioma, astrocytoma, medulloblastoma, retinoblastoma, sarcoma, osteosarcoma, rhabdomyosarcoma, fibrosarcoma, osteogenic sarcoma, hepatocellular carcinoma, ovarian carcinoma, pancreatic cancer, renal cell carcinoma and seminoma.

In certain embodiments, the present method includes co-administering two or more different treatments for the cancer, e.g., administering a TCA cycle-associated metabolite, or derivative thereof, or a T cell population enriched for $T_H17$ cells, and one or more other treatments for the cancer. Any suitable treatment for the cancer may be co-administered with a treatment of the present disclosure. Suitable treatments include, but are not limited to, administration of pharmaceutical agents, radiation therapy, surgery, etc. Suitable pharmaceutical agents may include chemotherapeutic or anti-cancer agents (for example, including bleomycin, doxorubicin, adriamycin, 5FU, neocarcinostatin, platinum drugs such as cis-platin, taxol, methotrexate, alkylating agents and other agents that produce DNA adducts) or other pharmaceutical agents such as antibiotics, antivirals, anti-inflammatory agents including steroids and NSAIDS, hormones, growth factors, cytokines, antibodies and kinase inhibitors. Thus, in certain embodiments, the present method for treating a cancer may be performed in combination with one or more anti-cancer agents, such as, but not limited tom, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride, temozolomide, carmustine (BCNU), O6-benzylguanine and cisplatin.

Other anti-cancer drugs include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginin deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib, imiquimod; immunostimulant peptides; insulin-like growth factor-1 receptor inhibitor; interferon agonists; interferons; interleukins; iobenguane; iododoxorubicin; ipomeanol, iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human, chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhithxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; spienopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer, bleomycin, bortezomib, oblimersen, remicade, docetaxel, celecoxib, melphalan, dexamethasone, steroids, gemcitabine, temozolomide, etoposide, cyclophosphamide, temodar, carboplatin, procarbazine, gliadel, tamoxifen, topotecan, methotrexate, Arisas, taxol, taxotere, tamoxifen, Gleevec, Herceptin, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin, ganciclovir, adriamycin, estramustine sodium phosphate, sulindac, and etoposide.

In certain embodiments, the pharmaceutical agent co-administered in the present method for treating cancer is administered intravenously or subcutaneously and once or twice daily in an amount of from about 1 to about 1000 mg, from about 5 to about 500 mg, from about 10 to about 350 mg, or from about 50 to about 200 mg. The specific amount of the co-administered pharmaceutical agent may depend on the specific agent used, the type of cancer being treated or managed, the severity and stage of disease, etc.

Pharmaceutically Acceptable Compositions

The active agents of the present disclosure can be formulated as pharmaceutical formulations for treating a disease, e.g., an autoimmune disease or a cancer. Such pharmaceutical compositions may include one or more active agents or pharmaceutically acceptable salt or prodrug thereof (i.e., active substance), and one or more pharmaceutically acceptable carrier/excipient.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., ethylenediaminetetraacetic acid (EDTA) or glutathione), amino acids (such as, e.g., glycine), proteins, disintegrants, binders, lubricants, wetting agents, emulsifiers, sweeteners, colorants, flavorings, aromatisers, thickeners, agents for achieving a depot effect, coatings, antibacterial and antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions may include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

The pharmaceutical compositions may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intraperitoneal or intrasternal injection or infusion), transdermal or transmucosal (such as, e.g., oral, sublingual, intranasal) administration, rectal, vaginal or intra-tracheal instillation, and the like. In this way, the therapeutic effects attainable by the methods and compositions of the present disclosure can be, for example, systemic, local, tissue-specific, etc., depending of the specific needs of a given application of the present disclosure.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be suitably accomplished by uniformly and intimately blending together a suitable amount of the active compound in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the active ingredient with a solid carrier such as described above to provide a mixture having the necessary compression properties, and then compacting the mixture in a suitable machine to the shape and size desired. Moulded tablets maybe made by moulding in a suitable machine, a mixture of powdered compound moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the active agents of the present disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metered-dose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of an active agent of the present disclosure at a concentration of about 0.1 to 3.0 mg/ml. For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium 99 chloride solution, or suitable dispersing or wetting and suspending agents, such as sterile, bland, fixed oils, including synthetic mono- or diglycerides, and fatty acids, including oleic acid. The active agents of the present disclosure can also be lyophilised and the lyophilisates obtained used, for example, for the production of injection or infusion preparations. For example, one illustrative example of a carrier for intravenous use includes a mixture of 10% United States Pharmacopeia (USP) ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may contain one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatide acids, such as dimyristoyl phosphatide acid (DPMA), dipahnitoyl phosphatide acid (DPPA), and distearoyl phosphatide acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). In certain embodiments, a surfactant to active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the active agents according to the present disclosure with a suitable non-irritating excipient, such as cocoa butter, synthetic glyceride esters or polyethylene glycols, which are solid at ordinary temperatures, but liquidity and/or dissolve in the rectal cavity to release the drug.

Suitable carriers for microcapsules, implants or rods are, for example, copolymers of glycolic acid and lactic acid. One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens. In a further modality, a pharmaceutical composition of the disclosure may include, in addition to the active agents as described herein, also one or more other pharmaceutical agents that are suitable in the treatment of the disease, e.g., the autoimmune disease or the cancer.

Without limitation, depending on the type and severity of the disease, a typical daily dosage might range from about 1 µg/kg to 100 mg/kg of body weight or more. For repeated administrations over several days or longer, depending on the condition, the treatment is sustained until a desired suppression of disease symptoms occurs. A preferred dosage of the active agents of the present disclosure may be in the range from about 0.05 mg/kg to about 50 mg/kg of body weight. Thus, one or more doses of about 0.5 mg/kg, 2.0 mg/kg, 4.0 mg/kg or 10 mg/kg (or any combination thereof) may be administered to the individual. Such doses may be administered intermittently, e.g., every week or every three weeks.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Materials and Methods

Reagents and Cell Culture

T cells were cultured in Advanced RPMI (Roswell Park Memorial Institute) 1640 (Invitrogen, #12633) supplemented with 10% fetal bovine serum (FBS) I), penicillin-streptomycin (Invitrogen), 55 µM β-mercaptoethanol, and 2 mM glutamine.

T-Cell Differentiation

CD4 naïve T cells (CD4+CD25-CD62$^{high}$CD44$^{low}$) were obtained from interleukin (IL)-17F-red fluorescent protein (RFP)/FOXP3-green fluorescent protein (GFP) mice, which were characterized previously, or wild-type C57/BL6 mice, by cell sorting. 0.4 million cells were plated into 48 wells coated with anti-mouse CD3 (clone 145-2C11, eBioscience) (2 g/ml) and anti-mouse CD28 (clone 37.51, eBioscience) (1 µg/ml). The differentiation media for these naïve T cells was as follows: 0.5 ng/ml (or indicated) transforming growth factor (TGF) β, 200 U/ml mouse IL-2, 2 µg/ml anti-interferon (IFN) γ and 2 µg/ml anti-mouse IL4 for differentiation into iTreg cells; and 2.5 ng/ml TGFβ, 10 ng/ml mouse IL-1β, 10 ng/ml mouse IL-6, 10 ng/ml mouse IL-23, 2 µg/ml anti-mouse IFNγ, and anti-mouse IL-4 for differentiating into $T_H17$ cells. The cells were supplemented with new medium at day 4. In cases in which small-molecule compounds were present, the fresh medium containing the same concentration of compounds was used. When necessary, the individual metabolite was added into the T-cell culture 6 hours later after initial cell plating. On day 6, the cells were analyzed for IL17F-RFP and FOXP3-GFP or the cells were collected and restimulated for 4-6 hours with PMA, inomycin, and Golgi-stop for intracellular staining in absence of indicated compounds.

mRNA Expression Analysis by qRT-PCR

At the end of differentiation (day 6), T cells were restimulated with plate-coated anti-CD3 and anti-CD28 for 5 hours in the absence of any small-molecule compounds or metabolites. Quantitative reverse transcriptase polymerase chain reaction (qRT-PCR) was performed to evaluate mRNA expression of FOXP3, Il17, Il17f, and Rorc. For differentiating $T_H17$ or iTreg cells, cells were collected on day 2.5 or at the indicated time for mRNA expression analysis. The expression was normalized to β-actin. Primers for qRT-PCR are listed in Table 1.

TABLE 1

| Primer Name | Sequence | SEQ ID NO: |
| --- | --- | --- |
| Got1-F | TCCATCTTTGTCCTCCATGCCTGT | 3 |
| Got1-R | AGATGCAAAGCCCTGATAGGCTGA | 4 |
| Got2-F | TCATCGAGCAGGGCATCAATGTCT | 5 |
| Got2-R | TCTTCAGCTGTGACTCCACCCTTT | 6 |
| GDH-F | TGAAGGAAGCATCTTGGAGGCTGA | 7 |
| GDH-R | CCCATTGGCACCTTCAGCAATGAT | 8 |
| GPT2-F | AACTAACTGATCACGGTGCCTGGT | 9 |
| GPT2-R | TTGCTTGGTGGCTGCTACTTTGTG | 10 |
| GPT1-F | ACAGCCTGGGTGCCTATAGCATTA | 11 |
| GPT1-R | ATATGTTGTTCGGGTCTGCAGGGA | 12 |
| IDH1-F | TGCACACAGTTCCTTCCAAATGGC | 13 |
| IDH1-R | AGCTTGGGCCACCATGTCATCTAT | 14 |
| IDH2-F | CAGCACTGACTGTCCCCAG | 15 |
| IDH2-R | CCTTGATGAACTGCCAGATG | 16 |
| PSAT1-F | GTCCAAGCTGCTATCTGGTATT | 17 |
| PSAT1-R | TCTGATGACCTGTGACTCATTTC | 18 |
| OAT1-F | GAGAGGGAAAGGGTTGCTAAA | 19 |
| OAT1-R | GAAGCCCGTTATCTCGAAGTC | 20 |
| Actin-F | AAATCGTGCGTGACATCAAA | 21 |
| Actin-R | AAGGAAGGCTGGAAAAGAGC | 22 |
| Il17f-F | CAGGAAGACAGCACCATGAA | 23 |
| Il17f-R | TCTTCTCCAACCTGAAGGAATTAG | 24 |
| Rorc-F | AGGCCATTCAGTATGTGGTGGAGT | 25 |
| Rorc-R | TGTGTGGTTGTTGGCATTGTAGGC | 26 |

TABLE 1-continued

| Primer Name | Sequence | SEQ ID NO: |
| --- | --- | --- |
| Il17-F | CTCAAAGCTCAGCGTGTCCAAACA | 27 |
| Il17-R | TATCAGGGTCTTCATTGCGGTGGA | 28 |
| Hot1-F | CCCAAGATGGCTGTCTCAAATA | 29 |
| Hot1-R | GGAGAGGTTCTTGTCTGTCATC | 30 |
| IDH3a-F | CTGGTGGTGTTCAGACAGTAAC | 31 |
| IDH3a-R | CTCCCACTGAATAGGTGCTTTG | 32 |
| IDH3b-F | TCGTGATGCCCAATCTCTATG | 33 |
| IDH3b-R | CATACTCTGCACTGTAGCTCTC | 34 |
| IDH3g-F | CACTACCCTCAGATCACCTTTG | 35 |
| IDH3g-R | AGAGATTAGGCATCACCATGAC | 36 |
| FOXP3-F | GCGAAAGTGGCAGAGAGGTA | 37 |
| FOXP3-R | GAGGAGCTGCTGAGATGTGA | 38 |

Intracellular Metabolomics/Broad Profiling

CD4 naïve T cells, differentiating $T_H17$ cells (day 2.5), and differentiating iTreg cells (day 2.5) were obtained as described above. A solution of 80/20 methanol (MeOH)/$H_2O$ was used to extract intracellular metabolites. The extracted samples were analyzed with liquid chromatography (LC)/mass spectrometry (MS) metabolomics. 200 ng/mL of extraction standard (L-Glutamic acid-$^{13}C5$-$^{15}N$-d5) was added into samples, and the peak value for each metabolite was normalized to extraction standard. The data was transformed into Log 2 and clustered. Cell extracts obtained as described above were analyzed for relative abundance of $^{13}C$ and $^{15}N$ metabolites by liquid chromatography-triple quadrupole mass spectrometry (LC-MS) using scheduled selective reaction monitoring (SRM) for each metabolite of interest, with the detector set to negative mode. Quantitation of intracellular 2-hydroxyglutarate (2HG) was conducted as described previously (Kernesky et al., Blood 2015, 125(2) 296-303).

U-$^{13}C$ Glutamine or $^{15}N$-α-Glutamine Flux Analysis

CD4 naïve T cells, differentiating $T_H17$ or iTreg cells (68 hours) were incubated with fresh media prior to labeling. The cells were then cultured for 4 hours at 37° C. with medium where the glutamine was replaced with the corresponding stable isotope label: 2 mM U-$^{13}C$ glutamine or 2 mM $^{15}N$-α-glutamine for 4 hours at 37° C. The cells were quickly collected and quickly washed with phosphate buffer saline (PBS), pelleted, and snap frozen in liquid nitrogen. The frozen samples were kept in −80° C. until extraction. Cell extracts were prepared by first adding 80/20 MeOH/$H_2O$ at −60° C. to the frozen pellets and collecting the supernatant after centrifugation at 4° C. The extracted samples were analyzed by high-resolution liquid-chromatography-mass spectrometry. Unlabeled glutamine-fed cells were used as background.

For negative mode metabolomics: Cell extracts obtained as described above were analyzed for relative abundance of metabolites by liquid chromatography-triple quadrupole mass spectrometry (LC-MS) using scheduled selective reaction monitoring (SRM) for each metabolite of interest, with the detector set to negative mode. Prior to injection, dried extracts were reconstituted in LC-MS grade water. LC separation was achieved by reverse-phase ion-pairing chromatography.

For amino acid profiling: The ultra-high pressure liquid chromatography (U-HPLC) system consisted of a Thermo Fisher Scientific (San Jose, USA) U-HPLC pumping system, coupled to an autosampler and degasser. Chromatographic separation of the intracellular metabolites was achieved by usage of a reversed phase Atlantis® T3 (3 µm, 2.1 mm ID×150 mm) column (Waters, Eschborn, Germany) and by implementation of a gradient elution program. The elution gradient was carried out with a binary solvent system consisting of 0.1% formic acid and 0.025% heptafluorobutyric acid in water (Solvent A) and in acetonitrile (Solvent B) at a constant flow rate of 400 µL min$^{-1}$. The linear gradient employed was as follows: 0-4 min increase from 0 to 30% B, 4-6 min from 30 to 35% B, 6-6.1 min from 35 to 100% B and hold at 100% B for 5 min, followed by 5 min of re-equilibration. The column oven temperature was maintained at 25° C. and sample volumes of 10 µL were injected. High resolution accurate mass (HRAM) data was acquired using a QExactive™ Orbitrap mass spectrometer (Thermo Fisher Scientific), which was equipped with a heated electrospray ionization source (HESI-II), operated in positive mode. Ionization source working parameters were optimized; the heater temperature was set to 300° C., ion spray voltage was set to 3500 V. An m/z scan range from 70 to 700 was chosen and the resolution was set at 70,000. The automatic gain control (AGC) target was set at 1e$^6$ and the maximum injection time was 250 ms. Instrument control and acquisition was carried out by Xcalibur® 2.2 software (Thermo Fisher Scientific).

Methylation Analysis by Bisulfite Sequencing

The method is essentially the same as described previously (Kim, et al. *J Exp Med* 204 (7), 1543-1551 (2007)). Briefly, genomic DNA was purified with Blood & Cell Culture DNA Midi Kit (Qiagen). Bisufite conversion of genomic DNA was performed using Epitect® bisulfite kit (Qiagen), according to the manufacture's instruction. The primers used to amplify the FOXP3 promoter and its intronic CpG island are listed in Table 2. The PCR product was run on 2% agarose, purified and cloned using TOPO® TA Cloning® Kit with PCR®4. Clones are picked for Sanger sequencing.

TABLE 2

| Primer name | Sequence | SEQ ID NO: |
|---|---|---|
| Outer primer for FOXP3 promoter-F | TTTTGTGATTTGATTTATTTTTTT | 39 |
| Outer primer for FOXP3 promoter-R | ATACTAATAAACTCCTAACACCCACC | 40 |
| Inner primer for FOXP3 promoter-F | TATATTTTTAGATGATTTGTAAAGGGTAAA | 41 |
| Inner primer for FOXP3 promoter-R | ATCAACCTAACTTATAAAAAACTACCACAT | 42 |
| Outer primer for FoxP3 CpG island region-F | TATTTTTTTGGGTTTTGGGATATTA | 43 |
| Outer primer for FoxP3 CpG island region-R | AACCAACCAACTTCCTACACTATCTAT | 44 |
| Inner primer for FoxP3 CpG island region-F | TTTTGGGTTTTTTTGGTATTTAAGA | 45 |
| Inner primer for FoxP3 CpG island region-R | TTAACCAAATTTTTCTACCATTAAC | 46 |

Retrovirus Preparation and T-Cell Infection

Short hairpin RNAs (ShRNAs) (synthesized DNA oligos), after annealing, were cloned into PMKO.1-GFP retrovirus vector. The plasmids and pCL-ECO (1:1) were transfected into 293T cells with Fugene® HD4 (Promega). The medium was changed 6 hours after transfection, and the cells were further cultured for 48-72 hours. The supernatant was then collected and filtered using 45-µm filters. The supernatant containing the viruses was added into pre-activated CD4+ T cells (20 hours after initial plating). The cells were spin-infected at 1000 g for 2 hours and cultured in incubator for another 2 hours. The cells were washed and cultured under $T_H17$ conditions for an additional 4 days. New medium was added if necessary. At day 5, the cells were collected for sorting GFP+ cells and GFP- cells. Sorted cells were further cultured until day 6, and re-stimulated for intracellular staining or mRNA analysis, as described above. Sequences used to generate the shRNAs are listed in Table 3.

TABLE 3

| Oligo Name | Sequence | SEQ ID NO: |
|---|---|---|
| shGot1-1 | CCGGCCACATGAGAAGACGTTTCTTCTCGAGAAGAAACGTCTTCTCATGTGGTTTTTG | 47 |
| shGot1-2 | CCGGGTCGAACAGAAGATTGCTAATCTCGAGATTAGCAATCTTCTGTTCGACTTTTTG | 48 |
| shIDH1 | CCGGCCTGGGCTTAGAATGAGTCTTCTCGAGAAGACTCATTCTAAGCCCAGGTTTTTG | 49 |
| shIDH2 | CCGGGAAGAGTTCAAGCTGAAGAAACTCGAGTTTCTTCAGCTTGAACTCTTCTTTTTG | 50 |

Mouse Experimental Autoimmune Encephalitis (EAE) Model

EAE was induced by immunizing mice (12 weeks old, 11-12 mice/group) twice with 300 μg of MOG35-55 peptide (amino acids 35-55; MEVGWYRSPFSROVHLYRNGK (SEQ ID NO: 2)) emulsified in complete Freund's adjuvant, followed by pertussis toxin injection and analyzed. The disease scores were assigned on a scale of 0-5 as follows: 0, none; 1, limp tail or waddling gait with tail tonicity; 2, wobbly gait; 3, hind limb paralysis; 4, hind limb and forelimb paralysis; 5, death. When the disease phenotype was very obvious (average score>1), PBS or (aminooxy)-acetic acid (AOA) (750 μg/mice) was intraperitoneal (i.p.) injected every day. After 8 days of administration of AOA or PBS, the mice were anesthetized, and cells infiltrated into brain and spinal cord were collected for analysis. When indicated, the statistical significance was determined by Student's t test (*, $p<0.05$; , $p<0.01$; *, $p<0.001$). All animal work was approved by the Institutional Animal Care and Use Committee (IACUC).

Calculations and Statistical Analysis

All in vitro data were repeated at least 2-5 times with consistent results. When indicated, the statistical significance was determined by Student's t test (*, $p<0.05$; , $p<0.01$; *, $p<0.001$).

Chemicals

All the chemicals used in this paper except dimethyl 2-HG were obtained from an external source. Dimethyl (R)-2-HG was synthesized in the lab. The method is as follows:

General Information for Characterization of (R)-dimethyl 2-hydroxyglutarate

Proton nuclear magnetic resonance ($^1$H NMR) spectra were recorded on a Varian Inova® 400 spectrometer at 400 MHz. The chemical shifts are given in parts per million (ppm) on the delta (δ) scale. The solvent peak was used as a reference value (for $^1$H NMR: CDCl$_3$=7.26 ppm). The following abbreviations were used to designate multiplicities: s, singlet; d, doublet; t, triplet; dd, doublet of doublets; m, multiplet. The coupling constant (J) was expressed in Hz.

Synthesis of (R)-dimethyl 2-hydroxyglutarate (R-DM-2-HG)

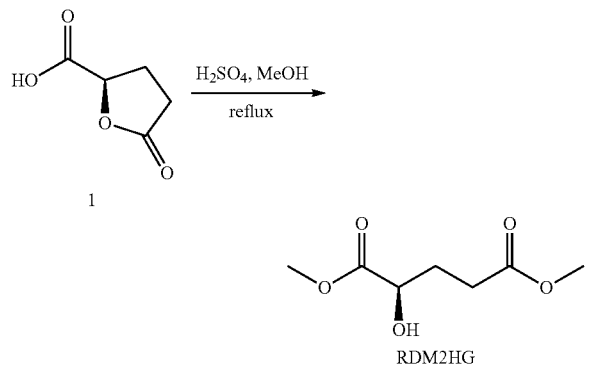

(R)-5-Oxotetrahydrofuran-2-carboxylic acid (1, 1.30 g, 10.0 mmol) was dissolved in 20 mL of methanol, to which 1 mL of concentrated sulfuric acid was added. The resulting solution was refluxed for 12 hours before cooling to room temperature. The cool reaction mixtures were then diluted with dichloromethane and washed consecutively with water, aqueous solution of sodium bicarbonate, and saturated aqueous solution of sodium chloride. The organic layer was dried over anhydrous sodium sulfate. The organic layer was filtered and collected. Concentrated under reduced pressure, the organic layer afforded an oily residue. The residue was taken up in ethyl acetate and filtered through a short plug of silica gel. The filtrate was concentrated under reduced pressure to afford the desired R-DM-2-HG as clear, colorless oil (1.70 g, 97% yield).

$^1$H NMR (400 MHz, CDCl$_3$) δ 4.24 (ddd, J=7.9, 5.3, 4.3 Hz, 1H), 3.80 (s, 3H), 3.68 (s, 3H), 2.86 (d, J=5.4 Hz, 1H), 2.57-2.37 (m, 2H), 2.18 (dddd, J=14.2, 8.1, 7.3, 4.2 Hz, 1H), 1.94 (dtd, J=14.2, 8.0, 6.2 Hz, 1H).

Figure 1B:
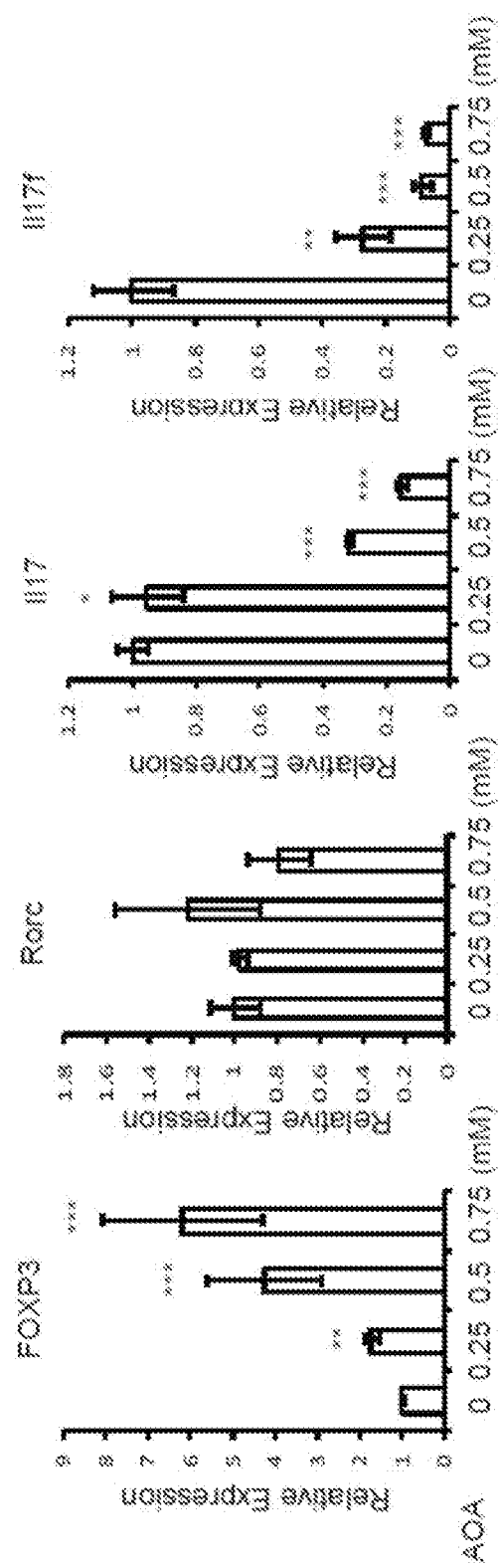

Example 2: Identification of Small Molecules that Regulate Cell-Fate Switching of T$_H$7/iTreg Cells To identify small molecules that regulate cell-fate switching of T$_H$17/iTreg cells and to further understand the regulation of the T$_H$17/iTreg balance, 10,000 individual small molecules were phenotypically screened using CD4 naïve T cells from IL-17F-RFP/FOXP3-GFP mice. The naïve T cells were cultured under optimal T$_H$17 differentiation conditions and compounds that could reprogram T$_H$17 differentiation toward iTreg cell fate were identified using the reporter readout. Briefly, after T$_H$17 differentiation for 24 hours, compounds were added to T$_H$17 culture, and the treatment was continued for an additional 5 days before the cells were analyzed for IL17F-RFP and FOXP3-GFP expression by high-throughput fluorescence-activated cell sorting (FACS) (FIG. 5a). Remarkably, a small molecule, (aminooxy)-acetic acid (AOA), was found to reprogram T$_H$17 induction to iTreg cells in a dose-dependent manner (i.e., suppressing the generation of IL17F expressing cells and inducing FOXP3-expressing cells) (FIG. 5b). This effect of reprogrammed differentiation was further confirmed by intracellular immunostaining of IL-17 and FOXP3 (FIG. 1a). Interestingly, AOA can also dose-dependently promote iTreg cell induction under the iTreg differentiation conditions (FIG. 1c and FIG. 5c), suggesting that AOA may directly regulate FOXP3 expression and the iTreg program. Indeed, AOA selectively reduced the mRNA level of Il17/Il17f, but not Rorc in T$_H$17 cells and promoted transcription of FOXP3 in T$_H$17 and iTreg cells (FIGS. 1b and 1d).

FIGS. 1a-1h. AOA Reprograms T$_H$17 Cell Differentiation Toward iTreg Cells by Inhibiting Aspartate Transaminase 1 (Got1)

(FIG. 1a) AOA reprograms T$_H$17 cell differentiation toward FOXP3+ iTreg T cells. CD4 naïve T cells were differentiated under the optimal T$_H$17 differentiation condition. After a 24-hour T$_H$17 differentiation induction, AOA was added in the culture. At the end of differentiation (day 6), cells were analyzed by intracellular staining of FOXP3 and IL-17. (FIG. 1b) The reprogramed cells described in (FIG. 1a) were analyzed for expression of FOXP3, Rorc, Il17, and Il17f by qRT-PCR. Expression of the indicated genes was normalized to β-actin. (FIG. 1c) AOA can further promote iTreg cell induction under iTreg differentiation conditions in a dose-dependent manner. CD4 naïve T cells were differentiated under iTreg induction conditions. AOA was added into cells after 24 hours. At the end of differentiation, the cells were collected for intracellular staining of FOXP3. (FIG. 1d) The treated cells described in (FIG. 1c) were analyzed for FOXP3 mRNA expression by qRT-PCR. The expression of FOXP3 was normalized to β-actin. (FIG. 1e) Got1 is highly up-regulated in T cells cultured under T$_H$17 differentiation conditions. Relative expression of each transaminase was analyzed in differentiating $T_H17$ cells or iTreg cells (day 3) by qPCR. The expression of the indicated genes was normalized to β-actin, and further plotted as a relative level to β actin-normalized gene expression in iTreg cells. (FIG. 1f) Got1/2 is the major transaminase catalyzing glutamate flux into α-ketoglutarate (α-KG). 2 mM $^{15}$N-α-glutamine was fed to differentiating $T_H17$ cells or iTreg cells (68 hours) for 4 hours. Then, the cells were collected for amino acid analysis. The concentration of $^{15}$N-α-amino acid in molarity was plotted. (FIGS. 1g and 1h) Knockdown of Got1 reduced the percentage of IL17$^+$ cells and reciprocally increased the proportion of FOXP3$^+$ cells. CD4 naïve T cells were differentiated under $T_H17$ differentiation conditions. At 24 hours, the cells were spin-infected with retrovirus containing two different shRNAs targeting GOT1 (GOT1-1 and GOT1-2) or empty vector, PMKO.1-GFP. At day 5, GFP$^+$ cells and GFP− cells were sorted and further cultured under $T_H17$ condition until day 6. Then the cells were analyzed for Got1 expression by qPCR (FIG. 1g) or by intracellular cell staining of FOXP3 and IL-17 (FIG. 1h).

FIGS. 5a-5c. AOA Reprograms $T_H17$ Cell Differentiation Toward iTreg Cells.

(FIG. 5a) Screening procedure showing how the screening was conducted. (FIG. 5b) Effects of AOA on $T_H17$ cell differentiation. Indicated concentrations of AOA were added to differentiating $T_H17$ at 24 hours. Cells were analyzed for IL17F-RFP and FOXP3-GFP on day 6. (FIG. 5c) AOA promoted iTreg cell differentiation. Indicated concentrations of AOA were added to differentiating iTreg cells at 24 hours. The cells were analyzed for IL17F-RFP and FOXP3-GFP on day 5.

Example 3: AOA Reprograms $T_H17$ Cell Differentiation Toward iTreg Cells by Inhibiting Got1

Figure 6A:
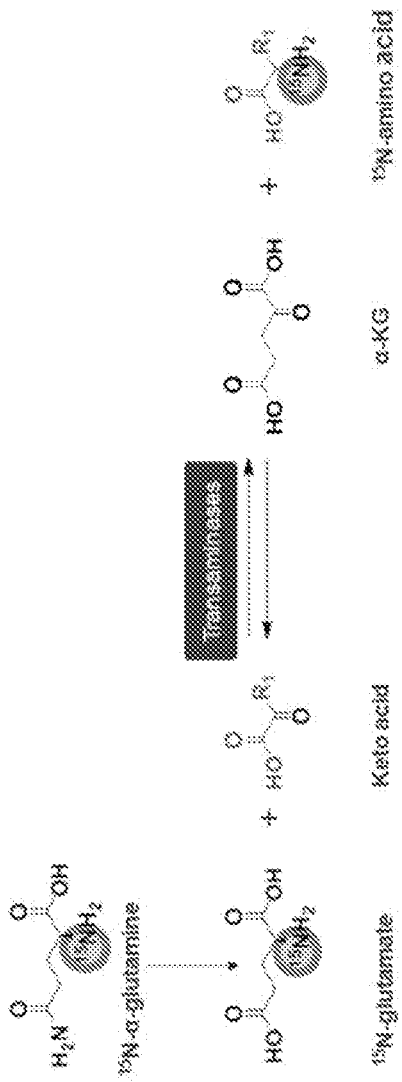
FIGS. 6a-6c are a collection of graphs and diagrams showing that Got1 mediates the majority of transamination in differentiating $T_H17$ cells and iTreg cells, according to embodiments of the present disclosure. For FIG. 6b, each x-axis group is from left to right Th17, Th17+AOA, iTreg, and iTreg+AOA.
Figure 6B:
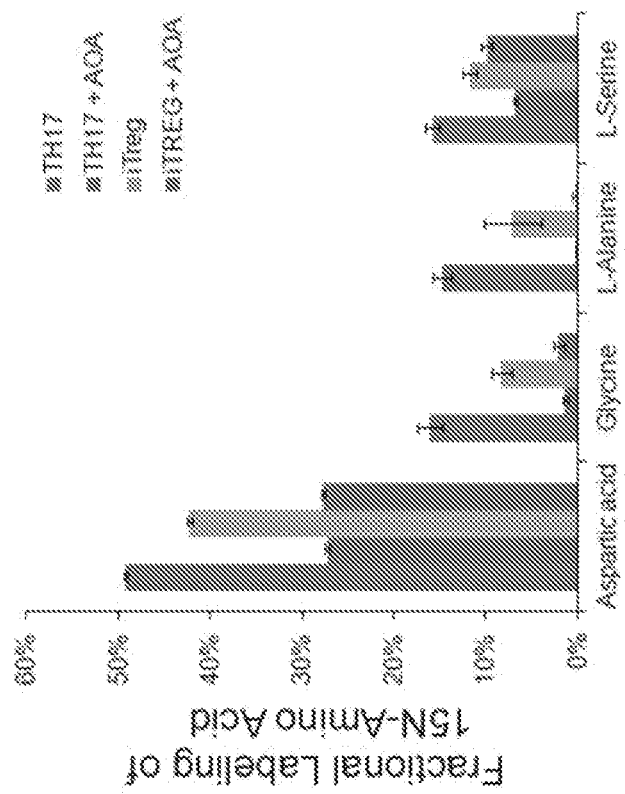
Figure 6C:
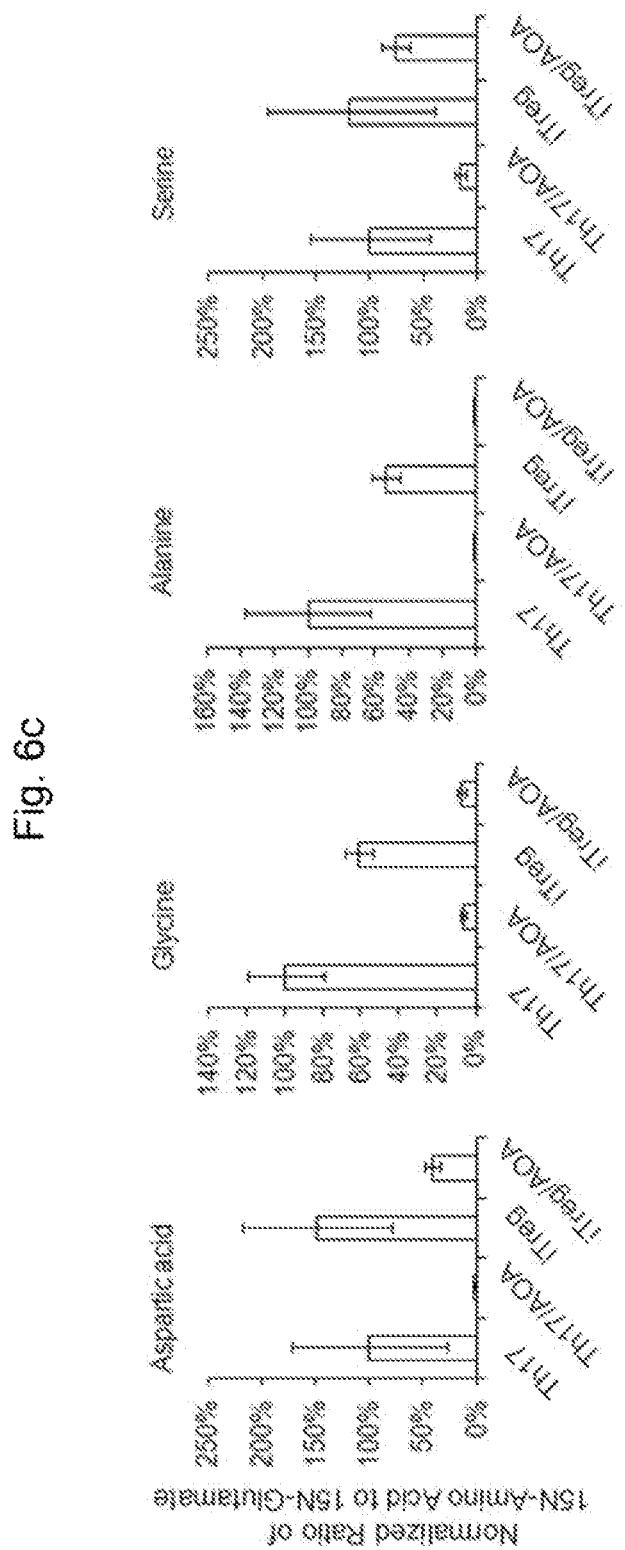

AOA is a known chemical inhibitor of pyridoxal 5'-phosphate (PLP)-dependent transaminases, which mediate the interconversion of alpha-amino and alpha-keto acids in a process of reductive amination, in which the redox balance of the reaction is typically maintained by concomitant conversion of glutamate (the nitrogen donor) into alpha-ketoglutaric acid (α-KG). Thus, the PLP/glutamate-dependent transaminase(s) involved in T-cell differentiation can be deduced by measuring isotopic label accumulation into various amino-acids for differentiating $T_H17$ cells or iTreg cells fed with $^{15}$N-α-glutamine (FIG. 6a). PLP-dependent transaminases include aspartate transaminase 1 and 2 (Got1, Got2), alanine transaminase 1 and 2 (ALT1, ALT2), and several other enzymes involved in amino acid metabolism. To identify the major target of AOA in T-cell differentiation, and determine if $T_H17$ and iTreg cells undergo active yet lineage-distinct transamination processes, T cells differentiated under $T_H17$ or iTreg differentiation conditions were cultured with $^{15}$N-α-glutamine (2 mM) in the medium for 4 hours, and free intracellular $^{15}$N-amino acids were then analyzed by liquid-chromatography-high resolution mass spectrometry (LC/MS). By monitoring de novo synthesis in this manner, it was found that the concentration of $^{15}$N-α-aspartate is 10 fold higher in both differentiating $T_H17$ cells and iTreg cells compared to other detectable $^{15}$N-amino acids (FIG. 1f). Label incorporation into several amino acids was observed and results clearly showed significant decreases for de novo synthesis for several amino acids in both cell types, providing functional evidence of global transamination inhibition with AOA (FIG. 6a-6c). Moreover, ~50% of the total cellular aspartate pool was labeled with $^{15}$N, in contrast to the relatively low fractional labeling for a few other amino acids, including glycine, serine, alanine (<16% of their respective total cellular amino acid pool was $^{15}$N labeled) (FIG. 6b). In addition, the total intracellular $^{15}$N-α-aspartate was reduced by 90% or 75% by AOA treatment in differentiating $T_H17$ cells and iTreg cells, respectively (FIG. 1f). Taken together, the data suggests that a primary fate of the amino group of glutamate in differentiating $T_H17$ cells and iTreg cells was for biosynthesis of aspartic acid catalyzed by GOT1/2, and also that GOT1/2 serves as the major transaminase catalyzing the conversion of glutamate into α-KG in these cells. This analysis revealed that the effects observed with AOA were likely due to alterations in the GOT1/2-mediated reaction. Consistently, expression analysis of glutamate-dependent enzymes by qRT-PCR revealed that Got1 was more highly expressed in $T_H17$ cells than in iTreg cells (FIG. 1e). All other enzymes examined had a similar, relatively low expression in differentiating $T_H17$ cells and iTreg cells (FIG. 1e), further suggesting an important mechanistic link for Got1 activity in the fate determination of $T_H17$ cell differentiation. To genetically confirm its role in T-cell subtype specification, Got1 was knocked down in differentiating $T_H17$ cells with retrovirus containing GFP and shRNA against Got1 (FIG. 1g). Retrovirus-infected GFP+ cells were FACS-sorted for intracellular analysis of FOXP3 and IL-17. Got1 knockdown effectively reproduced the results from AOA treatment by significantly inhibiting the percentage of IL17+ cells and reciprocally increasing the proportion of FOXP3+ cells, compared to control cells infected with control virus or GFP− cells (FIG. 1h).

FIGS. 6a-6c. $^{15}$N-Labeling Analysis Showed that Got1 Mediates the Majority of Transamination.

Figure 2C:
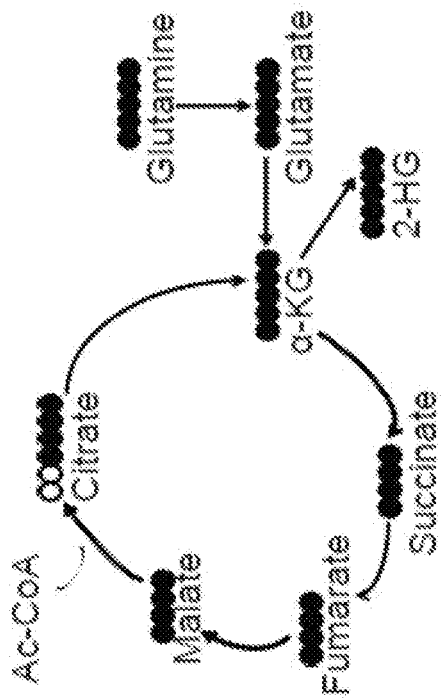

(FIG. 6a) Schematic of how $^{15}$N-α-glutamine was metabolized in the transamination reaction. (FIG. 6b) The ratios of $^{15}$N-labeled amino acids to their respective intracellular amino acid pool (related to FIG. 1f). Differentiating $T_H17$ cells or iTreg cells (day 3) were fed with 2 mM $^{15}$N-α-glutamine for 4 hours. The cells were collected for intracellular metabolites analysis. The ratios of $^{15}$N labeled asparate, glycine, alanine, serine to their total respective amino acid pools were calculated. (FIG. 6c) AOA, as a pan-tranaminase inhibitor, inhibited de novo synthesis for several amino acids (via transamination) in both cell types in addition to asparate. The ratio of $^{15}$N-amino acid to $^{15}$N-glutamate was calculated, and this ratio was further normalized to that in $T_H17$ cells to reflect that AOA inhibited de novo synthesis for several amino acids. Although, AOA indeed inhibited de novo synthesis for several amino acids (via transamination) in both cell types, the rescue results clearly showed (in FIGS. 2f and 2g) that dimethyl α-KG can largely rescued the effect of AOA on both $T_H17$ and iTreg cell differentiation. Thus, from a metabolic perspective, AOA's effect can be largely attributed to its inhibitory effect on α-KG formation (carbon metabolism), rather than its inhibitory effect on amino acid synthesis (nitrogen metabolism). Therefore, focus was on carbon metabolism of glutamate in this study.

Figure 2B:
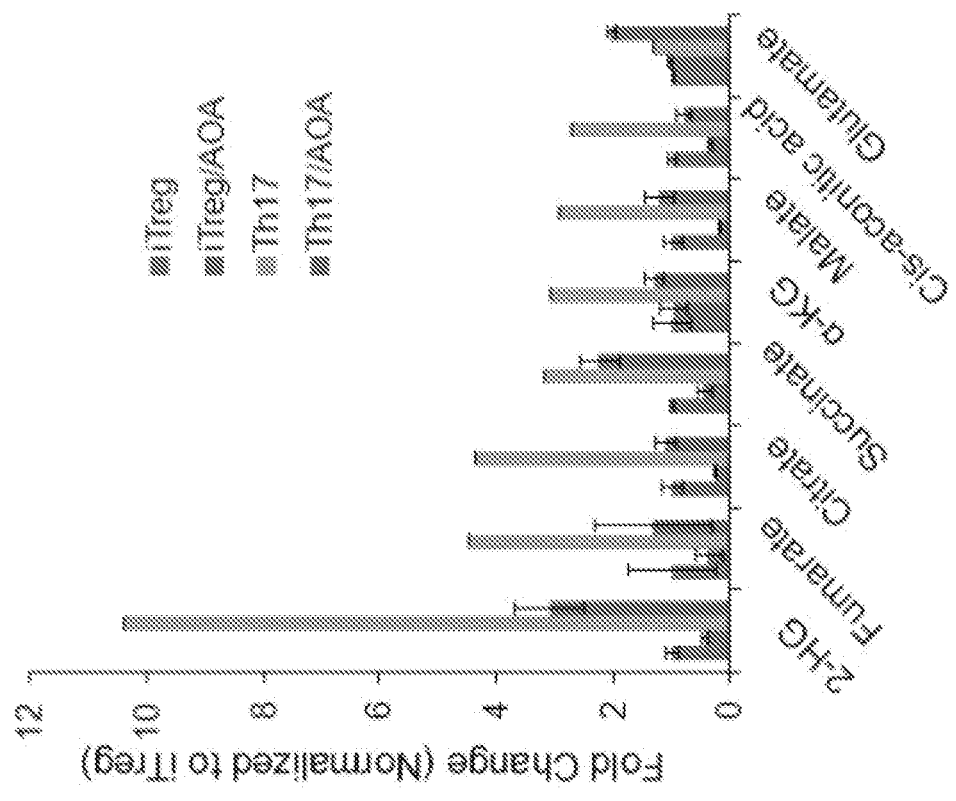

Example 4: 2-HG Derived from Glutamine/Glutamate is Highly Elevated Under $T_H17$ Condition, and Facilitates $T_H17$ Cell Differentiation Various possible metabolic mechanisms by which inhibition of the conversion of glutamate into α-KG by AOA via Got1 inhibition could reprogram differentiating $T_H17$ cells into iTreg cells under $T_H17$ differentiation condition were explored. Intracellular metabolite levels were profiled upon AOA treatment by LC/MS metabolomics in $T_H17$ and iTreg cells at an intermediate timepoint along the differentiation timeline (day 2.5). Differentiating $T_H17$ cells show slight elevation of several tricarboxylic acid (TCA) cycle intermediates, such as α-KG, succinate, fumarate, malate, and citrate, compared to differentiating iTreg cells, and their abundance was reduced partially by AOA in both differentiating conditions (FIGS. 2a, and 2b).

Figures 7B, 7C, 7D:
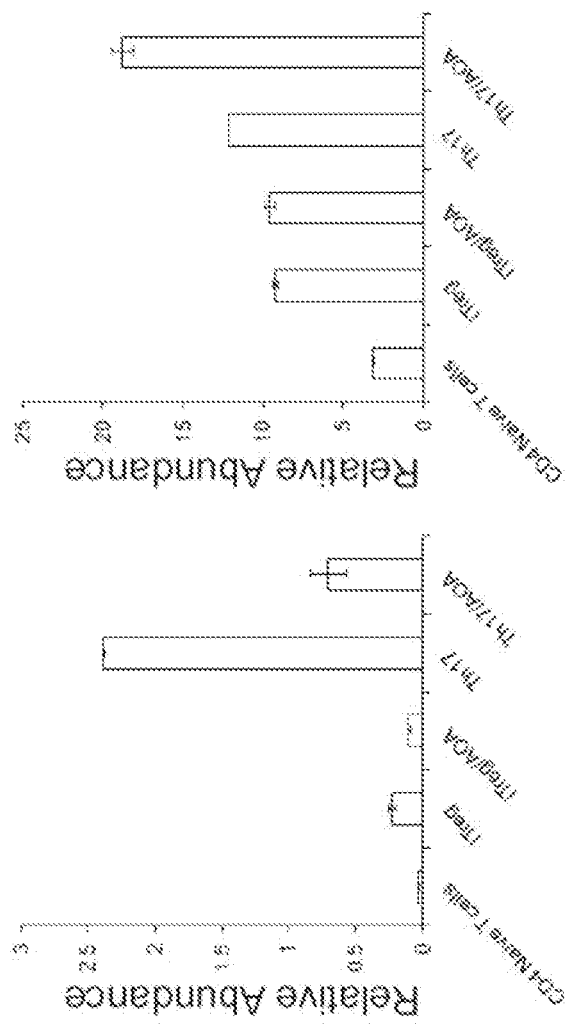
Figure 7E:
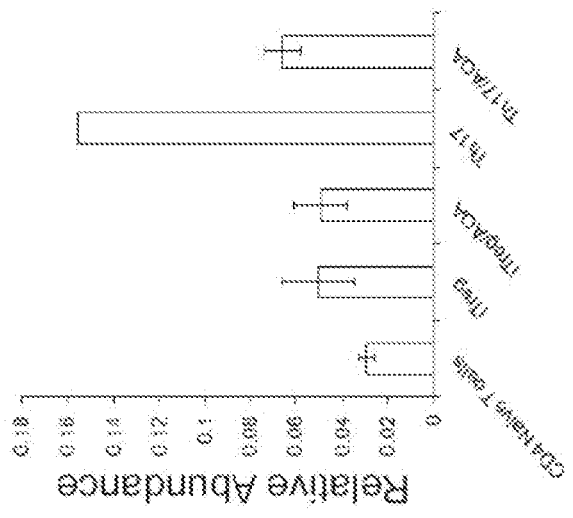
Figure 7F:
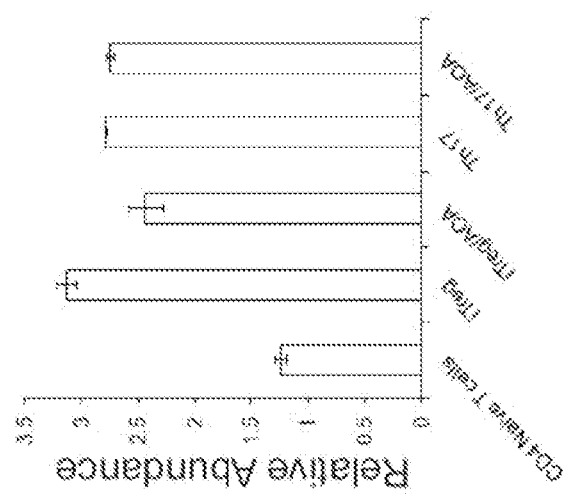
Figure 7G:
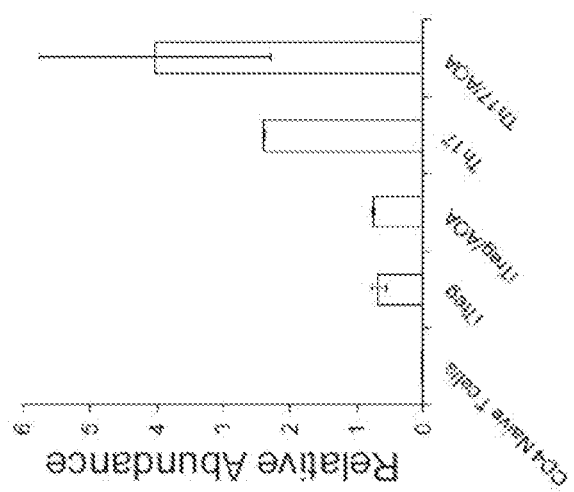

Notably, among all the metabolites detected, 2-hydroxyglutarate (2-HG), which is the direct product of general error-prone dehydrogenase activity on the substrate α-KG, exhibits the most significantly elevated level in $T_H17$ cells relative to iTreg cells. Differentiating $T_H17$ cells maintain ~5-10-fold greater levels of 2-HG compared to iTreg cells along the differentiation timeline (FIGS. 2a, 2b and FIGS. 7a, 7b) with intracellular levels quantitated to be approximately 0.2 mM. Indeed, AOA reduced the steady-state levels of 2-HG by 75% and 50% in differentiating $T_H17$ and iTreg cells, respectively (FIGS. 2a, 2b and FIG. 7b), suggesting that 2-HG synthesized from transamination-driven α-KG in differentiating $T_H17$ and iTreg cells contributes significantly to the total 2-HG pool. The level of glutamate was slightly higher in the presence of AOA in differentiating $T_H17$ and iTreg cells, consistent with Got1 inhibition (FIGS. 2b, and 7c). All other metabolites that were detected either did not show differential abundance between differentiating $T_H17$ and differentiating iTreg cells or were not affected by AOA (FIG. 2a). These data suggested changes in metabolite levels and specifically, 2-HG may have a role in $T_H17$ and iTreg cell subtype specification.

Figure 2D:
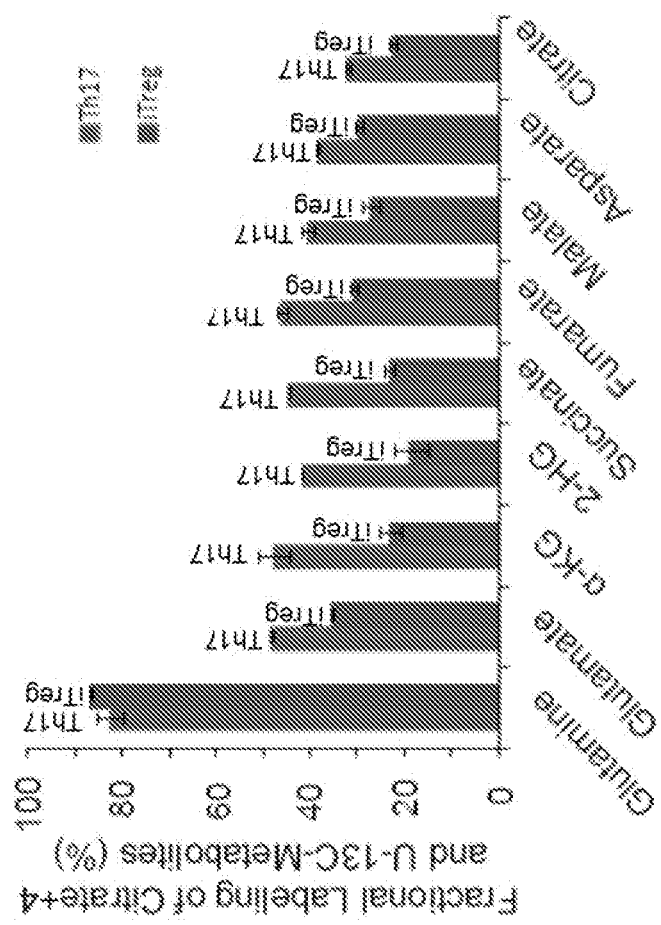
Figure 2E:
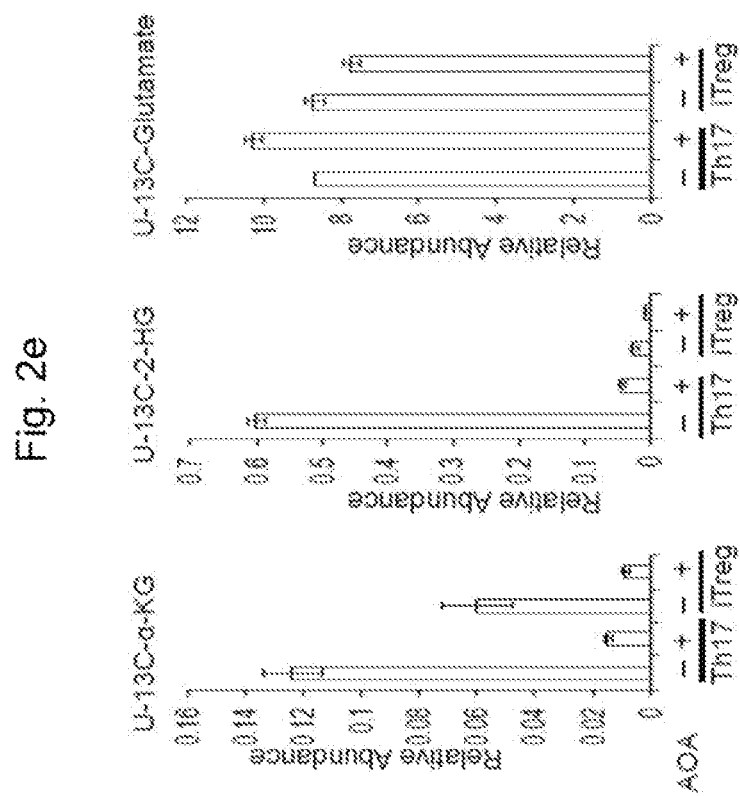
Figure 2F:
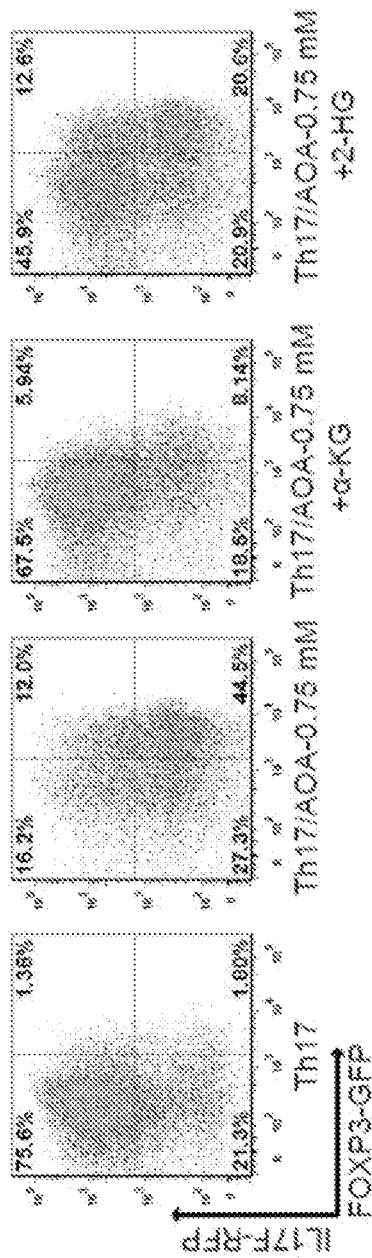

To further confirm a metabolic pathway flow relationship between 2-HG and the upstream inhibition of GOT1 by AOA, experiments were conducted to show that, during differentiation, conversion of total cellular glutamate into α-KG drives altered 2-HG levels. Differentiating $T_H17$ and iTreg cells were cultured with a uniformly $^{13}C$-labeled glutamine ([U-$^{13}C$-Gln]) for 4 hours, as described previously (FIG. 2c); intracellular metabolites and isotopologues were analyzed by LC/MS. With more than 80% of the intracellular glutamine pool labeled, fractional labeling of U-$^{13}C$-2-HG and U-$^{13}C$-α-KG was higher in $T_H17$ cells compared to iTreg cells (~45% of 2-HG and α-KG was U-$^{13}C$-labeled in $T_H17$ cells, while ~20% of them were U-$^{13}C$-labeled in iTreg cells) (FIG. 2d). Notably, a higher percentage of TCA cycle intermediates were $^{13}C$-labeled in differentiating $T_H17$ cells than in iTreg cells (FIG. 2d). These data suggest that more of the glutamine/glutamate carbon contributes to the TCA cycle and 2-HG synthesis in differentiating $T_H17$ cells than in iTreg cells. After normalizing to U-$^{13}C$-glutamine to control the difference in nutrient uptake, newly synthesized 2-HG during the 4-hour labeling time was >30 fold higher in $T_H17$ cells than in iTreg cells, while newly synthesized α-KG is ~three fold higher in $T_H17$ cells than in iTreg cells (FIG. 2e). De novo synthesis of both α-KG and 2-HG in iTreg and $T_H17$ cells was inhibited by AOA, which provides the metabolic confirmation for the decrease in total pool as a function of AOA treatment (FIG. 2e).

To further determine the functional importance of metabolites downstream of glutamate and α-KG in specifying $T_H17$/iTreg cell fate, cell permeable dimethyl esters of α-KG, 2-HG, succinate, fumarate, malate, and citrate (all are decreased by AOA treatment through metabolomics) were individually added to the AOA-containing $T_H17$ culture or iTreg culture conditions to examine whether any of them could rescue AOA-blocked $T_H17$ cell differentiation or reverse AOA-enhanced iTreg differentiation. In addition, glutathione (GSH) and the oxygen radical scavenger N-acetylcysteine (NAC) were also tested individually in the above conditions to determine if production of glutathione and the consequent cellular redox-based mechanism (that is fueled by flux through Got1 in the direction of glutamate production, and inhibited by AOA) could be mediating downstream mechanisms governing $T_H17$ and iTreg differentiation. Among all the metabolites examined, only dimethyl-α-KG (DMKG) and R-2-HG (DMR2-HG) rescued the inhibitory effect of AOA on $T_H17$ differentiation or reversed its enhancing effect on iTreg differentiation (FIGS. 2f, 2g and FIGS. 8a, 8b).

Figure 3A:
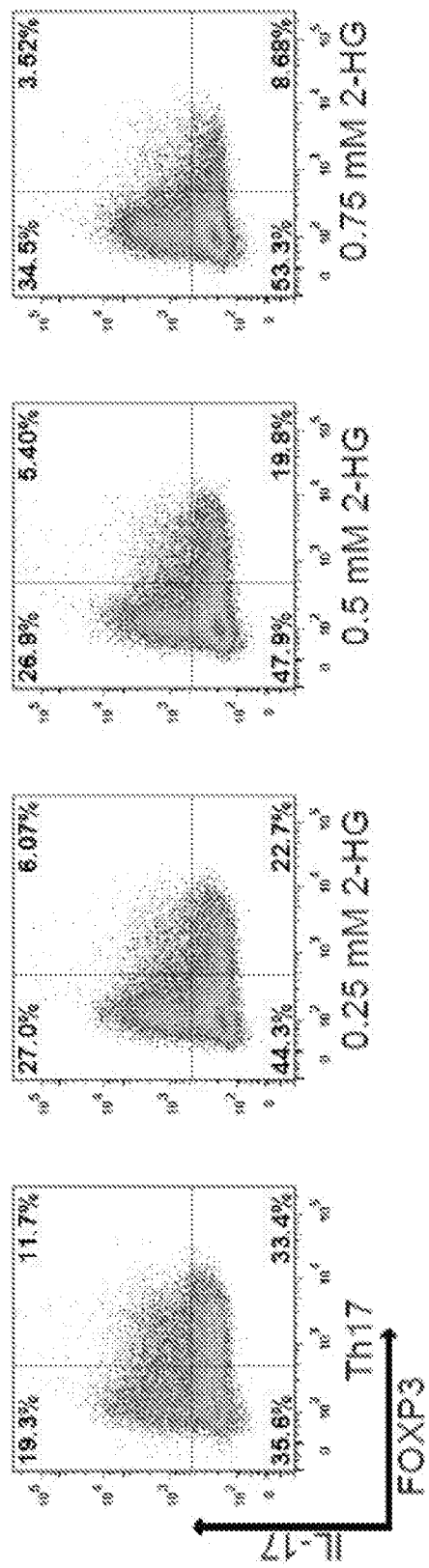
Figure 9B:
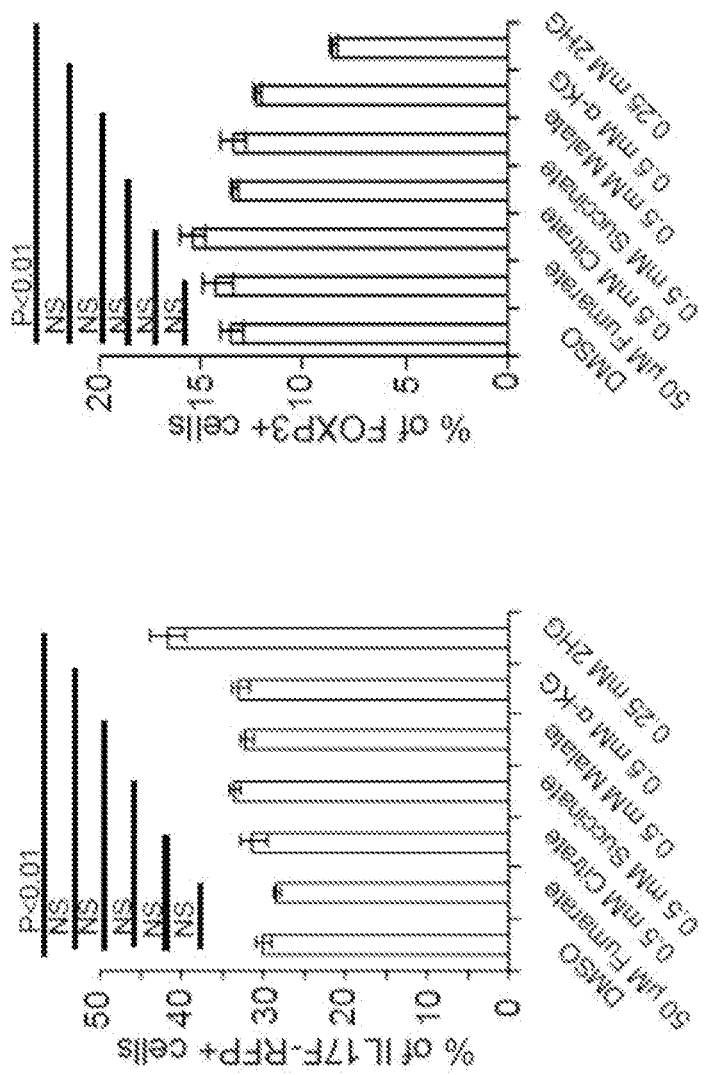

It was also determined if any of these exogenously-added metabolites could directly affect the differentiation of $T_H17$ cell and iTreg cells—in the absence of AOA. Dimethyl R-2-HG, but not α-KG—the precursor of 2-HG, directly promoted $T_H17$ cell differentiation by up-regulating IL-17/IL-17F expression and down-regulating FOXP3 expression in a dose-dependent manner (FIG. 3a and FIG. 9a, 9b). Similarly, dimethyl R-2-HG, but not α-KG inhibited FOXP3 expression under iTreg condition (FIG. 3c, FIG. 9c, 9d)). One possible explanation for the different effects of 2-HG and α-KG in normal $T_H17$ and iTreg differentiation in the absence of AOA is that the generation of 2-HG, but not α-KG, may represent a rate limiting step in glutamate metabolism that dictates the fate of differentiating T cells. These results showed that central carbon metabolism involving α-KG and its downstream metabolites (i.e., 2-HG) is not simply a metabolomics phenomenon, but rather a functional effect of the naïve T-cell specification and its response to AOA.

FIGS. 2a-2g. 2-HG Derived from Glutamine/Glutamate is Highly Elevated Under $T_H17$ Condition, and Facilitates $T_H17$ Cell Differentiation.

Figure 2G:
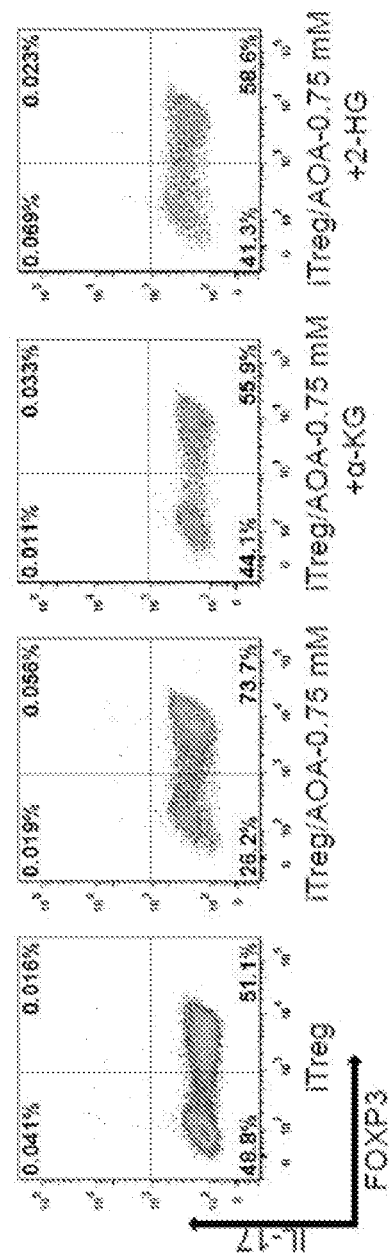

(FIG. 2a) Intracellular metabolite profiling of differentiating $T_H17$ cells and iTreg cells. CD4 naïve T cells, differentiating $T_H17$ cells and iTreg cells (day 2.5) in the absence or presence of 0.5 mM AOA were collected, followed by metabolite extraction. The metabolites were then analyzed by LC/MS. Peak value for each metabolite was normalized to extraction standard, and further transformed into $\log_2$ [metabolite]. Cluster analysis was performed. (FIG. 2b) The relative abundance of significantly changing metabolites from (FIG. 2a) was normalized to that in iTreg cells, and plotted. (FIG. 2c) Schematic of labeling patterns for U-$^{13}C$ glutamine feed for the TCA cycle intermediates. (FIG. 2d) U-$^{13}C$-Glutamine labeling shows that carbon of glutamine enters into TCA cycle and is responsible for 2-HG synthesis. Differentiating $T_H17$ cells or iTreg cells (at 68 hours) were fed with 2 mM U-$^{13}C$-glutamine for 4 hours. The cells were collected for intracellular metabolites analysis by LC/MS. Fractional labeling of U-$^{13}C$-glutamate (glutamate+5), U-13C-α-KG (α-KG+5), succinate+4, fumarate+4, malate+4, and citrate+4 to their respective total intracellular pools were calculated and plotted. (FIG. 2e) The abundance of 2-HG+5 and α-KG+5 was further normalized to intracellular U-$^{13}C$-glutamine to control for the differences in U-$^{13}$C5-glutamine uptake. (FIG. 2f) Exogenously added α-KG and 2-HG rescued the effects of AOA on $T_H17$ cell differentiation. Cell-permeable dimethyl esters of α-KG (0.75 mM) and 2-HG (0.5 mM) were individually added to differentiating $T_H17$ cells in the presence of AOA. At the end of differentiation (day 6), the cells were directly analyzed for FOXP3-GFP and IL17F-RFP. FIG. 2g) Cell-permeable dimethyl esters of α-KG, 2-HG rescued the effects of AOA on iTreg cell differentiation. Cell-permeable dimethyl esters of α-KG (0.5 mM) and 2-HG (0.25 mM) were individually added to differentiating $T_H17$ cells in the presence of AOA. At the end of differentiation (day 5), the cells were analyzed by intracellular staining of FOXP3 and IL-17.

FIGS. 7a-7g. Representative Metabolites from Metabolic Profiling.

(FIG. 7a) 2-HG concentration is much higher in differentiating $T_H17$ cells than iTreg cells along differentiation time line. Differentiating $T_H17$ cells or iTreg cells along differentiation timeline as indicated were collected for intracellular 2-HG measurement. (FIG. 7b) Abundance of 2-HG from FIG. 2a was re-plotted to reflect the relative level of 2-HG in CD4 naïve T cells, differentiating $T_H17$ or iTreg cells (day 2.5) in the absence or presence of AOA. (FIGS. 7c, 7d, 7e, 7f, and 7g) AOA does not affect the level of glutathione, oxidized glutathione, or L-asparate, and slightly decreases α-KG, and slightly increases glutamate. The relative levels of L-glutamate, glutathione, oxidized glutathione, L-asparate and α-KG from FIG. 2a were re-plotted in FIGS. 7c, 7d, 7e, 7f and 7g, respectively.

FIGS. 8a and 8b. Exogenously Added α-KG and 2-HG Rescued the Effects of AOA on $T_H17$ and iTreg Cell Differentiation.

(FIG. 8a), Cell-permeable dimethyl esters of α-KG, 2-HG, but not succinate, fumarate, malate, citrate, N-acetylcysteine (NAC) or glutathione (GSH), rescued the inhibitory effects of AOA on $T_H17$ cell differentiation. Cell-permeable metabolites (0.75 mM α-KG, 0.5 mM 2-HG, 0.5 mM succinate, 50 μM fumarate, 0.5 mM malate, 0.5 mM citrate, 1 mM NAC, and 1 mM GSH) were individually added to differentiating $T_H17$ cells in the presence of AOA. At the end of differentiation (day 6), the cells were re-stimulated and analyzed by intracellular staining of FOXP3 and IL-17. FIG. 8b) Cell-permeable dimethyl esters of α-KG, 2-HG, but not succinate, fumarate, malate or citrate rescued the effects of AOA on iTreg cell differentiation. Cell permeable metabolites (0.5 mM α-KG, 0.125 mM 2-HG, 0.5 mM succinate, 50 μM fumarate, 0.5 mM malate, 0.5 mM citrate) were individually added to differentiating iTreg cells in the presence of AOA. At the end of differentiation (day 5), the cells were directly analyzed for FOXP3-GFP and L17F-RFP.

FIGS. 9A-9D. The Effect of Cell-Permeable Metabolites (α-KG, 2-HG, Citrate, Succinate, Fumarate, Malate) on the Differentiation of $T_H17$ or iTreg Cells.

(FIG. 9a) The indicated dimethyl metabolites were added into $T_H17$ culture, and the cells were analyzed on day 3. (FIG. 9b) The percentages of L17F-RFP+FOXP3– cells and FOXP3+IL17F-RFP– were plotted. (FIG. 9c) The indicated metabolites were added into iTreg culture, and the cells were analyzed on day 5. (FIG. 9d) The percentages of FOXP3+ cells were plotted.

Figure 4B:
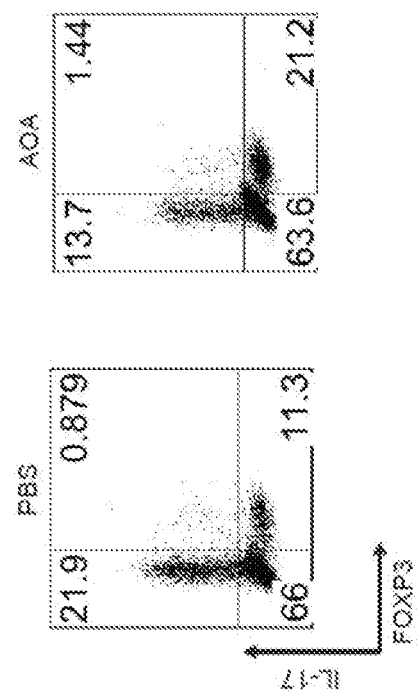
FIGS. 4a-4d are a collection of plots, graphs and schematic diagrams showing that AOA produced a significant recovery from experimental autoimmune encephalomyelitis (EAE) diseases, according to embodiments of the present disclosure.
Figure 10D:
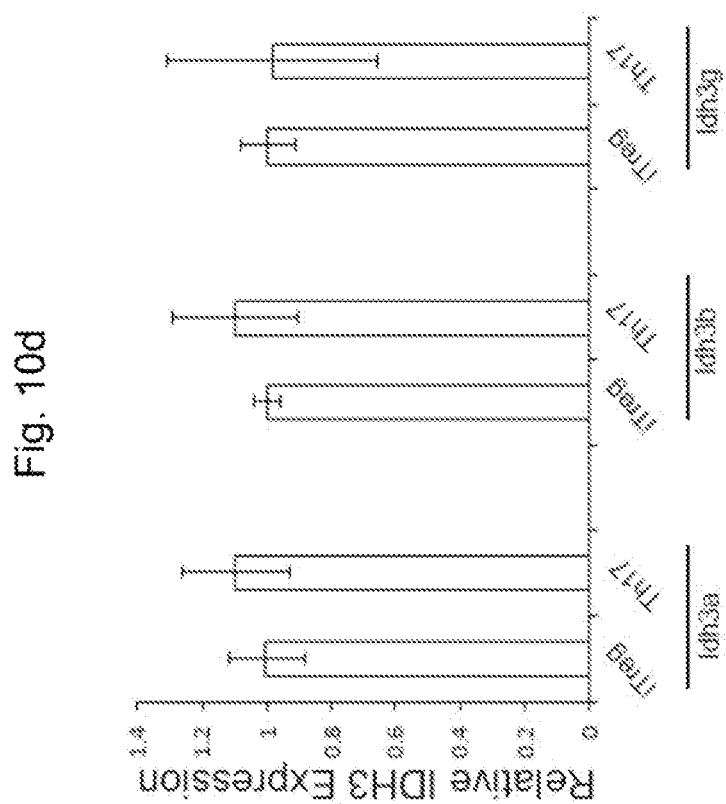

Example 5: 2-HG Promotes $T_H17$ Cell Differentiation and Suppresses iTreg Cell Differentiation by Promoting Methylation of the FOXP3 Promoter and its Intronic CpG Island 2-HG, which was originally identified in cancer cells harboring isocitrate dehydrogenase (IDH) 1/2 mutation, is also known to be produced via wild-type IDH1 and IDH2 reactions as well. Among all the dehydrogenases examined in this study, only IDH1 and 2 are highly expressed in differentiating $T_H17$ cells (FIGS. 10a, 10d). It was therefore hypothesized that IDH1/2 generate 2-HG during T-cell specification and consequently affects T-cell fate determination. To test this, IDH1 and IDH2 were knocked down individually or together in T cells cultured under $T_H17$ condition by retrovirus expressing GFP and shRNAs against IDH1 and IDH2. GFP+ cells and GFP– cells were sorted and analyzed by intracellular staining of IL-17 and FOXP3. As expected, knockdown of IDH1 or IDH2 reduced the percentage of IL-17 producing cells by approximately 30%, while double knockdown of IDH1 and IDH2 reduced the percentage of IL-17 producing cells by more than 50%, and reciprocally increased the percentage of iTreg cells by threefold (FIG. 4g). The data thus suggest that α-KG/2-HG accumulated under $T_H17$ differentiation conditions promote $T_H17$ cell differentiation.

Figure 3B:
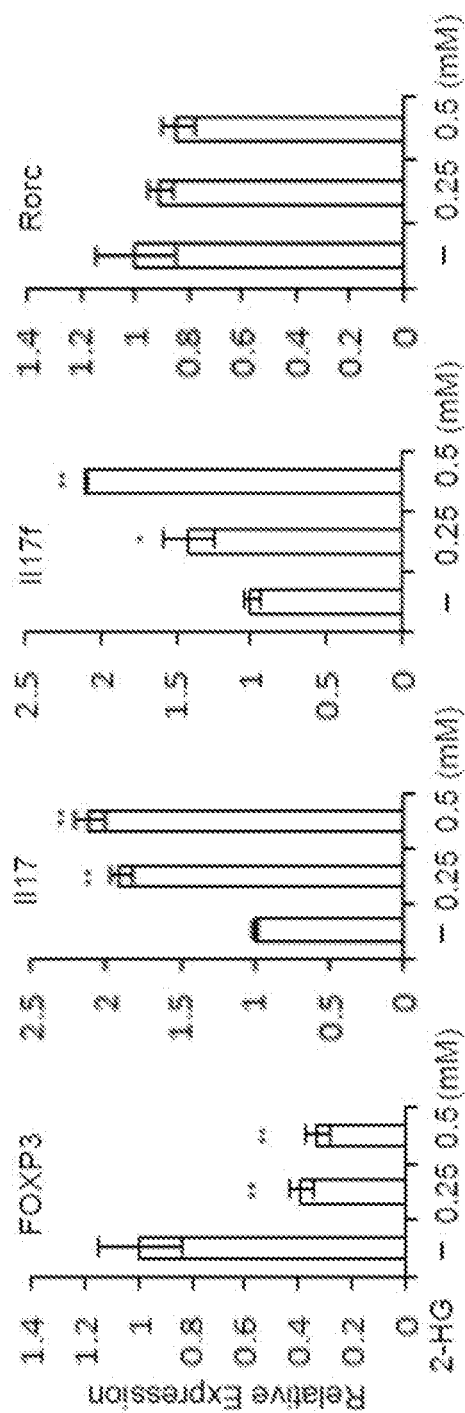

To further characterize the mechanism by which R-2-HG mediates $T_H17$ cell specification, the effects of R-2-HG on expression of FOXP3 and RORγt, two master transcription factors governing iTreg and $T_H17$ fate, respectively, were examined. Interestingly, R-2-HG suppressed FOXP3 mRNA expression in both differentiating $T_H17$ cells and iTreg cells, and increased Il17/Il17f mRNA, but did not affect Rorc mRNA in differentiating $T_H17$ cells (FIGS. 3b and 3d). R-2HG functions as an antagonist for many α-KG-dependent dioxygenases, such as Tet family enzymes and histone demethylases, which can regulate gene expression through DNA demethylation and histone demethylation, respectively. FOXP3 binds to RORγt and inhibit RORγt-directed $T_H17$ differention; therefore, R-2-HG might promote $T_H17$ differentiation through its inhibitory effect on FOXP3 transcription. The methylation status of the FOXP3 promoter and its intronic CpG island, located in the conserved non-coding sequence 2 (CNS2), controls the expression of FOXP3. Tet proteins function in DNA demethylation, and Tet1/2 are highly enriched in the FOXP3 promoter and its intronic CpG island in peripheral Treg cells, and are therefore important for maintaining the unmethylated (or partially methylated) state of this region.

Figure 3F:
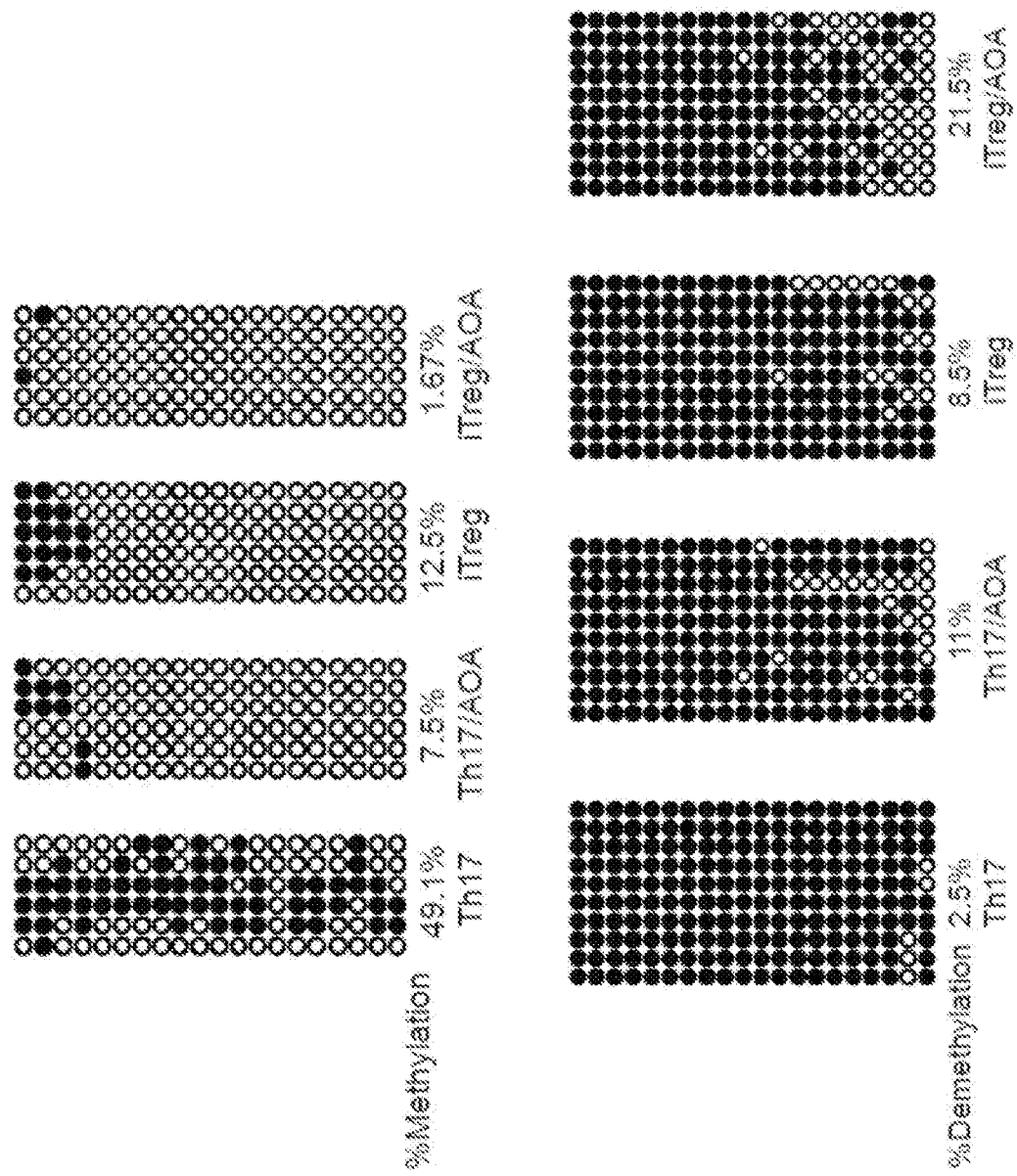

Intrigued by the role of R-2-HG in suppressing FOXP3 gene expression and its ability to inhibit Tet family enzymes, the methylation status of the FOXP3 promoter and CpG island was examined by bisulfite sequencing in $T_H17$ cells and iTreg cells. In agreement with previous studies, the FOXP3 promoter is hypomethylated in iTreg cells, and its intronic CpG island exhibits partial DNA demethylation in iTreg cells. Surprisingly, it was found that these regions are also hypomethylated in differentiating $T_H17$ cells, very similar to iTreg cells, but are hypermethylated in fully differentiated $T_H17$ cells (FIG. 3e). Strikingly, R-2-HG can dramatically increase methylation level of these regions in both differentiating $T_H17$ cells and iTreg cells (FIG. 3e), which explains the observed reduction of FOXP3 transcription in both differentiation conditions (FIGS. 3b and 3d). To further connect AOA's effect on licensing an iTreg cell phenotype with the reduction of glutamate-derived 2-HG and subsequent decreased DNA methylation, the methylation levels of FOXP3 promoter and its intronic CpG island under $T_H17$ condition and iTreg condition were also examined by bisulfite sequencing. Consistent with the hypothesis, AOA treatment dramatically decreased the methylation levels at FOXP3 gene locus in both $T_H17$ and iTreg cultures (FIG. 3f).

FIGS. 3a-3g. 2-HG Promotes $T_H17$ Cell Differentiation and Suppresses iTreg Cell Differentiation by Promoting Methylation of the FOXP3 Promoter and its Intronic CpG Island.

(FIG. 3a) Exogenous addition of dimethyl R-2-HG promoted $T_H17$ cell differentiation. Dimethyl R-2-HG at the indicated concentrations was added to differentiating $T_H17$ cells for four days, and the cells were analyzed for FOXP3 and IL-17 expression by FACS via intracellular staining. (FIG. 3b) Exogenous addition of dimethyl R-2-HG increased Il17/Il17f mRNA, but not Rorc, and decreased FOXP3 mRNA. $T_H17$ cells were differentiated in the presence of R-2-HG for 4 days. The cells were then re-stimulated with anti-CD3 and anti-CD28 for 5 hours. mRNA expression of FOXP3, Rorc, Il17, or Il17f was analyzed by qRT-PCR. (FIG. 3c) 2-HG inhibited iTreg cell differentiation. iTreg cells were differentiated in the presence of R-2-HG. The cells were analyzed on day 5 for FOXP3-GFP and IL17F-RFP. (FIG. 3d) Exogenous addition of dimethyl R-2-HG decreased FOXP3 mRNA under iTreg condition. iTreg cells were differentiated in presence of indicated concentration of dimethyl R-2-HG for 5 days, the cells were then analyzed for FOXP3 mRNA expression by qRT-PCR. (FIG. 3e) Exogenous addition of dimethyl R-2-HG promotes methylation of FOXP3 promoter and its intronic CpG island in T cells cultured under $T_H17$ condition (day 4) or iTreg condition (day 5). CD4 naïve T cells, $T_H17$ cells (day 4) differentiated in the absence or presence of 0.5 mM dimethyl R-2-HG, fully differentiated $T_H17$ (day 5), and iTreg cells (day 5) differentiated in the absence or presence of 0.5 mM dimethyl R-2-HG were collected for DNA methylation analysis of FOXP3 promoter and its intronic CpG island by bisulfate sequencing. ●, methylated cytosine; ○, demethylated cytosine. (FIG. 3f) AOA promoted hypomethylation of FOXP3 promoter and its intronic CpG island in T cells under $T_H17$ (day 6) and iTreg condition (day 5). Cells differentiated in the absence or presence of AOA under $T_H17$ condition (day 6) or iTreg condition (day 5) were collected for DNA methylation analysis of FOXP3 promoter and its intronic CpG island by bisulfate sequencing. ●, methylated cytosine; ○, demethylated cytosine. Note that male mice were used in the experiments for FIG. 3e and FIG. 3f due to the X-chromosome inactivation, and the fact that FOXP3 is on the X-chromosome. (FIG. 3g) Knockdown of IDH1/2 suppressed $T_H17$ cell differentiation and reciprocally promoted iTreg cell differentiation. CD4 naïve T cells were differentiated under $T_H17$ condition, the cells were then infected with retrovirus containing shRNAs targeting IDH1, and/or IDH2, or empty vector PMKO.1-GFP. The GFP+ cells or GFP- cells were sorted and analyzed by intracellular staining of FOXP3 and IL-17.

FIGS. 10a-10d. Differentiating $T_H17$ Cells Highly Expressed IDH1 and IDH2, and shRNA Against IDH1 or IDH2 Effectively Suppressed the Expression of IDH1 or IDH2.

(FIG. 10a) Differentiating $T_H17$ cells or iTreg cells (day 3) were collected for mRNA expression analysis. All expression levels were normalized to β-actin, and the expression level of each enzyme was normalized to that in differentiating iTreg cells. (FIGS. 10b and 10c) Knockdown of IDH1 and/or IDH2 efficiently suppressed the mRNA expression of IDH1 and/or IDH2. Infected cells (GFP+ cells) containing shRNA against IDH1 or 2 were FACS sorted and re-stimulated with anti-CD3 and anti-CD28 for mRNA expression analysis. Expression was normalized to β-actin. Expression of IDH1 was plotted in FIG. 10b and that of IDH2 was plotted in FIG. 10c. FIG. 10d) Differentiated $T_H17$ cells and iTreg cells have similar expression of IDH3. The experiment was done exactly as in the experiment for FIG. 10a. Expression of IDH3 subunits was normalized to β-actin, and further plotted as relative level to that gene expression in iTreg cells.

Example 6: AOA Promotes Recovery from EAE Diseases

Figure 4A:
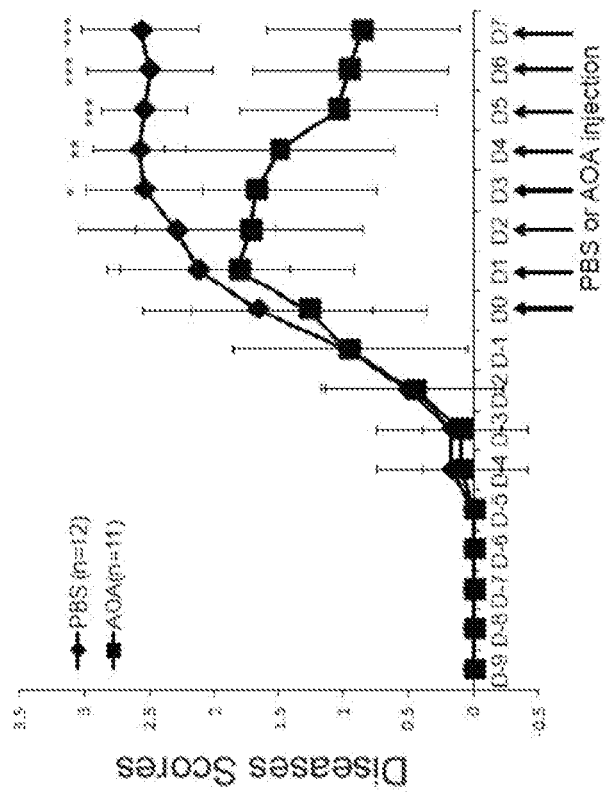
Figure 4D:
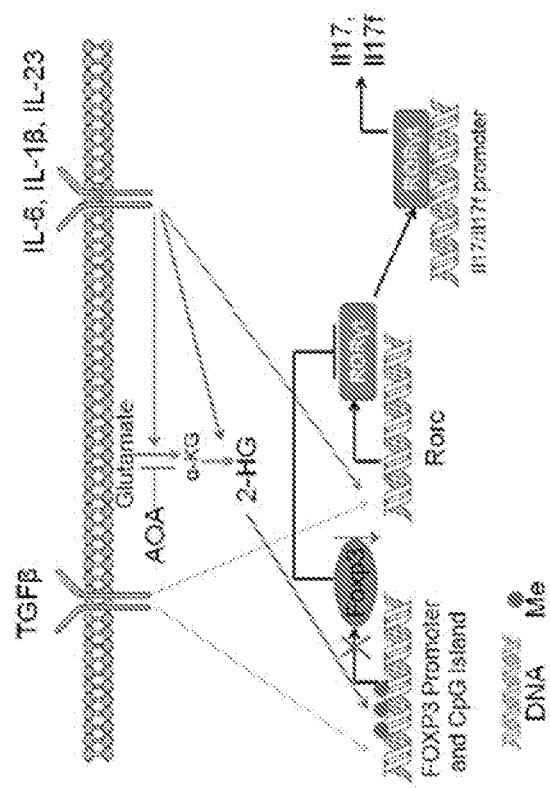
Figure 4C:
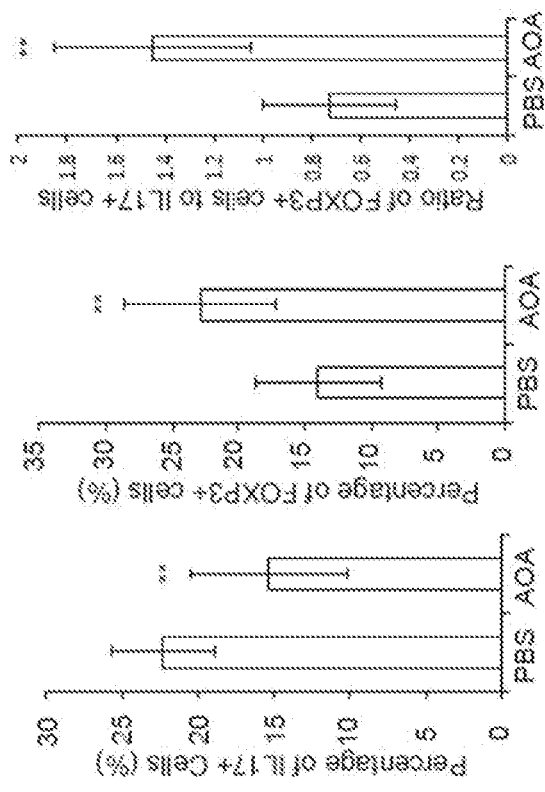

The in vitro findings that AOA regulates the $T_H17$/iTreg balance prompted an investigation into the effects of AOA in vivo in the context of a pathologic $T_H17$-dependent disease state. $T_H17$ cells are the major pathogenic cell population in experimental autoimmune encephalomyelitis (EAE), a mouse model of multiple sclerosis, but FOXP3+regulatory T cells suppress $T_H17$ cell-mediated inflammatory diseases, such as EAE. In the in vitro studies, AOA skewed $T_H17$ differentiation towards FOXP3+ iTreg cells and, therefore, offers a potential to treat $T_H17$-mediated autoimmune diseases. To test this possibility, EAE was induced in C57BL/6 mice by immunizing with myelin oligodendrocyte glycoprotein peptide (MOG35-55) in complete Freund's adjuvant (CFA) as described. AOA or control vehicle was injected daily intraperitoneally after a majority of the mice began to show obvious neurological signs, including tail paralysis that progressed to hind and front limb paralysis (disease score>1). Remarkably, AOA administration caused a significant recovery from EAE diseases in this therapeutic disease model (FIG. 4a). Consistent with this observation, AOA treatment significantly reduced the percentage of $T_H17$ cells in the central nervous system and increased the percentage of FOXP3+ T cells (p<0.01, FIGS. 4b and 4c). The ratio of FOXP3+ cells to IL17+ cells is much higher in AOA-treated mice than in control mice (FIG. 4c). This altered balance between Treg cells and $T_H17$ cells by AOA administration in vivo parallels the findings from in vitro cell culture studies and suggests that the metabolic pathway from glutamate to α-KG/2-HG plays a deterministic role in modulating the $T_H17$/Treg balance during an in vivo immune response (FIG. 4d). Although previous studies with AOA as a drug candidate did not progress further in human clinical trials possibly due to its toxicity, this study demonstrated that selectively targeting the glutamate metabolic pathway could alter the balance of $T_H17$/iTreg cells both in vitro and in vivo, and may represent a novel strategy for addressing $T_H17$-mediated autoimmune diseases.

FIGS. 4a-4d. AOA Produced a Significant Recovery from EAE Diseases.

EAE diseases were typically induced in mice. When the disease was very obvious (score>1), AOA or PBS was injected daily starting as shown (arrow) and recorded as day 0, and the disease scores were recorded in FIG. 4a). At the end of experiment, the mice were analyzed for brain and spinal cord infiltrated T cells by intracellular staining for FOXP3 and IL-17, and the representative of cell population was plotted in FIG. 4b, the statistics was calculated in FIG. 4c. FIG. 4d) Diagram shows the working mechanistic model. During $T_H17$ cell differentiation, glutamate-derived 2-HG is highly elevated and promotes methylation of FOXP3 promoter and intronic CpG island, and consequently turns off the transcription of FOXP3, essential for $T_H17$ cell differentiation. Inhibition of the conversion of glutamate into α-KG with AOA decreased 2-HG production, reduces the methylation level at FOXP3 gene locus, which promotes FOXP3 mRNA expression. This consequently inhibits $T_H17$ cell differentiation, and reciprocally promotes iTreg cell differentiation.

In summary, it is shown herein that increased transamination via Got1 leads to much greater accumulation of 2-HG in differentiating $T_H17$ cells than in iTreg cells. 2-HG functions as an antagonist of DNA demethylase, such as Tet1-2, to cause DNA hypermethylation. Therefore, the accumulated 2-HG in differentiating $T_H17$ cells might promote the methylation of FOXP3 gene locus and silence FOXP3 gene expression that is essential for $T_H17$ cell differentiation. Interestingly, it was found that 2-HG levels in differentiating $T_H17$ cells (e.g., 0.1-0.4 mM) were much lower than that in cancer cells harboring IDH1/2 mutations (at lower mili-molar range, ≥1 mM, this level of 2-HG has been demonstrated to cause DNA hypermethylation and cell transformation). Nonetheless, endogenous 2-HG accumulations under $T_H17$ condition and experiments with exogenously added 2-HG in $T_H17$ culture correlate well with hypermethylation of FOXP3 gene locus and reduced mRNA and protein level of FOXP3 in fully differentiated $T_H17$ cells, suggesting different cell types may exhibit differential sensitivity to 2-HG level. Manipulating a single step in a glutamate metabolic pathway could change $T_H17$ cell fate by affecting the methylation of FOXP3 gene locus, and ameliorate mouse EAE disease by regulating $T_H17$/iTreg balance, highlighting the importance of cellular metabolism in T-cell fate determination.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method of treating an autoimmune disease in an individual, comprising administering to the individual a therapeutically effective amount of an aspartate transaminase 1 (Got1) inhibitor, wherein the Got1 inhibitor is a small molecule inhibitor selected from the group consisting of: aminooxy-acetic acid (AOA), L-cycloserine, L-2-amino-4-methoxy-trans-but-3-enoic acid, 2-aminobut-3-enoic acid, and ethyl hydrazinoacetate.

2. The method of claim 1, wherein the therapeutically effective amount is sufficient to increase the ratio of peripheral regulatory T (iTreg) cells to IL-17- and IL-17F-producing helper T ($T_H17$) cells in a population of T cells in the individual, relative to a reference ratio of iTreg cells to $T_H17$ cells in a reference population of T cells.

3. The method of claim 2, wherein the reference population of T cells is obtained from the individual before the administering.

4. The method of claim 2, wherein the reference population of T cells is obtained from a cohort of one or more other individuals having or suspected of having the autoimmune disease.

5. The method of claim 4, wherein the cohort has not been administered with the Got1 inhibitor.

6. The method of claim 2, wherein the therapeutically effective amount is sufficient to increase the ratio by 30% or more relative to the reference ratio.

7. The method of claim 1, wherein the therapeutically effective amount is sufficient to reduce a proportion of $T_H17$ cells in the population of T cells, relative to a reference proportion of $T_H17$ cells from the reference population of T cells.

8. The method of claim 7, wherein the therapeutically effective amount is sufficient to reduce the proportion of $T_H17$ cells in the population of T cells by 20% or more.

9. The method of claim 1, wherein the method further comprises measuring, in a sample comprising a population of T cells obtained from the individual after the administering:
   a first number and/or proportion of $T_H17$ cells in the population; and/or
   a second number and/or proportion of iTreg cells in the population.

10. The method of claim 9, wherein the measuring comprises measuring a bulk expression level of, and/or a number of T cells expressing one or more markers for $T_H17$ cells and/or iTreg cells in the population.

11. The method of claim 1, wherein the Got1 inhibitor is AOA.

12. The method of claim 1, wherein the autoimmune disease is associated with a pathological activity of $T_H17$ cells in the individual.

13. The method of any one of claim 1, wherein the autoimmune disease is an inflammatory demyelinating disease.

14. The method of claim 1, wherein the autoimmune disease is acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behget's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD), mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjogren's syndrome; systemic lupus erythematosus; Takayasu's arteritis; temporal arteritis; vitiligo; warm autoimmune hemolytic anemia; anti myelin-associated glycoprotein (MAG) peripheral neuropathy; Devic's disease; chronic inflammatory demyelinating polyneuropathy or Wegener's granulomatosis.

15. The method of claim 1, wherein the method comprises co-administering two or more different treatments for the autoimmune disease.

16. The method of claim 14, wherein the inflammatory bowel disease (IBD) is Crohn's disease and/or ulcerative colitis.

* * * * *